(12) United States Patent  (10) Patent No.: US 7,919,250 B2
Blaser et al.  (45) Date of Patent: Apr. 5, 2011

(54) DIAGNOSTIC AND TREATMENT METHODS FOR CHARACTERIZING BACTERIAL MICROBIOTA IN SKIN CONDITIONS

(75) Inventors: Martin J. Blaser, New York, NY (US); Zhan Gao, Elmhurst, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 12/183,806

(22) Filed: Jul. 31, 2008

(65) Prior Publication Data
US 2009/0035329 A1  Feb. 5, 2009

Related U.S. Application Data

(60) Provisional application No. 60/962,870, filed on Jul. 31, 2007.

(51) Int. Cl.
A61K 39/02 (2006.01)
C07H 21/00 (2006.01)

(52) U.S. Cl. .............................. 435/6; 435/36; 536/23.7
(58) Field of Classification Search ......................... None
See application file for complete search history.

(56) References Cited

U.S. PATENT DOCUMENTS

| 6,982,273 | B1 | 1/2006 | Majeed et al. | |
|---|---|---|---|---|
| 7,183,057 | B2 * | 2/2007 | Benson | 435/6 |
| 2005/0221334 | A1 * | 10/2005 | Benson | 435/6 |
| 2006/0073130 | A1 * | 4/2006 | Farmer et al. | 424/93.46 |
| 2006/0286054 | A1 | 12/2006 | Gomez | |
| 2007/0015151 | A1 * | 1/2007 | Schrenzel et al. | 435/6 |
| 2007/0202540 | A1 * | 8/2007 | Benson | 435/7.1 |
| 2007/0238782 | A1 | 10/2007 | Chien et al. | |

FOREIGN PATENT DOCUMENTS

| WO | 00/60120 | * 10/2000 |
|---|---|---|
| WO | 2004/091569 | * 10/2004 |
| WO | 2006/136420 | * 12/2006 |
| WO | 2007/140622 | * 12/2007 |

OTHER PUBLICATIONS

Brook, I et al, International Journal of Dermatology, 1999, vol. 38, pp. 579-581, Microbiology of infected ustular psoriasis lesions.*
Dekio, Itaru et la, Journal of Medical Microbiology, 2005, vol. 54, pp. 1231-1238, Detection of potentially novel bacterial components of the human skin microbiotia using culture independent molecular profiling.*
Chitwood, La e tal, Applied Microbiology, Aug. 1969, vol. 18(2), pp. 193-197, Time, cost, and efficacy study of identifying Group A Streptococci with commerically available reagents.*

(Continued)

*Primary Examiner* — Patricia A Duffy
*Assistant Examiner* — Ginny Portner
(74) *Attorney, Agent, or Firm* — Fish & Richardson P.C.

(57) ABSTRACT

The present invention relates to methods for characterization of bacterial skin microbiota to provide diagnostic, therapeutic, and preventive measures for alleviating skin conditions. In certain embodiments, the invention relates to characterization of bacterial skin microbiota associated with psoriasis and related diagnostic, therapeutic, and preventive measures for alleviating psoriasis. These methods will be useful for detecting, diagnosing, and monitoring individuals who have or are at risk of certain skin conditions.

7 Claims, 6 Drawing Sheets

OTHER PUBLICATIONS

Kobayashi, Fujio et al, Infection and Immunity, Feb. 1980, vol. 27(2), pp. 391-396, Biphasic Protection against bacterial infection in Mice induced by vaccination of *Propionibacterium acnes*.*

Lodes, MJ et al, Microbiology, 2006, vol. 152, pp. 3667-3681, Variable expression of immunoreactive surface proteins of *Propionibacterium acnes*.*

Noah, PW, Seminars in Dermatology, Dec. 1990, vol. 9(4), pp. 269-276, The role of microorganisms in psoriasis.*

Okubo, Yukari et al, The Journal of Dermatology, vol. 29, pp. 547-555, 2002, Increased Microorganisms DNA levels in Peripheral Blood Monocytes from Psoriatic Patients Using PCR with Universal Ribosomal RNA primers.*

Treimo, J et al, Journal of Applied Microbiology, Total Bacterial and species specific 16S rDNA micro-array quantification of complex samples.*

Wang, Q et al, Arthritis and Rheumatism, vol. 42(10), Oct. 1999, pp. 2055-2059, V2 regions of 16S ribosomal RNA used as a Molecular Marker for the species identificaiton of streptoccoci in peripheral blood and synovial fluid from patients with psoriatic arthritis.*

Hoffler, U et al, Archive of Dermatology Research, 1980, vol. 268, pp. 297-312, Qualitative and Quantitiative Investigation on the Resident bacterial skin flora in Healthy person and in the Non-affected skin of Patients with Seborrheic Eczema.*

Baroni, A., et al., "Possible role of *Malassezia furfur* in psoriasis: modulation of TGF-β1, integrin, and HSP70 expression in human keratinocytes and in the skin of psoriasis-affected patients." 2004. J. Cutan. Pathal. 31:35-42.

Lebwohl, M. et al., "Psoriasis", 2003., Lancet 361: 1197-1204.

Schon, M. P., and W. H. Boehncke. "Psoriasis" 2005. *N. Engl. J. Med.* 352:1899-1912.

Waldman, A. et al., "Incidence of Candida in psoriasis-a study on the fungal flora of psoriatic patients." 2001. *Mycoses*; 44:77-81.

Gupta, A.K., et al., "Quantitative culture of *Malassezia* species from different body sites of individuals with or without dermatoses", 2001. *Med. Mycol.* 39:243-251.

Hernandez Hernandez, F., et al., "Species of *Malassezia* associated with various dermatoses and healthy skin in the Mexican population.", 2003. Rev. Iberoam. Micol. 20:141-144.

Prohic, A. et al., "Identification of *Malassezia* species isolated from scalp skin of patients with psoriasis and healthy subjects", 2003. *Croat*; 11:10-16.

Dekio, et al., "Detection of potentially novel bacterial components of the human skin microbiota using culture-independent molecular profiling", (2005) J. Med. Microbiol.; 54(12):1231-1238.

Fredricks, DN. (2001); *J Investig Dermatol Symp Proc* 6, 167-169.

Zoetendal, EG, Vaughan, EE & de Vos, WM. "A microbial world within us." (2006) Mol Microbiol 59, 1639-1650.

Schloss, PD & Handelsman, J. "Status of the Microbial Census" (2004) Microbiol Mol Biol Rev 68, 686-691.

Smit, E, Leeflang, P, Gommans, S, van den, BI, van Mil, S & Wemars, K. "Diversity and seasonal fluctuations of the dominant members of the bacterial soil community in a wheat field as determined by cultivation and molecular methods.", (2001) Appl Environ Microbiol 67, 2284-2291.

Harris, KA & Hartley, IC. "Development of broad-range 16S rDNA PCR for use in the routine diagnostic clinical microbiology service". (2003) J Med Microbiol 52, 685-691.

Saglani, S, Harris, KA, Wallis, C & Hartley, IC. "Empyema: the use of broad range 16S rDNA PCR for pathogen detection.", (2005) Arch Dis Child 90, 70-73.

Saiki et al., "Primer-directed enzymatic amplification of DNA with a thermostable DNA polymerase.", Science 1988, 239:487-491.

Southern et al., "Detection of specific sequences among DNA fragments separated by gel electrophoresis." J. Mol. Biol. 1975; 98: 503.

Hood et al., *Immunology, Second Ed.*, 1984, Benjamin/Cummings: Menlo Park, California, p. 384.

Gao, Z. et al., "Molecular analysis of human forearm superficial skin bacterial biota", 2007, Proc Natl Acad Sci USA, 104 (8):2927-2932.

Pei, Z., et al., "Bacterial biota in the human distal esophagus", (2004) Proc Natl Acad Sci USA 101, 4250-4255.

Edwards, U., et al., "Isolation and direct complete nucleotide determination of entire genes. Characterization of a gene coding for 16S ribosomal RNA" (1989) Nucleic Acids Res 17, 7843-7853.

Nagashima, K. et al., "Application of New Primer-Enzyme Combinations to Terminal Restriction Fragment Length Polymorphism Profiling of Bacterial Populations in Human Feces" (2003) Appl Environ Microbial 69, 1251-1262.

Maidak, B.L., et al., "The RDP-Il (Ribosomal Database Project)", (2001) Nucleic Acids Res 29, 173-174.).

Huber, T. et al., "Bellerophon: a program to detect chimeric sequences in multiple sequence alignments", (2004) Bioinjormatics 20, 2317-2319).

DeSantis, T.Z. Jr., et al., "NAST: a multiple sequence alignment server for comparative analysis of 16S rRNA genes", (2006) Nucleic Acids Res 34, W394-W399.

Ludwig, W., et al., "ARB: a software environment for sequence data.", (2004) Nucleic Acids Res 32, 1363-1371.

Kumar, S., et al., "MEGA3: Integrated software for molecular evolutionary genetics analysis and sequence alignment.", (2004) Brief Bioinform 5, 150-163.

Jukes, TH & Cantor, CR. "Evolution of protein molecules.", (1969) in Mammalian Protein Metabolism ed.Munro, HN. (Academic, New York,) pp. 21-132.

Saitou, N & Nei, M."The neighbor-joining method: a new method for reconstructing phylogenetic trees.", (1987) Mol Biol Evol4, 406-425.

Hughes, J.B., et al., "Counting the uncountable: statistical approaches to estimating microbial diversity.", (2001) *Appl Environ Microbiol* 67, 4399-4406.

Pavoine, S. et al.,"From dissimilarities among species to dissimilarities among communities: A Double Principal Coordinate Analysis,", (2004) J Theor Biol 228, 523-537.

Lozupone, C., et al, "UniFrac—An online tool for comparing microbial community diversity in a phylogenetic context", (2006) *BMC Bioinformatics* 7, 371.

Martin, AP. (2002). "Phylogenic Approaches for Describing and Comparing the Diversity fo Microbial Communities" *Appl Environ Microbiol* 68, 3673-3682.

EPO Supplementary European Search report and Search Opinion dated Oct. 6, 2010—PCT/US2008/071769.

\* cited by examiner

Distribution of 3,963 16S rDNA clones from normal and psoriatic samples, by phylum.

[a] CT (threshold cycle) corresponds to the minimum number of cycles at which the fluorescence can be detected

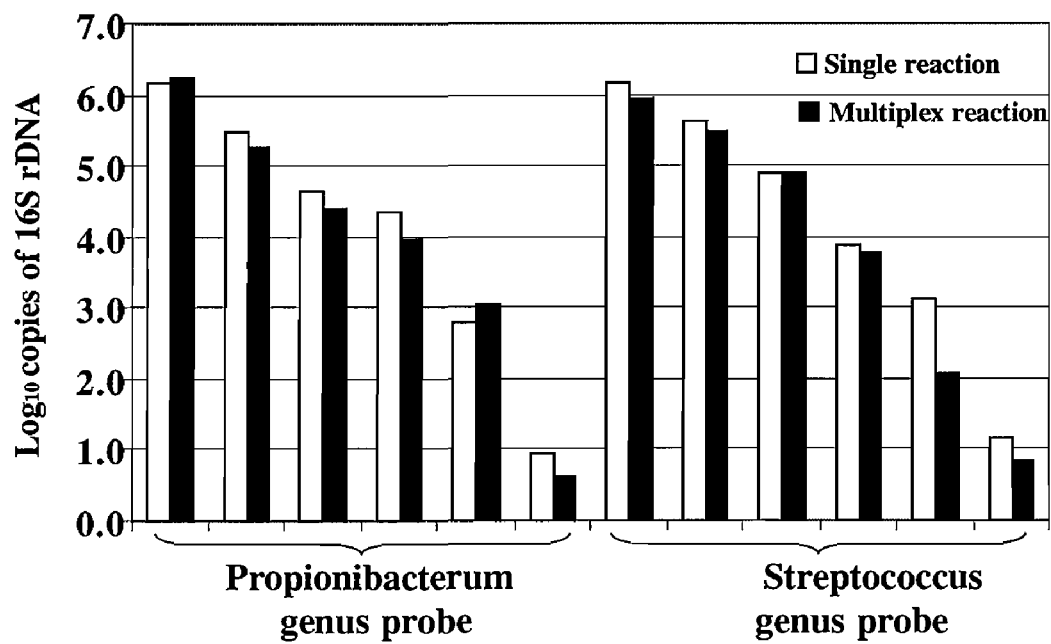
Fig. 6 Detection of specific 16S rDNA in single and multiplex qPCR reactions

DIAGNOSTIC AND TREATMENT METHODS FOR CHARACTERIZING BACTERIAL MICROBIOTA IN SKIN CONDITIONS

This application claims priority from U.S. Provisional Patent Application Ser. No. 60/962,870, filed Jul. 31, 2007, which is herein incorporated by reference in its entirety.

FEDERALLY SPONSORED RESEARCH OR DEVELOPMENT

This invention was made in part in the course of research sponsored by the National Institutes of Health (NIH) Grant RO1 GM 63270; the Ellison Medical Foundation; Diane Belfer Program for Microbial Ecology; and a Bernard Levine Scholarship. The U.S. government may have certain rights in this invention.

FIELD OF THE INVENTION

The present invention relates to characterization of microbiota associated with various skin conditions and related diagnostic, therapeutic, and preventive measures for alleviating the skin conditions. In certain embodiments, the invention relates to characterization of microbiota associated with psoriasis and related diagnostic, therapeutic, and preventive measures for alleviating, treating, or preventing psoriasis.

BACKGROUND OF THE INVENTION

Psoriasis is a common dermatosis of unknown cause. It is characterized as a chronic inflammatory condition of human skin. Psoriasis is estimated to affect about 3% of the population in industrialized countries (Baroni, A., et al., 2004. *J. Cutan. Pathol.* 31:35-42.), and is typically characterized by erythrosquamous cutaneous lesions associated with abnormal patterns of keratinocyte growth and differentiation (Lebwohl, M. 2003., *Lancet* 361:1197-1204). The classic symptoms of psoriasis are raised, red patches of skin topped with loose, silvery scales, usually on the knees or elbows.

There are several types of psoriasis. Symptoms for each type may vary in severity and appear in a wide array of combinations. In general, the major symptoms of psoriasis include: Bright red areas of raised patches (plaques) on the skin, often covered with loose, silvery scales. Plaques can occur anywhere, but commonly they occur on the knees, elbows, scalp, hands, feet, or lower back. Nearly 90% of people with psoriasis have plaque-type psoriasis.

Other manifestations of psoriasis include tiny areas of bleeding when skin scales are picked or scraped off (Auspitz's sign). Some individuals experience mild scaling to thick, crusted plaques on the scalp. Some patients experience itching, especially during sudden flare-ups or when the psoriasis patches are in body folds, such as under the breasts or the buttocks.

Nail disorders are common, especially in severe psoriasis and include the following symptoms: tiny pits in the nails (not found with fungal nail infections); yellowish discoloration of the toenails and possibly the fingernails; separation of the end of the nail from the nail bed; and a buildup of skin debris under the nails.

Other symptoms of psoriasis may include symmetrical plaques on the same areas on both sides of the body (for example, both knees or both elbows).

In certain instances patients experience flare-ups of many raindrop-shaped patches. Called guttate psoriasis, this condition often follows an infection with Group A Beta-hemolytic *Streptococcus pyogenes* (Group A strep; GAS) and is the second most common type of psoriasis. It affects less than 10% of those with psoriasis.

Finally, some psoriasis patients experience joint swelling, tenderness, and pain (psoriatic arthritis). These symptoms may occur in up to 39% of people with psoriasis.

Koebner's phenomenon can occur when a person with psoriasis has an injury (such as a cut, burn, or excess sun exposure) to an area of the skin that is not affected by psoriasis. Psoriasis patches then appear on the injured skin or any other part of the skin from several days to about 2 weeks after the injury.

Inflammatory aspects of the disease involve dermal angiogenesis, infiltration of activated T cells, and increased cytokine levels. One of these cytokines, IL-15, triggers inflammatory cell recruitment, angiogenesis, and production of other inflammatory cytokines, including IFN-□ TNF-□, and IL-17, which are all upregulated in psoriatic lesions. Although psoriasis has an unknown etiology, certain trigger factors, including physical trauma and GAS infections as described above, have been hypothesized to provoke clinical manifestations of psoriasis (Schon, M. P., and W. H. Boehncke. 2005. *N. Engl. J. Med.* 352:1899-1912). Fungal organisms, including *Candida albicans* (Waldman, A. et al., 2001. *Mycoses;* 44:77-81) and *Malassezia furfur* (Baroni, A., et al., 2004. *J. Cutan. Pathol.* 31:35-42.), have also been associated with the development of psoriatic skin lesions, and differences have been observed in the Malassezia species distributions in healthy subjects and patients with psoriasis (Gupta, A. K., et al., 2001. *Med. Mycol.* 39:243-251.; Hernandez Hernandez, F., et al., 2003. *Rev. Iberoam. Micol.* 20:141-144.; Prohic, A. 2003. *Croat;* 11:10-16.). Recent studies have also begun to characterize bacterial populations of human skin by using culture-independent molecular techniques (Dekio, I., et al., (2005) *J. Med. Microbiol.;* 54(12):1231-1238.

The human skin has been considered to harbor a complex microbial ecosystem (Fredricks, D N. (2001); *J Investig Dermatol Symp Proc* 6, 167-169), with transient, short-term resident and long-term resident biota, based on the consistency with which they are isolated. *Staphylococcus, Micrococcus, Corynebacterium, Brevibacteria, Propionibacteria,* and *Acinetobacter* species, among others, are regularly cultivated from normal skin. *Staphylococcus aureus, Streptococcus pyogenes,* (GAS) and *Pseudomonas aeruginosa* may be transient colonizers, especially in pathological conditions. Environmental factors, such as temperature, humidity, and light exposure, and host factors, including gender, genotype, immune status, and cosmetic use, all may affect microbial composition, population size, and community structure.

Knowledge of the human skin biota, chiefly through cultivation-based studies, is considerably limited in assessing compositions of complex microbial communities. In contrast, broad-range PCR primers targeted to highly conserved regions makes possible the amplification of small subunit rRNA genes (16S rDNA) sequences from all bacterial species (Zoetendal, E G, Vaughan, E E & de Vos, W M. (2006) *Mol Microbiol* 59, 1639-1650), and the extensive and rapidly growing 16S rDNA database facilitates identification of sequences to the species or genus level (Schloss, P D & Handelsman, J. (2004) *Microbiol Mol Biol Rev* 68, 686-691). Such techniques are increasingly used for identifying bacterial species in complex environmental niches (Smit, E, Leeflang, P, Gommans, S, van den, B J, van Mil, S & Wernars, K. (2001) *Appl Environ Microbiol* 67, 2284-2291), including the human mouth, esophagus, stomach, intestine, feces, and vagina, and for clinical diagnosis (Harris, K A & Hartley, J C.

(2003) *J Med Microbiol* 52, 685-691; Saglani, S, Harris, K A, Wallis, C & Hartley, J C. (2005) *Arch Dis Child* 90, 70-73).

Although certain fungal associations and genetic and immunological features of skin conditions such as psoriasis have been examined, the role of bacterial microbiota in psoriasis has not been understood. Thus, there remains a need for methods for diagnosing, treating and preventing skin conditions such as psoriasis, particularly based on characterizing and altering bacterial microbiota to alleviate the condition. Until the present studies, little has been known about the species composition in cutaneous skin samples, and in particular there has been no comparison between bacterial species composition in normal skin and in psoriatic lesions.

SUMMARY OF THE INVENTION

The present invention provides methods for characterizing and determining differences between bacterial populations in healthy or normal skin and in diseased skin, including in psoriatic lesions. Embodiments of the present invention relate to a bacterial signature or marker for psoriasis.

In certain embodiments, the invention relates to determining that at least one *Propionibacterium* species is underrepresented (i.e., found in low amounts or proportions) in diseased or affected skin, when compared with the amount of at least one *Propionibacterium* species found in healthy skin. In certain embodiments, the invention relates to determining the amount of at least one *Propionibacterium* species; wherein a low amount of at least one *Propionibacterium* species indicates psoriasis. In certain embodiments, the diseased or affected skin is a psoriatic lesion. In certain embodiments, the species is *Propionibacterium acnes* (*P. acnes*). In certain embodiments, the invention relates to determining that a low amount of at least one *Propionibacterium* species in psoriatic skin lesions when compared with the amount found in unaffected or healthy skin is a marker for psoriasis.

In further embodiments, the invention relates to diagnostic methods utilizing the amount of at least one *Propionibacterium* species in psoriatic skin lesions compared with the amount of at least one *Propionibacterium* species found in healthy skin as a marker for psoriasis.

In still further embodiments, the invention relates to determining a stage of psoriasis utilizing the proportion of *Propionibacterium* species in psoriatic skin lesions compared with the proportion of *Propionibacterium* found in healthy skin.

In additional embodiments, the invention relates to altering or replacing *Propionibacterium* species in the skin of patients in need of such treatment, including in psoriatic skin lesions of the patients. In further embodiments, the invention relates to altering or replacing *Propionibacterium acnes* in the skin of patients in need of such treatment, including in psoriatic lesions of the patients.

In additional embodiments, the invention relates to agents and methods for promoting growth of *Propionibacterium* species in the skin of psoriatic patients in need of such treatment. In additional embodiments, the invention relates to agents and methods for promoting growth of *Propionibacterium* species prophylactically in the skin of patients in need of such treatment. In certain embodiments, the *Propionibacterium* species is *Propionibacterium acnes*.

In additional embodiments, the invention relates to methods for treating psoriasis comprising administering an effective amount of at least one *Propionibacterium* species to affected skin in a patient in need of such treatment. In certain embodiments, at least one *Propionibacterium* species includes live *Propionibacterium* cells, killed or inactivated cells, or an extract from the cells. In additional embodiments, the cells may be derived from cells grown under ordinary circumstances or grown to induce increased production of particular constituents.

In additional embodiments, the invention relates to methods for monitoring effectiveness of therapies for psoriasis by measuring changes in the density or proportion of *Propionibacterium* species in the skin of psoriatic patients including in psoriatic skin lesions of patients. In certain embodiments, the *Propionibacterium* species is *Propionibacterium acnes*.

In yet further embodiments, the invention relates to determining the proportion of at least one non-Group A *Streptococcus* species (NGS) in affected or diseased skin of patients, including in psoriatic skin lesions of patients.

In certain embodiments, the invention relates to determining that at least one NGS species is overrepresented (i.e., found in an elevated amount) in psoriatic skin lesions, when compared with the amount of at least one NGS found in healthy or unaffected skin. In certain embodiments, the invention relates to determining that a high proportion of NGS in psoriatic skin lesions when compared with healthy skin, is a marker for psoriasis.

In additional embodiments, the invention relates to inhibiting the growth of or lowering the amount of at least one NGS in the skin of psoriatic patients including in psoriatic skin lesions of patients. In certain embodiments, inhibiting or lowering the amount of at least one NGS includes antibiotic treatment and/or chemical and physical means of inhibiting or lowering the amount of at least one NGS. In certain embodiments, inhibiting or lowering the amount of at least one NGS includes chemical and/or physical means of inhibiting or lowering the amount of at least one NGS.

In further embodiments, the invention relates to diagnostic methods utilizing the proportion of at least one NGS species in psoriatic lesions compared with healthy skin as a marker for psoriasis.

In still further embodiments, the invention relates to determining a stage of psoriasis utilizing the proportion of at least one NGS species in psoriatic lesions compared with healthy skin.

In additional embodiments, the invention relates to methods for monitoring therapies for psoriasis by measuring changes in the density or amount of at least one NGS species in the skin of psoriatic patients including in psoriatic lesions of patients.

In additional embodiments, the invention relates to methods for determining the amount of at least one *Propionibacterium* species in a psoriatic skin lesion in a patient; wherein a low amount of at least one *Propionibacterium* species in a psoriatic lesion indicates psoriasis.

In additional embodiments, the invention relates to methods for monitoring treatment of psoriasis comprising: determining an amount of at least one *Propionibacterium* species in a psoriatic skin lesion in a patient; wherein a low amount of at least one *Propionibacterium* species in a psoriatic lesion indicates psoriasis and wherein an increase in the amount of at least one *Propionibacterium* species in a psoriatic lesion indicates treatment progress.

In yet additional embodiments, the invention relates to methods for diagnosing psoriasis comprising: determining a ratio of a non-Group A *Streptococcus* species (NGS) to a *Propionibacterium* species (gS/P ratio) in a psoriatic skin lesion in a patient; and wherein a raised gS/P ratio indicates psoriasis.

In additional embodiments, the invention relates to vaccine compositions and vaccinations for suppressing at least one NGS species in the skin of patients in need of such treatment. In certain embodiments, the invention relates to vaccine compositions and vaccinations for prophylactically reducing the incidence of psoriasis in patients in need of such treatment.

In additional embodiments, the invention relates to methods for diagnosing and monitoring treatment of psoriasis by determining the ratio of non-Group A *Streptococcus* species (NGS) to *Propionibacterium* species to (gS/P ratio) (i.e, (S) standing for non-Group A *Streptococcus* species and (P) standing for *Propionibacterium* and (g) standing for genus) in psoriatic lesions compared with the ratio found in healthy skin. In certain embodiments, the *Propionibacterium* species is *Propionibacterium acnes*.

In additional embodiments, the invention relates to methods for determining a raised gS/P ratio for diagnosing and monitoring treatment of psoriasis in patients in need of such treatment.

In additional embodiments, the invention relates to methods for treating or preventing psoriasis by lowering the gS/P ratio.

In additional embodiments, the invention relates to vaccine compositions and related methods for lowering the gS/P ratio in the skin in patients in need of such treatment. In certain embodiments, the invention relates to vaccine compositions and related methods for prophylactically lowering the gS/P ratio in the skin and reducing the incidence of psoriasis in patients in need of such treatment.

In additional embodiments, the invention relates to a method for treating psoriasis in a patient comprising administering an effective amount of inactivated or killed *Propionibacterium* cells to the patient in need of such treatment. In further embodiments, the invention relates to a method for treating psoriasis in a patient comprising administering an effective amount of killed or inactivated *Propionibacterium acnes* cells to the patient in need of such treatment. In yet additional embodiments, the invention relates to a method for treating psoriasis in a patient comprising administering an effective amount of an extract from *Propionibacterium* to the patient in need of such treatment. In certain embodiments, the *Propionibacterium* is *Propionibacterium acnes*.

In additional embodiments, the invention relates to methods for diagnosing a skin disease comprising: a. determining the amount of at least one desired bacterial species in a skin sample suspected of being diseased from a patient; b. determining the amount of at least one desired bacterial species in a healthy skin sample from the patient; c. comparing the amounts in part a) and b); and d. wherein an altered amount of the at least one desired bacterial species in a skin sample suspected of being diseased when compared with a healthy skin sample indicates a skin disease. In certain embodiments, the skin disease is selected from the group consisting of atopic dermatitis, acne, alopecia, seborrhea, dandruff, and pemphigus. In certain embodiments, the determining comprises performing quantitative polymerase chain reaction (qPCR). In additional embodiments, amplified target DNA from the qPCR reaction is characterized by fluorescent emission detected by binding of one or more of a labeled probe selected from the group consisting of SEQ ID NO:6 and SEQ ID NO:8 to the amplified target DNA.

In yet additional embodiments, the invention relates to a kit for determining a bacterial signature comprising at least one nucleic acid selected from the group consisting of SEQ ID NO:6 and SEQ ID NO:8. In yet further embodiments, the invention relates to an isolated nucleic acid fragment comprising SEQ ID NO:6 or SEQ ID NO:8.

BRIEF DESCRIPTION OF THE DRAWINGS

FIG. 2A shows percentages of bacteria from skin samples from healthy individuals and from normal skin of patients with psoriasis. FIG. 2B shows percentages of bacteria from skin samples from psoriatic lesions from patients with psoriasis.

FIG. 3A shows percentages of bacteria from skin samples from healthy individuals and from normal skin of patients with psoriasis. FIG. 3B shows percentages of bacteria from skin samples from psoriatic lesions from patients with psoriasis.

FIG. 6 shows detection of specific 16S rDNA in single and multiplex qPCR reactions.

DETAILED DESCRIPTION

Figure 1:
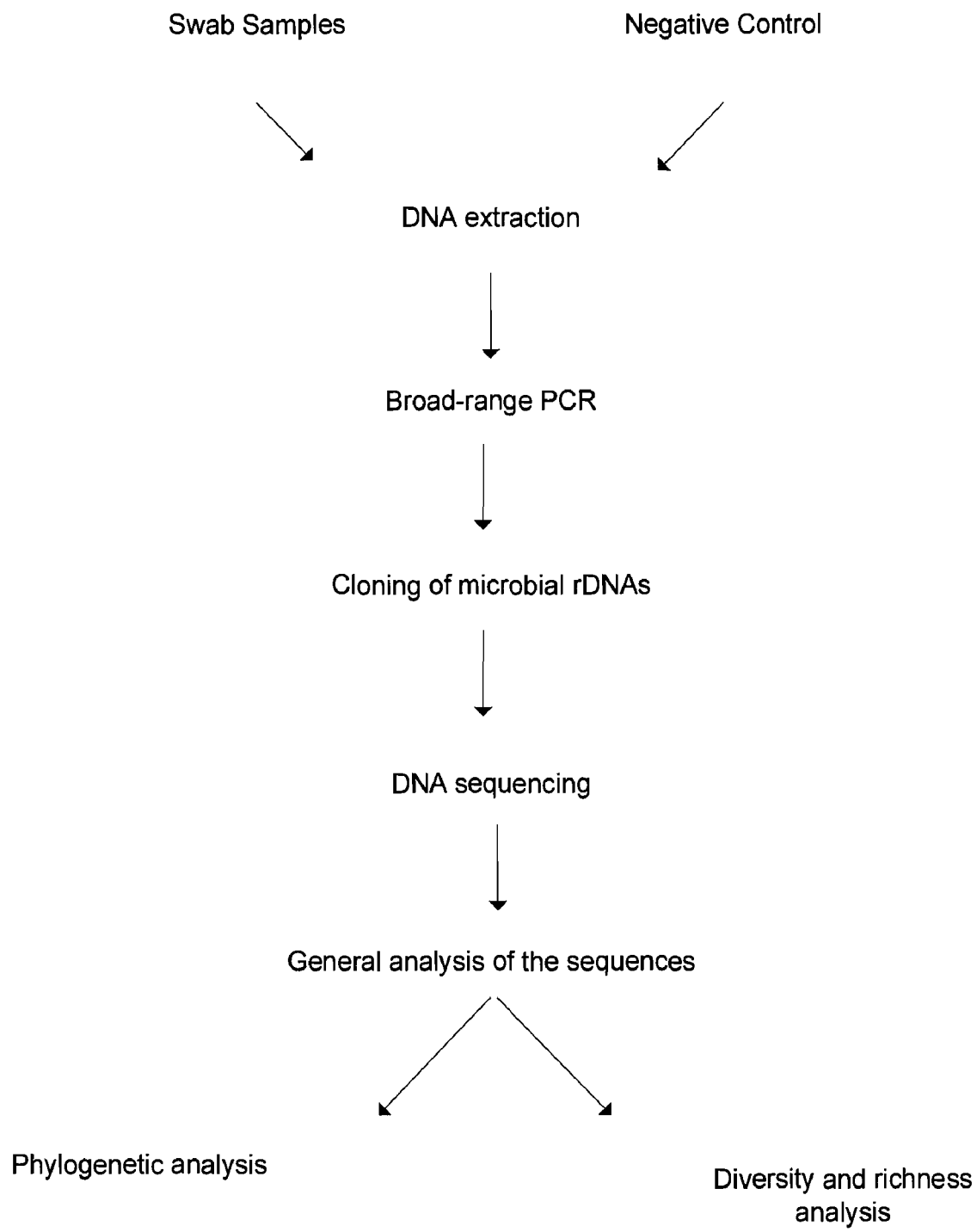
FIG. 1 shows a flow diagram of exemplary methods for determining skin microbiota.

The present invention relates generally to characterizing skin microbiota under various conditions and comparing normal and diseased skin microbiota in order to determine a microbial signature for the desired condition. The microbiota is determined utilizing a broad range molecular approach. While any number of suitable molecular techniques may be utilized, particularly useful molecular techniques to identify bacteria and archaea include PCR from a desired sample, cloning of microbial ribosomal 16S rRNA (16S rDNA), sequencing and analysis. In contrast to techniques involving cultivation of microorganisms from skin samples, this molecular approach, based on sequencing the 16S rRNA gene conserved in all bacteria, permits analysis of variable regions that allow identification of bacterial species and inferences about phylogenetic relationships with known bacteria. FIG. 1 is a schematic showing exemplary methods for determining skin microbiota.

Assessing microbial populations in human skin using molecular techniques involving the ribosomal operon provides for comparisons between the populations of bacteria present in healthy (or uninvolved skin) and diseased skin, such as skin affected by psoriasis (e.g., psoriatic lesions). This process is applicable to a variety of skin conditions including, but not limited to atopic dermatitis, acne, alopecia, seborrhea, dandruff, and pemphigus.

Determining the bacterial profiles in skin affected by a condition compared with the bacterial profile of healthy or unaffected skin, provides the ability to develop diagnostic, treatment, and preventive measures for the condition.

In accordance with the present invention, there may be numerous tools and techniques within the skill of the art, such as those commonly used in molecular immunology, cellular immunology, pharmacology, and microbiology. See, e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J.

In accordance with the present invention there may be employed conventional molecular biology, microbiology, protein expression and purification, antibody, and recombinant DNA techniques within the skill of the art. Such techniques are explained fully in the literature. See, e.g., Sambrook, Fritsch and Maniatis, *Molecular Cloning: A Laboratory Manual*, Second Edition (Cold Spring Harbor Laboratory Press, New York: 1989); *DNA Cloning: A Practical Approach*, Volumes I and II (Glover ed.: 1985); *Oligonucleotide Synthesis* (Gait ed.: 1984); *Nucleic Acid Hybridization* (Hames & Higgins eds.: 1985); *Transcription And Translation* (Hames & Higgins, eds.: 1984); *Animal Cell Culture* (Freshney, ed.: 1986); *Immobilized Cells And Enzymes* (IRL Press: 1986); Perbal, *A Practical Guide To Molecular Cloning* (1984); Ausubel et al., eds. *Current Protocols in Molecular Biology*, (John Wiley & Sons, Inc.: 1994); and Harlow and Lane. *Antibodies: A Laboratory Manual* (Cold Spring Harbor Laboratory Press: 1988).

Common abbreviations correspond to units of measure, techniques, properties or compounds as follows: "min" means minutes, "h" means hour(s), "μL" means microliter(s), "mL" means milliliter(s), "mM" means millimolar, "M" means molar, "mmole" means millimole(s), "kb" means kilobase, and "bp" means base pair(s). "Polymerase chain reaction" is abbreviated PCR; "Reverse transcriptase polymerase chain reaction" is abbreviated RT-PCR; and "Sodium dodecyl sulfate" is abbreviated SDS.

"Amplification" of DNA as used herein denotes the use of polymerase chain reaction (PCR) to increase the concentration of a particular DNA sequence within a mixture of DNA sequences. For a description of PCR see Saiki et al., Science 1988, 239:487.

A "polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotides (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radio-isotopes, fluorescent molecules, biotin, and the like.

The term "nucleic acid hybridization" refers to anti-parallel hydrogen bonding between two single-stranded nucleic acids, in which A pairs with T (or U if an RNA nucleic acid) and C pairs with G. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an anti-parallel hybrid). See *Molecular Biology of the Cell*, Alberts et al., 3$^{rd}$ ed., New York and London: Garland Publ., 1994, Ch. 7.

Typically, hybridization of two strands at high stringency requires that the sequences exhibit a high degree of complementarity over an extended portion of their length. Examples of high stringency conditions include: hybridization to filter-bound DNA in 0.5 M NaHPO$_4$, 7% SDS, 1 mM EDTA at 65° C., followed by washing in 0.1×SSC/0.1% SDS at 68° C. (where 1×SSC is 0.15M NaCl, 0.15M Na citrate) or for oligonucleotide molecules washing in 6×SSC/0.5% sodium pyrophosphate at about 37° C. (for 14 nucleotide-long oligos), at about 48° C. (for about 17 nucleotide-long oligos), at about 55° C. (for 20 nucleotide-long oligos), and at about 60° C. (for 23 nucleotide-long oligos)). Accordingly, the term "high stringency hybridization" refers to a combination of solvent and temperature where two strands will pair to form a "hybrid" helix only if their nucleotide sequences are almost perfectly complementary (see *Molecular Biology of the Cell*, Alberts et al., 3$^{rd}$ ed., New York and London: Garland Publ., 1994, Ch. 7).

Conditions of intermediate or moderate stringency (such as, for example, an aqueous solution of 2×SSC at 65° C.; alternatively, for example, hybridization to filter-bound DNA in 0.5 M NaHPO$_4$, 7% SDS, 1 mM EDTA at 65° C., and washing in 0.2×SSC/0.1% SDS at 42° C.) and low stringency (such as, for example, an aqueous solution of 2×SSC at 55° C.), require correspondingly less overall complementarity for hybridization to occur between two sequences. Specific temperature and salt conditions for any given stringency hybridization reaction depend on the concentration of the target DNA and length and base composition of the probe, and are normally determined empirically in preliminary experiments, which are routine (see Southern, *J. Mol. Biol.* 1975; 98: 503; Sambrook et al., *Molecular Cloning: A Laboratory Manual*, 2$^{nd}$ ed., vol. 2, ch. 9.50, CSH Laboratory Press, 1989; Ausubel et al. (eds.), 1989, *Current Protocols in Molecular Biology*, Vol. I, Green Publishing Associates, Inc., and John Wiley & Sons, Inc., New York, at p. 2.10.3).

As used herein, the term "standard hybridization conditions" refers to hybridization conditions that allow hybridization of sequences having at least 75% sequence identity. According to a specific embodiment, hybridization conditions of higher stringency may be used to allow hybridization of only sequences having at least 80% sequence identity, at least 90% sequence identity, at least 95% sequence identity, or at least 99% sequence identity.

Nucleic acid molecules that "hybridize" to any desired nucleic acids of the present invention may be of any length. In one embodiment, such nucleic acid molecules are at least 10, at least 15, at least 20, at least 30, at least 40, at least 50, and at least 70 nucleotides in length. In another embodiment, nucleic acid molecules that hybridize are of about the same length as the particular desired nucleic acid.

As used herein, the term "isolated" means that the referenced material is removed from the environment in which it is normally found. Thus, an isolated biological material can be free of cellular components, i.e., components of the cells in which the material is found or produced. Isolated nucleic acid molecules include, for example, a PCR product, an isolated mRNA, a cDNA, or a restriction fragment. Isolated nucleic acid molecules also include, for example, sequences inserted into plasmids, cosmids, artificial chromosomes, and the like. An isolated nucleic acid molecule is preferably excised from the genome in which it may be found, and more preferably is no longer joined to non-regulatory sequences, non-coding sequences, or to other genes located upstream or downstream of the nucleic acid molecule when found within the genome. An isolated protein may be associated with other proteins or nucleic acids, or both, with which it associates in the cell, or with cellular membranes if it is a membrane-associated protein.

"Treating" or "treatment" of a state, disorder or condition includes:

(1) preventing or delaying the appearance of clinical symptoms of the state, disorder, or condition developing in a person who may be afflicted with or predisposed to the state, disorder or condition but does not yet experience or display clinical symptoms of the state, disorder or condition; or (2) inhibiting the state, disorder or condition, i.e., arresting, reducing or delaying the development of the disease or a relapse thereof (in case of maintenance treatment) or at least one clinical symptom, sign, or test, thereof; or (3) relieving the disease, i.e., causing regression of the state, disorder or condition or at least one of its clinical or sub-clinical symptoms or signs.

The benefit to a subject to be treated is either statistically significant or at least perceptible to the patient or to the physician.

An "immune response" refers to the development in the host of a cellular and/or antibody-mediated immune response to a composition or vaccine of interest. Such a response usually consists of the subject producing antibodies, B cells, helper T cells, suppressor T cells, regulatory T cells, and/or cytotoxic T cells directed specifically to an antigen or antigens included in the composition or vaccine of interest.

As used herein, the term "vaccine" refers to a composition comprising a cell or a cellular antigen, and optionally other pharmaceutically acceptable carriers, administered to stimulate an immune response in an animal, most preferably a human, specifically against the antigen and preferably to engender immunological memory that leads to mounting of a protective immune response should the subject encounter that antigen at some future time. Vaccines often include an adjuvant.

A "therapeutically effective amount" means the amount of a compound that, when administered to an animal for treating a state, disorder or condition, is sufficient to effect such treatment. The "therapeutically effective amount" will vary depending on the compound, the disease and its severity and the age, weight, physical condition and responsiveness of the animal to be treated.

The compositions of the invention may include a "therapeutically effective amount" or a "prophylactically effective amount" of an antibody or antigen-binding portion of the invention. A "therapeutically effective amount" refers to an amount effective, at dosages and for periods of time necessary, to achieve the desired therapeutic result. A therapeutically effective amount of an antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

While it is possible to use a composition provided by the present invention for therapy as is, it may be preferable to administer it in a pharmaceutical formulation, e.g., in admixture with a suitable pharmaceutical excipient, diluent or carrier selected with regard to the intended route of administration and standard pharmaceutical practice. Accordingly, in one aspect, the present invention provides a pharmaceutical composition or formulation comprising at least one active composition, or a pharmaceutically acceptable derivative thereof, in association with a pharmaceutically acceptable excipient, diluent and/or carrier. The excipient, diluent and/or carrier must be "acceptable" in the sense of being compatible with the other ingredients of the formulation and not deleterious to the recipient thereof.

The compositions of the invention can be formulated for administration in any convenient way for use in human or veterinary medicine. The invention therefore includes within its scope pharmaceutical compositions comprising a product of the present invention that is adapted for use in human or veterinary medicine.

In a preferred embodiment, the pharmaceutical composition is conveniently administered as an oral formulation. Oral dosage forms are well known in the art and include tablets, caplets, gelcaps, capsules, and medical foods. Tablets, for example, can be made by well-known compression techniques using wet, dry, or fluidized bed granulation methods.

Such oral formulations may be presented for use in a conventional manner with the aid of one or more suitable excipients, diluents, and carriers. Pharmaceutically acceptable excipients assist or make possible the formation of a dosage form for a bioactive material and include diluents, binding agents, lubricants, glidants, disintegrants, coloring agents, and other ingredients. Preservatives, stabilizers, dyes and even flavoring agents may be provided in the pharmaceutical composition. Examples of preservatives include sodium benzoate, ascorbic acid and esters of p-hydroxybenzoic acid. Antioxidants and suspending agents may be also used. An excipient is pharmaceutically acceptable if, in addition to performing its desired function, it is non-toxic, well tolerated upon ingestion, and does not interfere with absorption of bioactive materials.

Acceptable excipients, diluents, and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient, diluent, and carrier can be selected with regard to the intended route of administration and standard pharmaceutical practice.

As used herein, the phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopeias for use in animals, and more particularly in humans.

"Patient" or "subject" refers to mammals and includes human and veterinary subjects.

The dosage of the therapeutic formulation will vary widely, depending upon the nature of the disease, the patient's medical history, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc., to maintain an effective dosage level. In some cases, oral administration will require a higher dose than if administered intravenously. In some cases, topical administration will include application several times a day, as needed, for a number of days or weeks in order to provide an effective topical dose.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, olive oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

As used herein, the term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed.*, 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, and potentially useful human adjuvants such as N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine, and BCG (*bacille Calmette-Guerin*). Preferably, the adjuvant is pharmaceutically acceptable.

In the case of the present invention, parenteral routes of administration are also possible. Such routes include intravenous, intra-arteriole, intramuscular, intradermal, subcutaneous, intraperitoneal, transmucosal, intranasal, rectal, vaginal, or transdermal routes. If desired, inactivated therapeutic formulations may be injected, e.g., intravascular, intratumor, subcutaneous, intraperitoneal, intramuscular, etc.

In a preferred embodiment, the route of administration is topical. Although there are no physical limitations to delivery of the formulation, topical delivery is preferred because of its ease and convenience, and because topical formulations readily accommodate additional mixtures commonly in the form of a cream, ointment, lotion, salve, or as a component added to a bath.

Typical topical formulations or products occur in a variety of forms, including solids, liquids, suspensions, semisolids (such as creams, gels, pastes or "sticks"), powders or finely dispersed liquids such as sprays or mists. Examples of topical products commonly classified as "cosmetics" include skin care products such as creams, lotions, moisturizers and "treatment cosmetics" such as exfoliants and/or skin cell renewal agents; toners and astringents; pre-moistened wipes and washcloths; tanning lotions; bath products such as oils; as well as powders and sprays; skin colorant and make-up products such as foundations, blushes, rouges, eye shadows and liners, lip colors and mascaras; lip balms and sticks; hair care and treatment products such as shampoos, conditioners, colorants, dyes, bleaches, straighteners and permanent wave products; baby products such as baby lotions, oils, shampoos, powders and wet wipes. Examples of topical products commonly classified as "topical drugs" are many and varied, and include over-the-counter and/or prescription products such as antiperspirants, insect repellents, sunscreens and sunburn treatments, anti-acne agents, antibiotics, topical respiratory agents, ocular drugs such as eyedrops and saline solutions, therapeutic retinoids, anti-dandruff agents, external analgesics such as capsaicin products, topical contraceptives, topical drug delivery systems, gastrointestinal agents such as suppositories, enemas and hemorrhoid treatments, reproductive system agents such as vaginal treatments, and many other products with therapeutic or other effects. Other topical products include hand, facial and body soaps and detergents and other forms of skin cleansers, as well as solvents, propellants, polishes, lubricants, adhesives, waxes and others which are either applied topically or are topically exposed to the body during normal use.

In the present invention, the terms normal, unaffected, or healthy skin refer to skin that does not demonstrate signs of psoriasis or any other recognized skin condition. Normal, unaffected, healthy skin may be used to refer to the skin from a patient with psoriasis, that is, does not exhibit symptoms of psoriasis. Furthermore, samples of normal, unaffected, or healthy skin are taken from individuals who have not been treated with any antibiotics for at least one month prior to sampling.

A psoriatic lesion is an area of skin that exhibits any of the signs of psoriasis including raised, red patches of skin topped with loose, silvery scales, often on the knees or elbows, and other extensor surfaces, but can be present anywhere.

As used herein, promoting the growth of *Propionibacterium* and agents that promote growth of *Propionibacterium* are ones that result in a desired amount of at least one *Propionibacterium* species in a desired location. In particular embodiments, the growth is promoted in the skin area corresponding to the psoriatic lesion of a patient. Agents that promote growth of *Propionibacterium* species may include pre-biotics that favor the metabolism of *Propionibacterium* species over that of competing organisms in the skin. In certain embodiments, an effective amount of *Propionibacterium* species is applied to the skin area corresponding to the psoriatic lesion of a patient in order to promote growth of at least one *Propionibacterium* species. The active ingredient may be live *Propionibacterium* cells, killed or inactivated cells, or an extract from the cells. Each of these forms may be derived from cells grown under ordinary circumstances or grown to induce increased production of particular constituents.

As used herein, inhibiting the growth of NGS may include using any agents, antibiotics, chemical, or physical means, or combinations thereof to inhibit the growth or eliminate NGS organisms. At the highest level, antibiotics can be classified as either bactericidal or bacteriostatic. Bactericidal agents kill bacteria directly whereas bacteriostatics prevent them from dividing. However, these classifications are based on laboratory behavior; in practice, both of these are capable of ending a bacterial infection, or suppressing bacterial growth. Examples of suitable antibiotics for inhibiting the growth of, or killing, or preventing growth of NGS species include agents listed in Table 1:

TABLE 1

Types of antimicrobial agents that can be used to suppress NGS.

| Generic Name | Brand Names |
| --- | --- |
| Loracarbef | Lorabid |
| Ertapenem | Invanz |
| Imipenem/Cilastatin | Primaxin |
| Meropenem | Merrem |
| Cefadroxil | Duricef |
| Cefazolin | Ancef |
| Cephalexin | Keflex |
| Cefaclor | Ceclor |
| Cefamandole | Mandole |
| Cefoxitin | Mefoxin |
| Cefprozil | Cefzil |
| Cefuroxime | Ceftin |
| Cefixime | |
| Cefdinir | Omnicef |
| Cefditoren | |
| Loracarbef | Lorabid |
| Cefoperazone | Cefobid |
| Cefotaxime | Claforan |
| Cefpodoxime | |
| Ceftazidime | Fortum |
| Ceftibuten | |
| Ceftizoxime | |
| Ceftriaxone | Rocephin |
| Cefepime | Maxipime |
| Teicoplanin | |
| Vancomycin | Vancocin |
| Azithromycin | Zithromax, Sumamed, Zitrocin |
| Clarithromycin | Biaxin |
| Dirithromycin | |
| Erythromycin | |
| Roxithromycin | |
| Troleandomycin | |
| Aztreonam | |
| Amoxicillin | Novamox |
| Ampicillin | |
| Azlocillin | |
| Carbenicillin | |
| Cloxacillin | |
| Dicloxacillin | |
| Flucloxacillin | |
| Mezlocillin | |
| Nafcillin | |
| Penicillin | |
| Loracarbef | Lorabid |
| Piperacillin | |
| Ticarcillin | |
| Bacitracin | |
| Colistin | |
| Polymyxin B | |
| Ciprofloxacin | Cipro, Ciplox |
| Enoxacin | |
| Gatifloxacin | Tequin |
| Levofloxacin | Levaquin |
| Lomefloxacin | |
| Moxifloxacin | Avelox |
| Norfloxacin | |
| Ofloxacin | Ocuflox |
| Trovafloxacin | Trovan |
| Mafenide | |
| Prontosil (archaic) | |
| Sulfacetamide | |
| Sulfamethizole | |
| Sulfanilimide (archaic) | |
| Sulfasalazine | |
| Sulfisoxazole | |
| Trimethoprim | |
| Trimethoprim-Sulfamethoxazole (Co-trimoxazole) (TMP-SMX) | Bactrim |
| Demeclocycline | |
| Doxycycline | Vibramycin |
| Minocycline | Minocin |
| Oxytetracycline | |
| Loracarbef | Lorabid |
| Tetracycline | Sumycin |
| Chloramphenicol | Chloromycetin |
| Clindamycin | Cleocin |
| Ethambutol | |
| Fosfomycin | |
| Fusidic acid | |
| Furazolidone | |
| Isoniazid | |
| Linezolid | Zyvox |
| Metronidazole | Flagyl |
| Mupirocin | |
| Nitrofurantoin | Macrodantin, Macrobid |
| Platensimycin | |
| Pyrazinamide | |
| Quinupristin/Dalfopristin | Syncercid |
| Rifampin | |
| Spectinomycin | |
| Telithromycin | Ketek |

However, other chemical formulations including astringents, antiseptics, pre-biotics, and physical means such as occlusive dressings with particular impregnations (of any suitable chemical formulation or antimicrobial agent) could also be useful as means for suppressing NGS. In certain embodiments, it may be useful to utilize at least one chemical which acts as a skin "exfoliant" such as retinoids (e.g. tretinoin, retinol and retinal), carboxylic acids including □-hydroxy acids (e.g. lactic acid, glycolic acid), β-hydroxy acids (e.g. salicylic acid), α-keto acids, acetic acid and trichloroacetic acid, 1-pyrrolidone-5-carboxylic acid, capryloyl salicylic acid, α-hydroxy decanoic acid, α-hydroxy octanoic acid, gluconolactone, methoxypropyl gluconamide, oxalic acid, malic acid, tartaric acid, mandelic acid, benzylic acid, gluconic acid, benzoyl peroxide or phenol.

As described herein, characterizing and comparing the bacterial microbiota of normal/healthy skin with that of diseased skin, such as psoriatic lesions provide a microbial signature useful in diagnosing, treating, and preventing psoriasis. Because human skin is extensive and variable in its characteristics, typically a single site, the volar forearm was sampled in order to maximize homogeneity and allow analysis of bilateral conservation.

In certain embodiments, the invention provides a kit comprising useful probes or primers for analyzing skin microbiota in any of the methods described herein. In certain embodiments, the kits may be packaged in association with instructions teaching a method of using the primers or probes according to one or more of the methods described herein. The kit can also optionally contain any useful buffers, controls, or other reagents that are useful in PCR or qPCR reactions or any of the methods described herein. Additionally, in certain embodiments, the invention relates to any one or more of the isolated nucleic acid probes or primers for amplifying or detecting desired bacteria from a sample, as described herein. Such primers and/or probes are useful in PCR and qPCR reactions for determining the bacterial biota of superficial skin.

Initial studies providing molecular analysis of normal human forearm superficial skin bacterial biota were described. (Gao, Z. et al., 2007, *Proc Natl Acad Sci USA*, 104(8):2927-2932). For the initial 1,221 clones analyzed, 182 SLOTUs (species-level operational taxonomic units) belonging to 8 phyla were identified, estimated as 74.0% (95% CI: 64.8%~77.9%) of the SLOTUs in this ecosystem; an average of 48.0±12.2 SLOTU were found in each subject. Three phyla, Actinobacteria, Firmicutes, and Proteobacteria, accounted for 94.6% of the clones. Most (85.3%) of the bacterial sequences corresponded to known and cultivated species, but 98 (8.0%) clones, comprising 30 phylotypes, had <97% similarity to prior database sequences. Only 6 (6.6%) of the 91 genera and 4 (2.2%) of the 182 SLOTUs, respectively, were found in all six subjects.

Analysis of 817 clones obtained 8 to 10 months later from four subjects, showed new phyla (2), genera (28), and SLOTU (65). Only four (3.4%) of the 119 genera (*Propionibacteria, Corynebacteria, Staphylococcus*, and *Streptococcus*) were observed in each subject tested twice, but these represented 54.4% of all clones. These results show that the bacterial biota in normal skin is highly diverse, with few well-conserved and well-represented genera, but otherwise low-level interpersonal consensus (Gao et al. PNAS 2007; 104; 2927-32).

Materials and Methods.
Subjects.

Specimens from superficial skin were obtained from the left and right forearms of six healthy subjects (three males and three females); second samples were obtained 8-10 months later from four of these subjects. The mean age of the subjects was 38 years of age (range, 21-54 years of age); all were in good health and had not received any antibiotics for at least one month. The study was approved by the New York University Institutional Review Board, and all subjects provided written informed consent.

From each healthy subject, at least two samples were obtained from the left and right forearms and, for four subjects, another sample was obtained from each forearm 8-10 months after the first. From each patient with psoriasis, at least three skin samples, including unaffected skin and two or three samples from psoriatic lesions, were studied. Lesions differing in the extent of erythema, swelling, and scaling were chosen. No patient had ever received therapy for psoriasis. Samples were obtained in a DNA-free clean room by rubbing the skin using two sterile cotton swabs soaked in ST solution (0.15 M NaCl with 0.1% Tween 20). The head of each swab was aseptically cut from the handle, placed into a microcentrifuge tube containing 100 µl of ST solution, centrifuged for 5 min, and then removed. To detect possible contamination, negative controls were prepared using cotton swabs in ST solution without any contact with skin and then subjected to the above-mentioned procedures.

Specimen Processing.

DNA was extracted from the swabs in a PCR-free cleanroom by using the DNeasy Tissue Kit (Qiagen, Chatsworth, Calif.); because Gram-positive bacteria are more resistant to lysis than Gram-negative organisms, the manufacturer's protocol for genomic DNA isolation from Gram-positive bacteria was followed. Samples were eluted in 100 µl of AE buffer, and to eliminate bacterial or DNA contamination, the enzymatic lysis buffer was passed through a micro-centrifuge filter (MW threshold 30,000 daltons; Amicon, Bedford, Mass.) at 747×g for 20 min.

DNA Isolation.

DNA was extracted from the swabs in a PCR-free cleanroom by using the DNeasy Tissue Kit (Qiagen, Chatsworth, Calif.) utilizing the steps described below.

1. Bacterial cells were harvested from the swabs in a microcentrifuge tube by centrifuging for 10 min at 5000×g (7500 rpm). The supernatant was discarded.
2. The bacterial pellet was resuspended in 180 µl enzymatic lysis buffer (20 mM Tris.Cl, pH 8.0; 2 mM sodium EDTA; 1.2% Triton ®X-100; 20 mg/ml lysozyme).
3. The pellet suspension was incubated for at least 30 min at 37° C.
4. 25 µl proteinase K and 200 µl Buffer AL was added and mixed by vortexing.
5. The sample was incubated at 70° C. for 30 min.
6. 200 µl ethanol (100%) was added to the sample, and mixed thoroughly by vortexing.
7. The mixture from step 6 was transferred by pipette into the DNeasy Minispin column (Qiagen, Valencia, Calif.) placed in a 2 ml collection tube and centrifuged at ≧6000×g (8000 rpm) for 1 min. The flow-through and collection tube were discarded.
8. The DNeasy Minispin column was placed in a new 2 ml collection tube, 500 µl Buffer AW1 was added, and the column was centrifuged for 1 min at ≧6000×g (8000 rpm). The flow-through and collection tube were discarded.
9. The DNeasy Mini spin column was placed in a new 2 ml collection tube, 500 µl Buffer AW2 was added, and the column was centrifuged for 3 min at 20,000×g (14,000 rpm) to dry the DNeasy membrane. The flow-through and collection tube were discarded.
10. The DNeasy Mini spin column was placed in a clean 1.5 ml or 2 ml microcentrifuge tube, and 100 µl Buffer AE was pipette directly onto the DNeasy membrane. The column was incubated at room temperature for 5 min, and then centrifuged for 1 min at ≧6000×g (8000 rpm) to elute.

16S rDNA PCR Amplification.

Universal bacterial 16S rDNA PCR primers 8F (forward primer 5'-AGA GTT TGA TYM TGG CTC AG (SEQ ID NO:1)) and 1510R (reverse primer 5'-TAC GGY TAC CTT GTT ACG ACT T (SEQ ID NO:2) were used to amplify the approximately 1.5 kb region corresponding to positions 8 to 1513 of the *Escherichia coli* 16S rDNA gene by using a 30-cycle PCR (as described in Pei, Z., et al., (2004) *Proc Natl Acad Sci USA* 101, 4250-4255; Edwards, U., et al., (1989) *Nucleic Acids Res* 17, 7843-7853; and Nagashima, K. et al., (2003) *Appl Environ Microbiol* 69, 1251-1262). To each 5 µl of the suspension of extracted template DNA was added 45 µl of a PCR mixture containing 5 µl of 10×PCR buffer (Qiagen, Valencia, Calif.), 2.5 mM MgCl$_2$, 200 µM each dNTP, 20 pmol of each primer, and 5 units of TaqDNA polymerase. PCR was performed for 2 min at 94° C., followed by 30 amplification cycles of 45 s at 94° C., 30 s at 52° C., and 90 s at 72° C., with a final cycle for 20 min at 72° C. The results of PCR amplification were examined by electrophoresis on 1% agarose gels.

16S rDNA Clone Libraries.

The PCR products were separated from free PCR primers by using a PCR purification kit (Qiagen, Valencia, Calif.), ligated with the pGEM-T-Easy vector (Promega, Madison, Wis.), used to transform *E. coli* DH5α competent cells, and clones analyzed. Putatively positive clones were screened by PCR with Sp6/T7 primers. The cloned inserts underwent sequence analysis using PCR primers 8F (forward primer 5'-AGA GTT TGA TYM TGG CTC AG (SEQ ID NO:1)) and 27R (reverse primer 5'-CGA CAI CCA TGC AIC ACC T (SEQ ID NO:3), corresponding to position 8 to 1064 of the *E. coli* 16S rDNA (complete *E. coli* 16S rDNA shown in SEQ ID NO:4; which corresponds with GenBank Accession No. J01859). Each sequence was manually edited in conjunction with its chromatogram with Sequencher, adjusting for quality. DNA sequences of ≈980 bases were obtained initially to determine either identity or approximate phylogenetic position. For those clones containing inserts of ambiguous phylogenetic status, nearly full-length 16S bacterial rDNA sequences (≈1,400 bp) were obtained, using the additional primer, 1510R (reverse primer 5'-TAC GGY TAC CTT GTT ACG ACT T (SEQ ID NO:2). For identification of closest relatives, the newly determined sequences were compared with those available in the Ribosomal Database Project (RDP) II (release 9.39) (Maidak, B.L., et al., (2001) *Nucleic Acids Res* 29, 173-174.) and GenBank (available at ncbi.nlm.gov) databases, by using the standard nucleotide-nucleotide BLAST program to ascertain their closest relatives.

Elimination of Contaminating Sequences.

Because reagents used in DNA extraction and PCRs may contain bacteria or their genomic DNA, and under certain experimental conditions these contaminating DNA molecules may become detectable after PCR amplification, a reagent control was utilized that included all DNA extraction and PCR reagents but without the skin sample, which was examined in parallel using the identical procedures as for the skin sample DNA. After electrophoresis and ethidium bromide staining, preparations from these controls did not generate any visible bands, but the agarose gel at the expected location of the signal was excised, ligated to pGEM-T Easy Vector (Promega) and transformed. Clones derived from these reagent controls underwent sequence analysis, and sequences of known species and unknown species were identified. For a more conservative data analysis, the species found in both control and skin samples were excluded.

Sequence Deposition.

All sequences that are not classifiable by using the current 16S database at RDP II were deposited in the GenBank database (Accession Nos. DQ130020-DQ130049 and DQ847437-DQ847450, and corresponding to SEQ ID NO:10 to SEQ ID NO:53).

Statistical Methods.

Double principal coordinate analysis (DPCoA) uses phylotype differences to derive the dissimilarity matrix of samples and calculate the sample diversity. In this analysis, the dissimilarities between different phylotypes are calculated based on the sum of distance to the common ancestor of two phylotypes on phylotype tree. To facilitate the visualization of sample dissimilarity and diversity, the first two orthogonal principal axes were obtained based on the sample dissimilarity, and were plotted to show the distribution of samples in a two-dimensional space. The diversity information can be decomposed into within- and between-samples diversity values. This allowed the use of a "pseudo F" statistic (the ratio of within-cluster diversity and between-cluster diversity) to examine possible clustering phenomena, and significance was evaluated by permutation tests. The P test also was used to assess for significant differences between samples.

Phylogenetic Analysis

All sequences were examined for chimerism by using Chimera Detection at Ribosomal database Project (RDP) II (release 8.1) and Bellerophon (Huber, T. et al., (2004) *Bioinformatics* 20, 2317-2319). In total, only three clones were removed from the phylogenetic analysis. The remaining sequences were compared with those of RDP II (release 9.39) (Maidak, BL. et al., (2001) *Nucleic Acids Res* 29, 173-174.) and in GenBank to identify SLOTUs, as reported (Pei, Z., et al., (2004) *Proc Natl Acad Sci USA* 101, 4250-4255.). The sequences were aligned with NAST at Greengenes (available at greengenes.lbl.gov/cgi-bin/nph-index.cgi), (DeSantis, T. Z. Jr., et al., (2006) *Nucleic Acids Res* 34, W394-W399.). Misalignments were manually curated in ARB (Ludwig, W., et al., (2004) *Nucleic Acids Res* 32, 1363-1371.), and then hypervariable regions were masked by using MASK COLUMNS at Greengenes. The phylogenetic trees were generated by using MEGA 3.1 (Kumar, S., et al., (2004) *Brief Bioinform* 5, 150-163.). Evolutionary distances were calculated with the Jukes-Cantor algorithm (Jukes, TH & Cantor, CR. (1969) in Mammalian Protein Metabolism ed. Munro, HN. (Academic, New York,) pp. 21-132.). The statistical strength of the Neighbor-Joining method was assessed by bootstrap resampling (1,000 replicates) (Saitou, N & Nei, M. (1987) *Mol Biol Evol* 4, 406-425.).

Statistical Analyses.

The total number of SLOTUs that may be present in the sampled human skin and its associated confidence interval were calculated by using a nonparametric richness estimator, Chao1, as described by Hughes, J. B., et al., (2001) *Appl Environ Microbiol* 67, 4399-4406). DPCoA (Pavoine, S. et al., (2004) *J Theor Biol* 228, 523-537) and the P test (Lozupone, C., et al., (2006) *BMC Bioinformatics* 7, 371; and Martin, A P. (2002) *Appl Environ Microbiol* 68, 3673-3682) were used to evaluate sample diversity and the relationships among samples.

EXAMPLE 1

Ratio of the Genus *Streptococcus* to *Propionibacterium*

Figure 2:
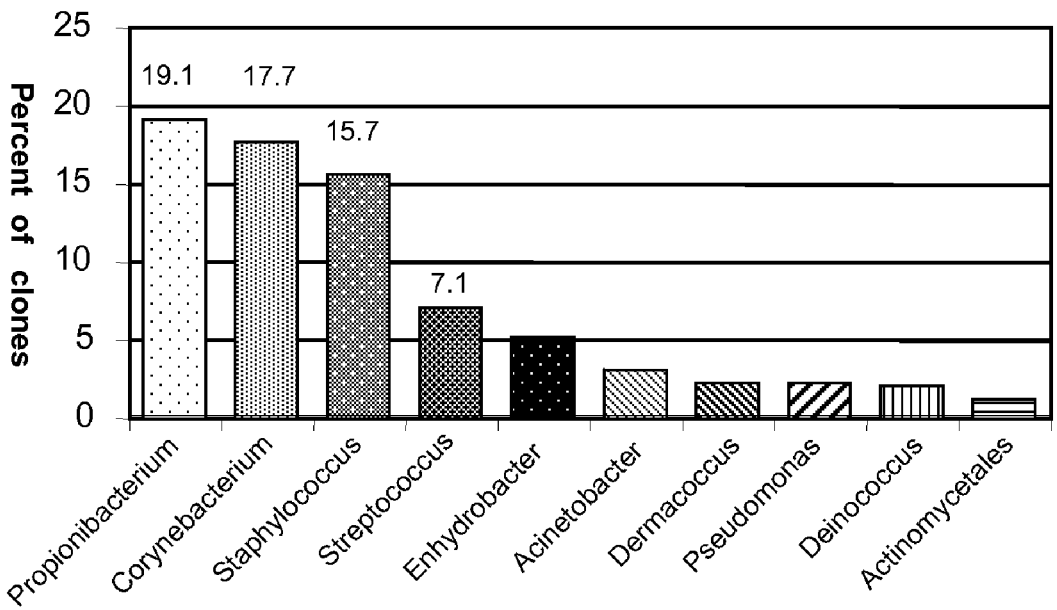
FIG. 2 A-B show samplings of the ten most common genera of bacteria found in human skin based on 16S rDNA clone analysis.
Figure 2:
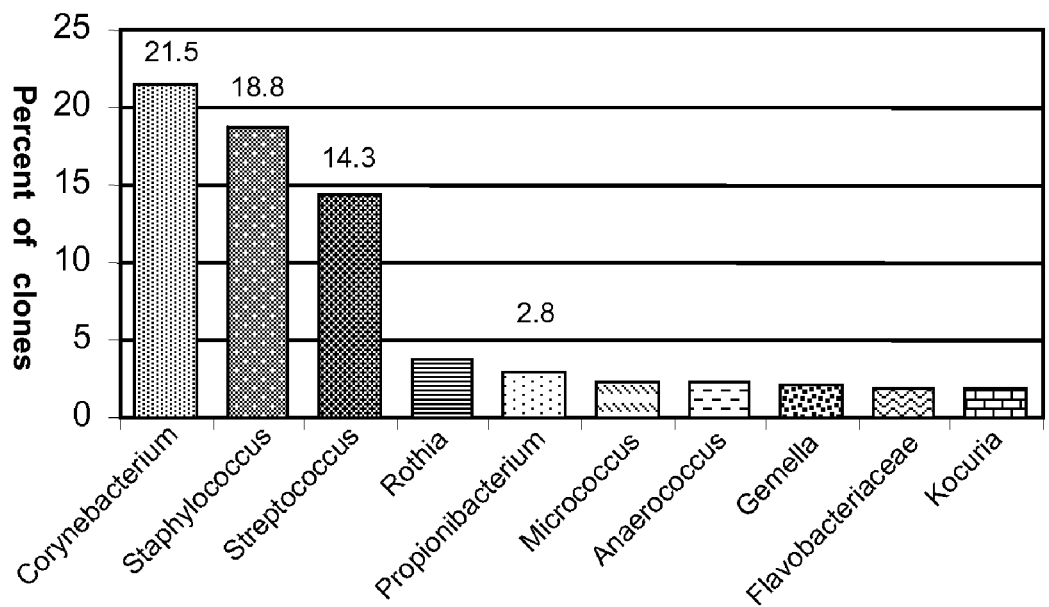

FIGS. 2A-B show samplings of the ten most common genera of bacteria found in human skin based on 16S rDNA clone analysis performed on samples as described above. FIG. 2A shows the percentages of bacteria from skin samples from healthy individuals and from normal skin of patients with psoriasis (n=2,649 clones). These results show that the skin from healthy persons and the normal skin of patients with psoriasis exhibit a gS/P ratio of 0.4. (i.e., ratio of genus *Streptococcus* to *Propionibacterium*=0.4.

FIG. 2B shows the results of skin samples from lesions of patients with psoriasis (n=1,314 clones). These results show that the skin from psoriatic lesions exhibit a gS/P ratio of 5.0 (i.e., ratio of *Streptococcus* to *Propionibacterium*=5.0).

EXAMPLE 2

Ratio of *Streptococcus mitis* to *Propionibacterium acnes* (sS/P)

Figure 3:
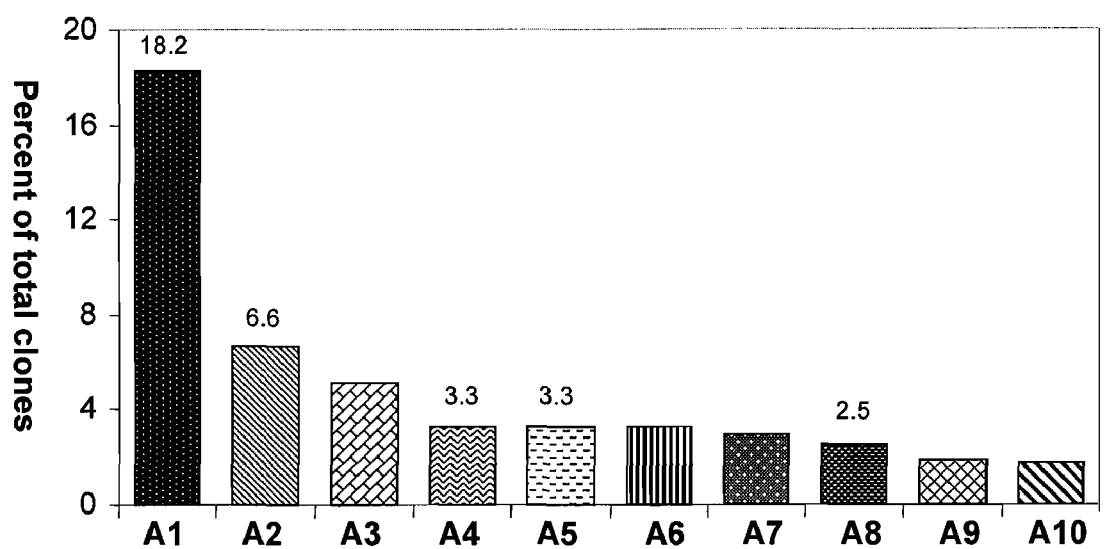
FIG. 3 A-B are representations of the ten most common species of bacteria found in human skin based on 16S rDNA clone analysis.
Figure 3:
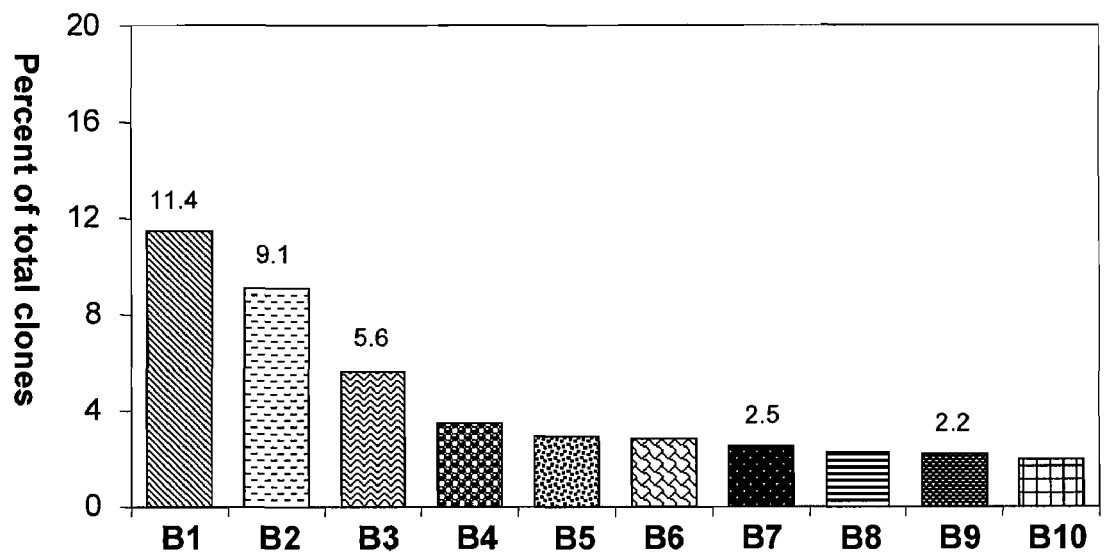

FIG. 3 shows the percent of clones of the 10 most common bacterial species found in human skin, based on 16S rDNA clones. FIG. 3A shows the results of skin samples from healthy persons and normal skin of patients with psoriasis (n=2,649 clones). These results show that the skin from healthy persons and the normal skin of patients with psoriasis exhibit an sS/P ratio of 0.2 (i.e., ratio of the species *Streptococcus mitis* to *Propionibacterium acnes*=0.2).

FIG. 3B shows the results of skin samples from lesions of patients with psoriasis (n=1,314 clones). These results show that the skin from psoriatic lesions exhibit an sS/P ratio of 2.5

(i.e., ratio of the species *Streptococcus mitis* to *Propionibacterium acnes*=2.5). The bars in the graphs are labeled and correspond to the following bacterial species: *Propionibacterium acnes* (A1, B7); *Corynebacterium tuberculostearicum* (A2, B1); *Staphylococcus hominis* (A5, B2); *Streptococcus mitis* (A4, B3); *Staphylococcus epidermidis* (A8, B9); *Enhydrobacter aerosaccus* (A3); *Staphylococcus capitis* (A6); *Staphylococcus caprae* (A7); *Dermacoccus* AF409025 (A9); *Corynebacterium mucifaciens* (A10); *Corynebacterium simulans* (B4); *Rothia mucilaginosa* (B5); *Staphylococcus aureus* (B6); *Streptococcus salivarius* (B8); *Flavobacteriaceae* DQ337018 (B10).

EXAMPLE 3

Characterization of the Presence of 16s rDNA from Bacterial Genera Found in Skin Samples from Healthy Individuals (or Normal Skin from Psoriatic Patients) and in Skin Samples from Psoriatic Lesions from Psoriatic Patients The presence of 16S rDNA from *Propionibacterium*, *Streptococcus*, *Staphylococcus* and *Corynebacterium* found in healthy (e.g., no obvious signs of disease or skin condition) skin samples from six individuals was determined as shown in Table 2.

TABLE 2

Presence of 16S rDNA from four genera found in skin samples from six healthy individuals

| | | Percent | | | | |
|---|---|---|---|---|---|---|
| Samples[a] | No. of clones | *Propionibacterium* | *Streptococcus* | *Staphylococcus* | *Corynebacterium* | Any of the 4 |
| AT | 208 | 10.6 | 7.7 | 3.4 | 1.4 | 23.1 |
| BT | 204 | 12.3 | 5.9 | 2.9 | 7.4 | 28.5 |
| CT | 202 | 12.4 | 5.9 | 16.8 | 26.2 | 61.3 |
| DT | 204 | 14.7 | 2.0 | 18.6 | 44.6 | 79.9 |
| ET | 203 | 23.2 | 10.8 | 15.8 | 21.2 | 71.0 |
| FT | 200 | 59.5 | 2.5 | 9.5 | 13.5 | 85.0 |
| AT2 | 203 | 2.0 | 2.5 | 2.0 | 1.0 | 7.5 |
| CT2 | 206 | 37.9 | 32.0 | 1.9 | 1.5 | 73.3 |
| ET2 | 202 | 9.9 | 7.9 | 8.4 | 7.4 | 33.6 |
| FT2 | 206 | 28.6 | 3.9 | 29.6 | 18.9 | 81.0 |
| Mean ± SD | 203.8 ± 2.3 | 21.1 ± 17.0 | 8.1 ± 8.9 | 10.9 ± 9.2 | 14.3 ± 13.9 | 54.4 ± 28.4 |

[a]Samples from each participant at one sampling time (2 sites).

The presence of 16S rDNA from *Propionibacterium*, *Streptococcus*, *Staphylococcus* and *Corynebacterium* found in psoriatic lesions of skin samples from patients with psoriasis was determined as shown in Table 3.

TABLE 3

Presence of 16S rDNA from four genera found in skin samples from Psoriatic Patients

| | | Percent | | | | |
|---|---|---|---|---|---|---|
| Samples[a] | No. of clones | *Propionibacterium* | *Streptococcus* | *Staphylococcus* | *Corynebacterium* | Any of the 4 |
| 1PT | 207 | 14.0 | 15.0 | 24.2 | 18.8 | 72.0 |
| 2PT | 299 | 1.3 | 2.3 | 23.7 | 8.7 | 36.0 |
| 3PT | 200 | 1.0 | 22.5 | 1.5 | 38.5 | 63.5 |
| 4PT | 204 | 0 | 31.4 | 5.9 | 2.0 | 39.3 |
| 6PT | 203 | 1.0 | 12.3 | 35.5 | 5.4 | 54.2 |
| 8PT | 201 | 0 | 8.0 | 19.4 | 62.7 | 90.1 |
| Mean ± SD | 219.0 ± 39.3 | 2.9 ± 5.5 | 15.3 ± 10.4 | 18.4 ± 12.6 | 22.7 ± 23.6 | 59.3 ± 20.5 |

The presence of 16S rDNA from four bacterial genera found in the lesions from six patients with psoriasis is shown, by lesion in Table 4.

TABLE 4

Presence of 16S rDNA from four genera found in the lesions from six patients with psoriasis, by lesion

| | | Percent | | | | |
|---|---|---|---|---|---|---|
| Sample | No. of Clones | *Propionibacterium* | *Streptococcus* | *Staphylococcus* | *Corynebacterium* | Any of the 4 |
| 1P1 | 103 | 23.3 | 10.7 | 21.4 | 9.7 | 65.1 |
| 1P2 | 104 | 4.8 | 19.2 | 26.9 | 27.9 | 78.8 |

TABLE 4-continued

Presence of 16S rDNA from four genera found in the lesions from six patients with psoriasis, by lesion

| Sample | No. of Clones | Percent | | | | |
|---|---|---|---|---|---|---|
| | | *Propionibacterium* | *Streptococcus* | *Staphylococcus* | *Corynebacterium* | Any of the 4 |
| 2P1 | 99 | 0 | 2.0 | 16.2 | 3.0 | 21.2 |
| 2P2 | 100 | 3.0 | 2.0 | 27.0 | 8.0 | 40.0 |
| 2P3 | 100 | 1.0 | 3.0 | 28.0 | 15.0 | 47.0 |
| 3P1 | 102 | 2.0 | 0 | 2.0 | 74.5 | 78.5 |
| 3P2 | 98 | 0 | 45.9 | 1.0 | 1.0 | 47.9 |
| 4P1 | 100 | 0 | 52.0 | 3.0 | 0 | 55.0 |
| 4P2 | 104 | 0 | 11.5 | 8.7 | 3.8 | 24.0 |
| 6P1 | 102 | 1.0 | 12.7 | 17.6 | 5.9 | 37.2 |
| 6P2 | 101 | 1.0 | 11.9 | 53.5 | 5.0 | 71.4 |
| 8P1 | 101 | 0 | 3.0 | 36.6 | 46.5 | 86.1 |
| 8P2 | 100 | 0 | 13.0 | 2.0 | 79.0 | 94.0 |
| Mean ± SD | 101.1 ± 1.8 | 2.8 ± 6.3 | 14.4 ± 16.4 | 18.8 ± 15.8 | 21.5 ± 27.7 | 57.5 ± 23.6 |

The presence of 16S rDNA from five species found in samples of normal skin from healthy persons and from samples from patients with psoriasis is shown in Table 5.

TABLE 5

Presence of 16S rDNA from five species found in samples of normal skin from healthy persons and from patients with psoriasis

| Sample | No. of Clones | Percent | | | | | |
|---|---|---|---|---|---|---|---|
| | | Pa[a] | Ct[b] | Sh[c] | Sm[d] | Se[e] | Any of the 5 |
| AL | 105 | 17.1 | 0 | 0 | 0 | 0 | 17.1 |
| AR | 103 | 3.9 | 2.9 | 1.0 | 3.9 | 0 | 11.7 |
| BL | 103 | 14.6 | 2.9 | 1.0 | 4.9 | 0 | 23.4 |
| BR | 101 | 9.9 | 0 | 0 | 5.9 | 1.0 | 16.8 |
| CL | 103 | 12.6 | 8.7 | 2.9 | 0 | 1.9 | 26.1 |
| CR | 99 | 12.1 | 10.1 | 2.0 | 1.0 | 8.1 | 33.3 |
| DL | 101 | 11.9 | 14.9 | 4.0 | 1.0 | 0 | 31.8 |
| DR | 103 | 15.5 | 13.6 | 1.9 | 0 | 10.7 | 41.7 |
| EL | 100 | 32.0 | 5.0 | 0 | 1.0 | 1.0 | 39.0 |
| ER | 103 | 9.7 | 5.8 | 0 | 10.7 | 2.9 | 29.1 |
| FL | 102 | 45.1 | 7.8 | 5.9 | 2.9 | 6.9 | 68.6 |
| FR | 98 | 65.3 | 5.1 | 1.9 | 1.0 | 3.1 | 76.4 |
| AL2 | 100 | 0 | 0 | 0 | 0 | 0 | 0 |
| AR2 | 103 | 3.9 | 0 | 1.9 | 0 | 1.0 | 6.8 |
| CL2 | 101 | 53.5 | 0 | 0 | 9.9 | 0 | 63.4 |
| CR2 | 105 | 22.9 | 1.0 | 1.0 | 23.8 | 0 | 48.7 |
| EL2 | 103 | 6.8 | 0 | 0 | 6.8 | 0 | 13.6 |
| ER2 | 99 | 12.1 | 5.1 | 0 | 5.1 | 1.0 | 23.3 |
| FL2 | 102 | 23.5 | 7.8 | 6.9 | 0 | 3.9 | 42.1 |
| FR2 | 104 | 32.7 | 12.5 | 1.0 | 0 | 3.8 | 50.0 |
| Mean ± SD | 101.9 ± 2.0 | 20.3 ± 17.4 | 5.2 ± 4.9 | 1.6 ± 2.0 | 3.9 ± 5.8 | 2.3 ± 3.1 | 33.1 ± 20.7 |
| 1PN | 102 | 4.9 | 20.6 | 7.8 | 2.0 | 2.0 | 37.3 |
| 2PN | 100 | 0 | 1.0 | 9.0 | 0 | 15.0 | 25.0 |
| 3PN | 103 | 52.4 | 12.6 | 0 | 1.0 | 0 | 66.0 |
| 4PN | 102 | 1.0 | 1.0 | 22.5 | 2.0 | 1.0 | 27.5 |
| 6PN | 103 | 11.7 | 7.8 | 15.5 | 1.0 | 1.9 | 37.9 |
| 8PN | 101 | 0 | 26.7 | 0 | 1.0 | 0 | 27.7 |
| Mean ± SD | 101.8 ± 1.2 | 11.7 ± 20.4 | 11.6 ± 10.5 | 9.1 ± 8.8 | 1.2 ± 0.8 | 3.3 ± 5.8 | 36.9 ± 15.2 |
| Mean ± SD | 101.9 ± 1.8 | 18.3 ± 18.1 | 6.7 ± 6.9 | 3.3 ± 5.4 | 3.3 ± 5.2 | 2.5 ± 3.8 | 34.1 ± 19.4 |

[a] *Propionibacterium acnes*
[b] *Corynebacterium tuberculostearicum*
[c] *Staphylococcus hominis*
[d] *Streptococcus mitis*
[e] *Staphylococcus epidermidis*

Summary of Results

The microbial biota of the normal and psoriatic skin were compared using broad-range 16S rDNA PCR for archaea and bacteria. From 6 patients, 19 cutaneous samples were obtained, of which 13 were from diseased skin and 6 from the normal skin. From each sample, approximately 100 cloned PCR products were analyzed. Using 98% sequence identity as a species boundary, 1,841 (95.6%) clones were similar to known bacterial 16S rDNA, representing 6 phyla, 86 genera, or 189 species-level operational taxonomic units (SLOTUs); 84 (4.4%) clones were <98% identical to known 16S rDNA, probably representing novel species. No archaeal 16S rDNA were detected. Firmicutes was the most abundant and diversified phylum representing 38.3% of the SLOTUs and 46.0% of the clones from psoriatic skin, compared with 34.7% of the SLOTUs and 38.8% of the clones from the normal skin. The psoriatic skin samples showed 19.6±6.4 genera, significantly more than detected in normal skin samples (11.5±3.9) (P=0.008). The samples from psoriatic lesions yielded 52 new genera not observed in normal skin samples. These results show that psoriasis is associated with substantial alteration of the cutaneous bacterial biota.

Phylogenetic Analysis.

The 16S clone libraries from the six patients with psoriasis yielded 1,314 and 611 sequences for the lesions and normal skin samples, respectively. According to the RDP-II database, these could be grouped to 8 phyla, 94 genera, and 212 species-level operational taxonomic units (SLOTUs) at 98% identity. In total, 1,841 cloned sequences were similar to those of known bacterial isolates, and represented 189 SLOTUs. A total of 84 (4.4%) clones were <98% identical to current GenBank entries, and these clones were grouped into 5 phyla, 16 genera, and 23 novel phylotypes. In 20 skin samples from 6 healthy subjects, the inventors previously detected 247 SLOTUs, which belonged in 10 phyla (Gao, 2007, PNAS). The number of species per skin sample was not significantly different between the healthy subjects and those with psoriasis. A single representative of one additional bacterial phylum, Planctomycetes, was detected in one sample from a patient with psoriasis. Planctomycetes, a phylum comprised of aquatic bacteria, is found in fresh, brackish, and marine water samples. Overall, the bacteria detected from the 39 human skin specimens from this and the prior studies comprise 366 different SLOTUs.

Distribution at the Phylum Level.

Figure 4:
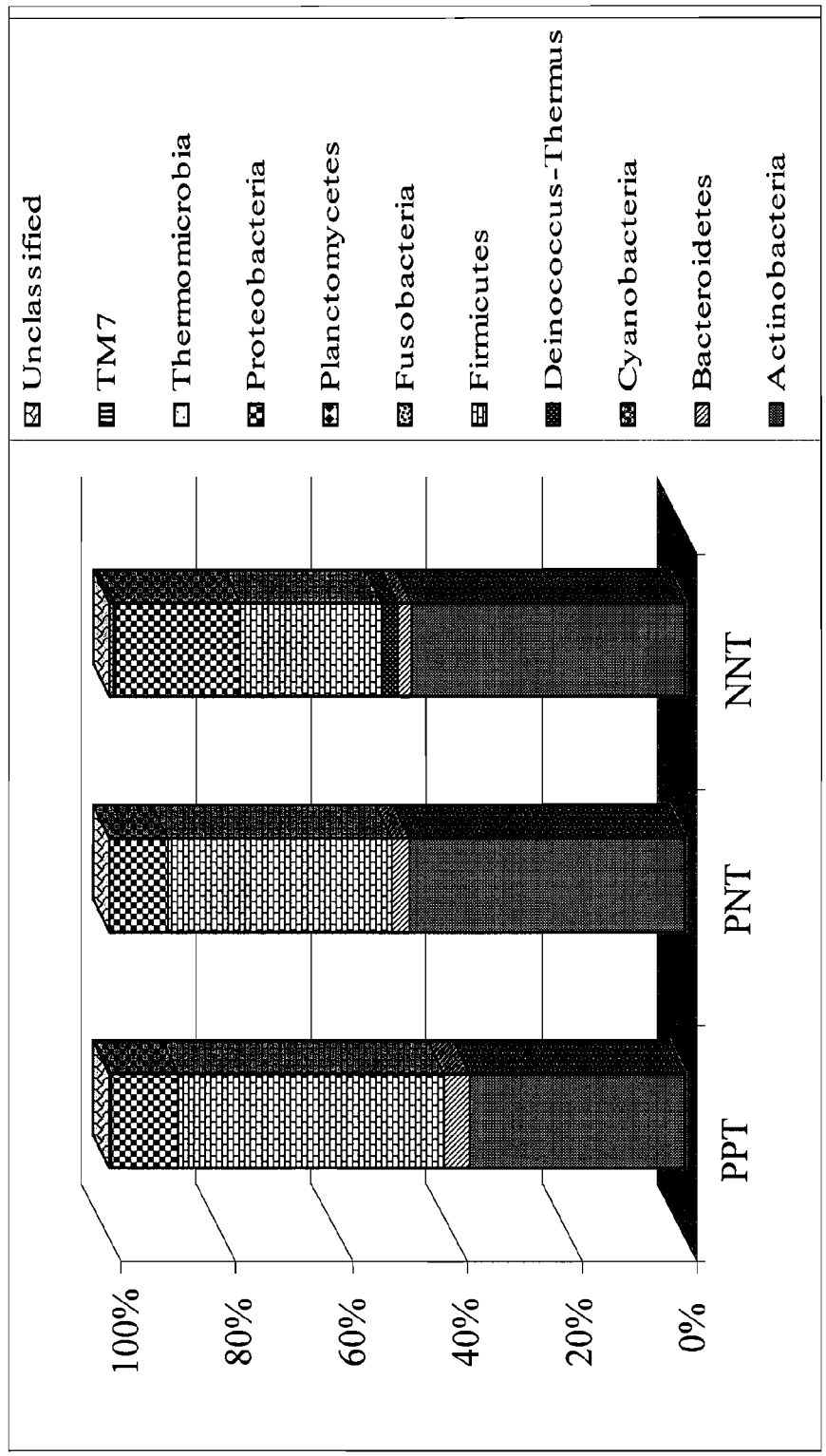
FIG. 4 shows the distribution of 3,963 16S rDNA clones from normal and psoriatic samples, by phylum.

The distribution of bacterial phyla was determined in samples of healthy and diseased skin. Firmicutes and Actinobacteria, the dominant phyla in both groups, were found in each sample, as shown in FIG. 4. Five other phyla (Proteobacteria, Bacteroidetes, Fusobacteria, Planctomycetes and TM7) were found in the samples from diseased skin. The most numerous and diverse phylum populating the psoriatic lesions was Firmicutes (46.0%), significantly (P<0.001) overrepresented compared to the samples from healthy persons. In contrast, Actinobacteria, the most prevalent (48.0%) and diverse phylum in the samples from normal skin of the patients, was significantly (P<0.001) lower (37.4%) in the samples from psoriatic lesions.

TABLE 6

The five most common species found in different groups of skin specimens.

| | Percent of total clones (rank)[e] | | | |
|---|---|---|---|---|
| Species | NNT1[a] | NNT2[b] | PNT[c] | PPT[d] |
| Propionibacterium acnes | 20.6(1) | 19.5(1) | 11.8(1) | 2.5(7) |
| Corynebacterium tuberculostearicum | 6.4(2) | 3.3(6) | 11.6(2) | 11.4(1) |
| Staphylococcus hominis | 1.6(12) | 1.3(11) | 9.2(4) | 9.1(2) |
| Streptococcus mitis | 2.7(6) | 5.8(3) | 1.1(15) | 5.6(3) |
| Enhydrobacter aerosaccus | 2.8(5) | 12.5(2) | 0.2(58) | 0.8(32) |
| Staphylococcus capitis | 1.0(20) | 0.6(29) | 11.5(3) | 1.1(19) |
| Staphylococcus caprae | 3.5(3) | 2.1(9) | 2.9(7) | 1.8(11) |
| Staphylococcus epidermidis | 2.9(4) | 1.2(12) | 3.3(6) | 2.2(9) |
| Corynebacterium simulans | 0.7(31) | 0.2(51) | 4.4(5) | 3.4(4) |
| Dermacoccus AF409025 | 0.1(116) | 5.8(3) | 0 | 1.4(17) |
| Rothia mucilaginosa | 1.5(15) | 0.2(51) | 0.3(40) | 3.0(5) |
| Staphylococcus haemolyticus | 0.2(81) | 3.5(5) | 1.1(15) | 0.4(51) |
| Five most common species | 36.2 | 47.1 | 48.5 | 32.5 |

[a]NNT1: 12 samples from six healthy persons, reported in a prior study (Gao Z. et al., PNAS, 2007).
[b]NNT2: Eight samples from four of six healthy people 8-10 months later.
[c]PNT: Six samples from normal skin of six patients with psoriasis.
[d]PPT: 13 samples from psoriatic lesions from six patients with psoriasis.
[e]Bold indicates most common 5 bacterial species; number in parentheses indicates rank order of that species in the samples.

TABLE 7

The 10 most common genera detected in human skin samples.

| | Percent of clones (%) | | | |
|---|---|---|---|---|
| | Normal subjects[a] | | Psoriatic subjects | |
| Genus | Time 1 (n = 1,221)[a] | Time 2 (n = 817) | Normal (n = 611) | Lesions (n = 1314)[b] |
| Corynebacterium | 19.0 | 7.2 | 29.1 | 21.2 |
| Staphylococcus | 11.1 | 10.5 | 31.8 | 18.1 |
| Propionibacterium | 22.0 | 19.7 | 12.4 | 2.8 |
| Streptococcus | 5.8 | 11.6 | 3.4 | 14.3 |
| Enhydrobacter | 2.8 | 12.5 | 0.2 | 0.8 |
| Acinetobacter | 3.7 | 3.8 | 1.0 | 1.6 |
| Dermacoccus | 0.8 | 6.2 | 0 | 1.4 |
| Pseudomonas | 2.7 | 1.0 | 2.5 | 1.4 |
| Rothia | 1.8 | 0.4 | 0.5 | 3.7 |
| Micrococcus | 0.5 | 2.7 | 0.2 | 2.2 |
| Percent | 70.2 | 75.6 | 81.1 | 67.5 |

[a]From (Gao Z., et al., Proc. Natl. Acad. Sci. U.S.A)
[b]Number of clones studied.

Distribution at the Genus Level.

In total, 166 genera were detected in the 39 samples from human skin. The data in Table 6 and Table 7 include the frequency of 10 of the most common genera in healthy and diseased samples. Only 20 genera were found in all 4 groups of specimens (NNT1, NNT2, PNT and PPT), but none of the genera was found in every sample. Corynebacterium, Staphylococcus, Streptococcus, and Propionibacterium were the four dominant genera in the samples from both normal skin and from the lesions of patients with psoriasis, accounting for 76.7% and 57.5% of all clones, respectively. Clones representing the genus Streptococcus were detected significantly more frequently (15.2±10.4%) from psoriatic lesion samples (p<0.05) than from the uninvolved skin samples of the patients (3.4±2.5%). In contrast, Propionibacterium species represented 21.1±18.2% of the total clones in the samples from the healthy subjects, significantly higher than in lesions from patients with psoriasis (2.9±5.5%) (P<0.05). For the patients with psoriasis, clones representing *Propionibacterium* were detected more frequently in samples from healthy skin (12.3±21.6%) than from lesions (2.9±5.5%), but the difference was not significant (P=0.33).

Distribution at the SLOTU Level.

Table 6 also shows the four most prevalent bacterial species in each of the different groups, accounting for 29.6~44.0% of the total clones in that group. *Propionibacterium acnes* was the most prevalent species in the samples from the healthy subjects and from the unaffected skin of the patients with psoriasis (also shown in FIG. 3A and Table 4). Representation of *P. acnes* was much lower in the samples from the lesions of the patients with psoriasis than in the samples from normal persons (P<0.05); the normal skin from psoriasis patients showed intermediate levels (12.3±21.6%). *Staphylococcus aureus*, long regarded as being associated with psoriasis (Skov L, & Baadsgaard O., 2000) was found in only 1.1% and 2.8% of the clones from the unaffected and diseased samples of the patients, respectively.

Analysis of Clustering.

39 samples of 16S rDNA clone library profiles from human skin were compared by using Unifrac distance metric. The results showed that the samples from same person had a tendency to cluster closer than samples from different individuals.

Double Principal Coordinate Analysis (DPCoA) of the Samples from Human Skin.

Similarities in SLOTU distributions between skin samples were evaluated using DPCoA. Four hypotheses concerning the grouping of samples were tested. First, analysis using all 39 samples of human skin from 12 persons (6 healthy persons and 6 patients with psoriasis) showed that those from the same subject were more similar to each other than to samples from other subjects (P<0.001). The same result was confirmed for the newly analyzed 19 samples from the six patients with psoriasis (P=0.006). Second, in analysis of the 19 samples from the patients with psoriasis, those obtained from psoriatic lesions were not significantly different than those from unaffected skin from the same patient, although these was an overall trend (P=0.062). Third, the samples of diseased skin from the patients (n=13) were clustered together, compared to samples of normal skin from healthy subjects (n=20) (P=0.001). Fourth, the samples obtained from unaffected skin from the patients (n=6) were not significantly different from those from normal skin of healthy subjects (n=20) (P=0.12).

Additional Quantitations with a Universal Probe in Combination with a Genus-Specific Probe for *Propionibacterium* sp.

Methods: A universal probe (G-16) (ACTGCTGCCTC-CCGTA) (SEQ ID NO:5) for quantitation of all bacteria and a genus-specific probe (Pro-17) (AAGTCAACCCGTATC-GAAAG) (SEQ ID NO:6) for *Propionibacterium* sp. were designed, targeting eubacterial 16S rDNA. qPCR reactions were performed using universal primers that can amplify an ~1500 bp fragment. Serial dilution of cloned PCR products was used to build standard curves. The method was evaluated for the specificity of the probe and quantification of bacteria in samples from healthy persons. Results: The Pro-17 genus-specific probe recognized cloned DNA representing 4 species within the genus *Propionibacterium* that had been previously detected in human skin, but not other common skin genera, including *Streptococcus, Staphylococcus, Corynebacterium, Rothia, Micrococcus, Kocuria,* or *Gemella* sp. Based on standard curves, as few as $10^2$ genomes per reaction were detected. Examination of two samples showed ~$10^3$-$10^4$ total bacterial genomes/swabbed area.

Conclusion: The qPCR assay is a reproducible, sensitive, rapid, and reliable method for the detection and relative quantitation of bacteria that populate human skin.

Table 8. Most common genera detected in normal human skin samples compared with those detected in psoriatic lesions and normal skin from psoriatic patients.

Using analysis of ribosomal genes from clone libraries, provided initial evidence that four genera, *Corynebacterium, Streptococcus, Staphylococcus,* and *Propionibacterium*, were most common in normal human skin, with significant differences in their prevalences in samples from healthy subjects, the normal skin of patients with psoriasis and the psoriatic lesions from the same patients (Table 8).

TABLE 8

|  | Percent of clones (%) | | |
|---|---|---|---|
|  | Psoriatic subjects | | Normal[b] |
| Genus | Lesions (n = 1.314)[a] | Normal (n = 611) | subjects (n = 1,221) |
| *Propionibacterium* | 2.8 | 12.4 | 22.0 |
| *Streptococcus* | 14.3 | 3.4 | 5.8 |
| *Corynebacterium* | 21.2 | 29.1 | 19.0 |
| *Staphylococcus* | 18.1 | 31.8 | 11.1 |
| Percent | 57.5 | 76.8 | 57.9 |

[a]Number of clones studied
[b]From (Gao Z., et al., Proc. Natl. Acad. Sci. U.S.A., 2007; 104, 2927-32.)

Certain embodiments of the present invention relate to a system for detecting and accurately quantifying the total population size of bacteria and genera *Corynebacterium, Streptococcus, Staphylococcus* and *Propionibacterium* sp. in skin samples using qPCR.

Methods

Using a computer algorithm for generating and estimating the phylogenetic range of 16S rRNA oligonucleotide probes in conjunction with the RDP-II database (PRIMROSE software package 1.1.7), the 16S rDNA sequences were scanned for conserved regions. A universal probe (G-16) (SEQ ID NO:5) for quantitation of all bacteria and a genus-specific probe (Pro-17) (SEQ ID NO:6) for *Propionibacterium* sp. were designed, targeting eubacterial 16S rDNA. qPCR reactions were performed using universal primers 8F (SEQ ID NO:1) and 1510R (SEQ ID NO:2) that can amplify an ~1500 bp fragment. Serial dilution of cloned 16S rDNA PCR products was used to build standard curves. The method was evaluated for the specificity of the probe and quantification of bacteria in samples from healthy persons.

Results

Comparison of Two Bacterial Universal Probes by q-PCR

To increase the sensitivity of quantification of q-PCR, two universal probes were compared, based on Blast search in the RDP (Table 9A-B) and by q-PCR (Table 10). The probes G16 (SEQ ID NO:5) and Probe 1 (ACTGAGACACGGTCCA) (SEQ ID NO:7) were tested separately with their respective serial qPCR standard dilution series and two PCR products from human skin. The PCR efficiency was equally high for both independent assays (between 90% and 100%).

TABLE 9A

Sensitivity of two universal probes (Probe 1 and G-16) for detection of bacterial species potentially found on human skin, based on RDP-II Percent of sequences with DNA identity to probe

| Probe designation | Eubacteria (n = 273,300) | Deinococcus-Thermus (n = 615) | Thermo-microbia n = 17 | Cyano-bacteria (n = 8,110) | Proteo-bacteria (n = 110,992) |
|---|---|---|---|---|---|
| Probe1[a] | 18.51 | 0 | 0 | 7.77 | 26.91 |
| G-16[b] | 71.85 | 86.18 | 11.76 | 53.08 | |

[a]ACTGAGACACGGTCCA (SEQ ID NO: 7) (Ott SJ. et al. J Clin Microbiol 2004; 42:2566-72).
[b]ACTGCTGCCTCCCTA (SEQ ID NO: 5).

TABLE 9B

Sensitivity of two universal probes (Probe 1 and G-16) for detection of bacterial species potentially found on human skin, based on RDP-II Percent of sequences with DNA identity to probe

| Probe designation | Firmicutes (n = 63,582) | Actino-bacteria (n = 26,307) | Plancto-mycetes (n = 2,569) | Bactero-idetes (n = 27,586) | Fuso-bacteria (n = 984) | TM7 (n = 389) |
|---|---|---|---|---|---|---|
| Probe1[a] | 11.37 | 0.71 | | 32.48 | 0.20 | 41.6 |
| G-16[b] | 81.70 | 80.27 | 1.01 | 78.64 | 90.24 | 75.0 |

[a]ACTGAGACACGGTCCA (SEQ ID NO: 7) (Ott SJ. et al. J Clink Microbiol. 2004; 42:2566-72).
[b]ACTGCTGCCTCCCGTA (SEQ ID NO: 5).

TABLE 10

Sensitivity of two universal probes for detection of bacterial species in the skin by q-PCR

| Samples | Given Copies (/ul) | G16 Ct | G16 Calc Copies | Probe 1 Ct | Probe 1 Calc Copies |
|---|---|---|---|---|---|
| Standard | 997,00,000 | 9.0 | 1,004,414,926 | 8.0 | 1,378,120,258 |
| Standard | 99,700,000 | 12.4 | 112,648,565 | 11.6 | 111,860,467 |
| Standard | 9,970,000 | 15.8 | 12,841,402 | 15.6 | 6,844,984 |
| Standard | 997,000 | 20.0 | 842,066 | 18.7 | 774,867 |
| Standard | 99,700 | 24.1 | 65,042 | 22.2 | 67,474 |
| Standard | 9,970 | 27.5 | 7,339 | 24.2 | 16,829 |
| Standard | 997 | 29.8 | 1,677 | 28.2 | 1,055 |
| MPL (unknown) | | 14.2 | 34,271,325 | 14.4 | 15,908,244 |
| MPLx0.1 (unknown) | | 18.2 | 2,807,271 | 18.0 | 1,293,676 |
| MPR (unknown) | | 15.7 | 13,380,869 | 16.5 | 3,657,015 |
| MPRx0.1 (unknown) | | 20.6 | 605,339 | 20.5 | 228,549 |
| Positive control | | 12.8 | 84,021,150 | 12.0 | 87,223,386 |
| No template control | | | | | |
| Negative control | | | | | |

Characteristics of the Probe G16 qPCR Assay

The 16S rDNA copies from 2 swab samples of skin were measured with this universal probe. The Ct (threshold cycle) values and the related cell numbers were determined by qPCR. The Ct value is the cycle when the fluorescence detected is significantly higher than the baseline value. The Ct value of each qPCR depends on the initial template amount (copy number) of the target sequence and is inversely proportional to the log of this copy number. As shown in Table 11, it was possible to determine the copy number of the tested samples from the standard curves (PCR efficiencies were >90%, R>0.99) using the probe G16. The lower qualitative detection limit was in the range of a few copies of the marker per reaction volume (RV) demonstrated by the fact that the standard containing 25 marker copies per RV was detectable. Based on standard curves, the probe could detect as few as 40 marker copies per reaction volume.

TABLE 11

The copies of 16S rDNA from 2 skin samples calculated by qPCR assays using probe 16G (SEQ ID NO: 5)

| Samples | Ct | Template Conc | Calc Conc | % Var |
|---|---|---|---|---|
| Standard | 6.5 | 250,200,000 | 377,123,533 | 50.7% |
| Standard | 9.4 | 25,020,000 | 52,628,711 | 110.3% |
| Standard | 14.2 | 2,502,000 | 2,124,093 | 15.1% |
| Standard | 20.1 | 250,200 | 40,708 | 83.7% |
| Standard | 23.6 | 2,502 | 3,802 | 52.0% |
| Standard | 27.8 | 250 | 229 | 8.5% |
| Standard | 30.3 | 25 | 41 | 64.2% |
| GR3 (Unknown) | 26.6 | | 494 | |
| GL3 (Unknown) | 22.8 | | 6,564 | |
| Positive Control | 25.9 | | 791 | |
| No template control | | | | |
| Negative control | | | | |

Sensitivity and Specificity of the Genus-Specific Probe (Pro-17) (SEQ ID NO:6)

The specificity of the *Propionibacterium* sp. probe was determined by comparing cloned 16S rDNA PCR products from *Propionibacterium* sp. (n=4) and other common skin genera (n=7), including *Streptococcus, Staphylococcus, Corynebacterium, Rothia, Gemella, Micrococcus*, and *Kocuria* species. For sensitivity assays, serial dilution of cloned 16S rDNA PCR products from *Propionibacterium acnes* was used to build standard curves for enumeration of unknown samples. The results showed that the Pro-17 genus-specific probe (SEQ ID NO:6) recognized cloned DNA representing 4 species within the genus *Propionibacterium* that had been previously detected in human skin, but not seven other common skin genera tested. A standard curve (PCR efficiencies were 87%, R>0.99) was created by 10-fold dilutions of 16S rDNA PCR products with genus-specific probe Pro-17 (SEQ ID NO:6).

Detection Using the All-Bacteria Probe and *Propionibacterium* Species Probe from Skin Swabs.

In order to test the performance of the q-PCR assay on clinical samples, 4 skin swabs were collected from one healthy person. All samples were positive for the all-bacteria probe and for *Propionibacterium* species, indicating that qPCR can be performed on clinical samples following a rapid and inexpensive DNA extraction procedure. These results are shown in Table 12.

TABLE 12

Quantitation of all-bacteria species and *Propionibacterium* sp. from four skin swabs

| | All-bacteria species | | *Propionibacterium* species | |
|---|---|---|---|---|
| Samples | Ct | Number of copies | Ct | Number of copies |
| GR | 26.6 | 37,099 | 39.6 | 24 |
| GL | 28.6 | 11,541 | 36.1 | 107 |
| GRN | 27.8 | 17,728 | 34.5 | 210 |
| GLN | 25.5 | 69,415 | 38.6 | 31 |

Conclusions:

1. The qPCR assay is a sensitive, rapid, and reliable method for the detection and relative quantitation of bacteria that populate human skin.
2. Universal probe 16G (SEQ ID NO:5) is more sensitive to detect the bacteria found in human skin than Probe 1 (SEQ ID NO:7).
3. The q-PCR assays using a genus-specific probe allow detection of all known *Propionibacterium* sp. that are found in the skin samples.
4. The probe is specific to the genus *Propionibacterium* sp; no significant cross-reaction of the genus-specific probe among the different common genera was seen.
5. Based on standard curves, as few as $4 \times 10^1$ genomes per reaction volume could be detected. Examination of the samples from skin swabs showed $\sim 10^3$-$10^5$ total bacterial and $\sim 10^1$-$10^2$ *Propionibacterium* sp. 16S rDNA copies/swabbed area.

Design of Additional Genus-Specific Probes in Combination with New Universal 16S rDNA Probe.

A new universal 16S rDNA probe for quantitation of all eubacterial and two new genus-specific probes (*Propionibacterium* and *Streptococcus* sp.) were designed. qPCR reactions were performed using universal primers that can amplify an ~800 bp rDNA fragment and the genus-specific probes were combined in multiplex reactions. The method was evaluated for the specificity of the probes and quantitation of bacteria in samples from one healthy person and one patient with psoriasis (uninvolved skin and psoriatic lesions). The genus-specific probes were shown to be sensitive and specific using cloned DNA representing species from genera previously detected in human skin. Each of the tested human specimens yielded positive results with the universal eubacterial probe and both genus-specific probes.

Three samples of healthy skin showed *Streptococcus* to *Propionibacterium* ratios of 0.001 to 0.011 (median 0.004), whereas three samples from the psoriasis lesions showed 0.160~2.000 (median 0.646). These results demonstrated that the qPCR assay is a sensitive, rapid, and reliable method for the detection and relative quantitation of bacteria that populate human skin. *Propionibacterium* sp. appears to predominate in samples from healthy skin, but was substantially underrepresented in the samples from psoriasis lesions.

The results described herein show the development of a system to accurately quantify the total population size of bacteria and the ratio of *Streptococcus* to *Propionibacterium* in skin samples from healthy persons and patients with psoriasis using quantitative real-time-PCR (qPCR).

Methods

Using a computer algorithm for generating and estimating the phylogenetic range of 16S rRNA oligonucleotide probes in conjunction with the RDP-II database (PRIMROSE software package 1.1.7), ten 16S rDNA sequences belonging to different phyla were scanned for conserved regions.

A universal probe (G-16) (SEQ ID NO:5) for quantitation of all eubacteria and the genus-specific probes for *Propionibacterium* sp. (SEQ ID NO:6) and for *Streptococcus* sp. (AG-ATGGACCTGCGTTGT) (SEQ ID NO:8) were designed, targeting the specific eubacterial 16S rDNA. qPCR reactions were performed using universal primers (8F, SEQ ID NO:1) and U785R, (GGACTACCVGGGTATCTAAKCC) (SEQ ID NO:9) that can amplify an ~800 bp fragment from a large fraction of all eubacteria. Serial dilution of a mixture of equal amounts of 16S rDNA copies from *Propionibacterium acnes* and *Streptococcus mitis* genomic DNA were used to build standard curves.

Results

Standard Curves of the qPCR Assays

A bacterial universal probe (SEQ ID NO:5) and two genus-specific dual-labeled probes (SEQ ID NO:6 and SEQ ID NO:7) were used to detect and quantify all eubacteria and *Propionibacterium* sp. and *Streptococcus* sp. from human skin samples. The probe is TaqMan-minor groove binder (MGB) probe (Applied Biosystems, Foster City, Calif., USA) labeled with FAM fluorescent dye or VIC fluorescent dye.

A 10-fold dilution of a mix of equal amounts of 16S rDNA copies from *Propionibacterium acnes* and *Streptococcus mitis* genomic DNA was used to build standard curves. The Ct (threshold cycle) values and the related cell numbers were determined by qPCR. The Ct value is the cycle when the fluorescence detected is significantly higher than the baseline value. The Ct value of each qPCR depends on the initial template amount (copy number) of the target sequence and is inversely proportional to the log of this copy number. It was possible to determine the copy number of the tested samples from the standard curves (PCR efficiencies were >90%, R>0.99) using probe G16 (SEQ ID NO:5) (Table 13). The lower qualitative detection limit was in the range of a few copies of the marker per reaction volume (RV), demonstrated by the fact that the standard containing 25 marker copies per RV was detectable. Based on standard curves, the probe was calculated to detect as few as 40 marker copies per reaction volume.

For qPCR, 1 μl of DNA sample was added to a 25 ul PCR reaction containing 2.5 μl 10×PCR buffer (QIAGEN, Valencia, Calif.), 1.5 mM $MgCl_2$, 200 μM each dNTP, 10 pmol of each primer, 5 pmol of each probe, and 1.25 units of Taq polymerase. The PCR reaction was run in a Rotor-Gene 3000 (Corbett Life Science) with an initial hold at 50° C. for 2 minutes, then 95° C. for 5 minutes, followed by 45 cycles of 95° C. for 10 sec, 52° C. for 60 sec, and 72° C. for 90 sec. During the 52° C. steps, the Rotor-Gene stimulates the samples and then acquires fluorescence data on channels appropriate to 6-FAM and JOE/VIC.

TABLE 13

Copies of total 16S rDNA from two unknown skin samples calculated by qPCR assays using probe 16G (SEQ ID NO: 5)

| Samples | Ct[a] | Concentrations | | % Variation |
|---|---|---|---|---|
| | | Template | Calculated | |
| Standard | 6.5 | $2.5 \times 10^8$ | 377,123,533 | 50.7 |
| Standard | 9.4 | $2.5 \times 10^7$ | 52,628,711 | 110.3 |
| Standard | 14.2 | $2.5 \times 10^6$ | 2,124,093 | 15.1 |
| Standard | 20.1 | $2.5 \times 10^5$ | 40,708 | 83.7 |
| Standard | 23.6 | $2.5 \times 10^3$ | 3,802 | 52.0 |
| Standard | 27.8 | $2.5 \times 10^2$ | 229 | 8.5 |
| Standard | 30.3 | $2.5 \times 10^1$ | 41 | 64.2 |
| GR3 (Unknown) | 26.6 | | 494 | |
| GL3 (Unknown) | 22.8 | | 6,564 | |
| Positive Control | 25.9 | | 791 | |
| No template | | | $0^b$ | |

TABLE 13-continued

Copies of total 16S rDNA from two unknown skin samples calculated by qPCR assays using probe 16G (SEQ ID NO: 5)

| Samples | Ct[a] | Concentrations | | % Variation |
|---|---|---|---|---|
| | | Template | Calculated | |
| control | | | | |
| Negative control | | | $0^b$ | |

[a]CT represents the number of PCR cycles calculated to reach the threshold for positivity.
[b]Below the lowest level of detection.

Sensitivity and Specificity of the Genus-Specific Probes

Figure 5:
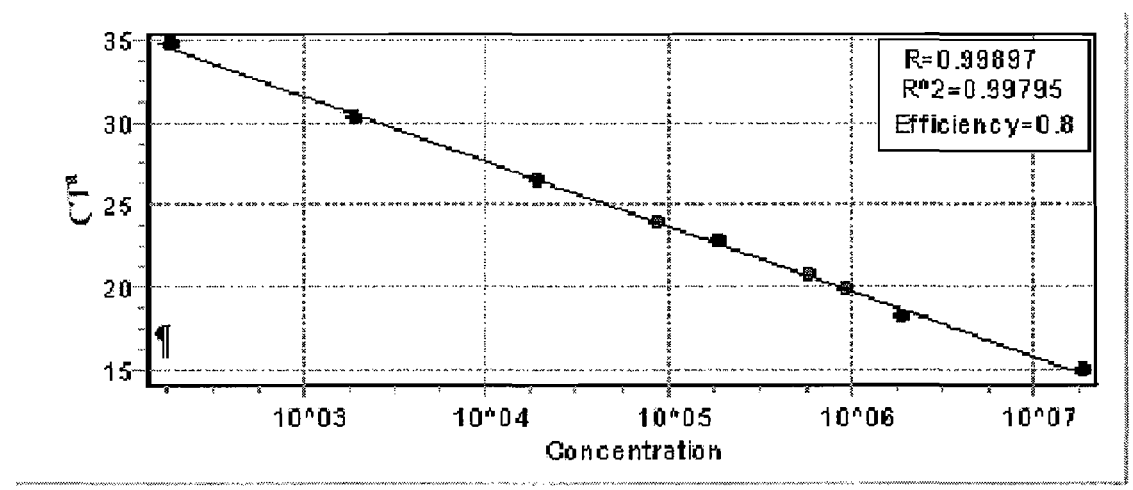
FIG. 5 shows the standard curve with the *Streptococcus* genus probe (SEQ ID NO:8) using cloned 16S rDNA.

The specificity of the two probes (SEQ ID NO:6 and SEQ ID NO:8) were determined by comparing cloned 16S rDNA PCR products from *Propionibacterium* sp. (n=4), *Streptococcus* sp. (n=2) and other common skin genera 16S rDNA PCR products, including *Staphylococcus, Corynebacterium, Rothia, Gemella, Micrococcus,* and *Kocuria* species. The genus-specific probes recognized the cloned DNA representing species within the same genera that had been previously detected in human skin, but not other common skin genera. The sensitivity of the assays was assessed using 10-fold dilutions of the same templates used for the standard curves, corresponding to $3 \times 10^6$ through $3 \times 10^1$ 16S rDNA copies per reaction. The limit of detection for the two genus-specific probes ranged from $10^1$ to $10^2$ 16S rDNA copies per reaction. FIG. 5 shows the standard curve created by 10-fold dilutions of 16S rDNA copies with the genus-specific *Streptococcus* probe (SEQ ID NO:8). The probe performed well, with R>0.99 and PCR efficiencies of 80%.

Comparison of the qPCR Result in Single and Multiplex Format

To determine whether the two genus-specific probes could be used in multiplex reactions, the detection of 16S rDNA copies from *Propionibacterium acnes* and *Streptococcus mitis* genomic DNA was compared in single and multiplex formats. No significant differences were found when the two genus-specific probes were tested in multiplex compared with the single formats (FIG. 6).

Detection of All Eubacteria and *Propionibacterium* sp. and *Streptococcus* sp. from Skin Swabs.

To test the performance of the q-PCR assay on clinical samples, six skin swabs were collected from a healthy person (n=2) and one person with psoriasis (n=4). All samples yielded positive results for the all-eubacterial probe and the two genus-specific probes for *Propionibacterium* and *Streptococcus* species. The results (Table 14) show that qPCR can be performed on clinical samples across broad range of DNA concentrations, following a rapid and inexpensive DNA extraction procedure. Three samples of healthy skin showed *Streptococcus* to *Propionibacterium* ratios ranging from 0.001 to 0.011 (median 0.004), whereas 3 samples from psoriasis lesions showed 0.160~2.000 (median 0.646) (p=0.23; Student's t-test).

TABLE 14

Quantitation of all eubacterial species, and *Streptococcus* and *Propionibacterium* species from six skin swabs

| Code | Condition | All eubacteria | *Streptococcus* | *Propionibacterium* | Ratio of S/P |
|---|---|---|---|---|---|
| AL4 | Healthy | $7.4 \times 10^9$ | 132,204 | 33,799,641 | 0.004 |
| AR4 | Healthy | $1.9 \times 10^9$ | 104,525 | 120,990,902 | 0.001 |
| 10PN | Uninvolved | $3.1 \times 10^4$ | 68 | 6,245 | 0.011 |
| 10P1 | Lesion | $3.9 \times 10^4$ | 705 | 1,091 | 0.646 |
| 10P2 | Lesion | $5.7 \times 10^9$ | 18 | 9 | 2.000 |
| 10P3 | Lesion | $1.8 \times 10^5$ | 609 | 3,721 | 0.160 |

Conclusions

1. The qPCR assay is a sensitive, rapid, and reliable method for the detection and relative quantitation of bacteria that populate human skin.

2. The genus-specific probes (SEQ ID NO:6 and SEQ ID NO:8) recognized cloned DNA representing species within the same genera that had been previously detected in human skin, but not other common skin genera.

3. Based on standard curves, as few as $4\times10^1$ genomes per reaction volume, using the all eubacteria universal probe (SEQ ID NO:5) could be detected.

4. *Propionibacterium* sp. appears to predominate in the samples from healthy skin, but was substantially underrepresented in the samples from psoriasis lesions.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

Patents, patent applications, publications, product descriptions, and protocols are cited throughout this application, the disclosures of which are incorporated herein by reference in their entireties for all purposes.

The invention claimed is:

1. A method for diagnosing psoriasis in a patient comprising:
   a. determining a ratio of a *Streptococcus* species to a *Propionibacterium* species (gS/P ratio) in a psoriatic skin lesion in the patient;
   b. determining a ratio of a *Streptococcus* species to a *Propionibacterium* species (gS/P ratio) in a healthy skin in the patient or in a skin of a healthy control;
   c. comparing the gS/P ratios in part a) and b); and
   d. diagnosing psoriasis in the patient if the gS/P ratio in part a. is raised as compared to part b.

2. The method of claim 1, wherein the determining comprises performing quantitative polymerase chain reaction (qPCR).

3. The method of claim 2, wherein amplified target DNA from the qPCR reaction is characterized by fluorescent emission detected by binding of one or more of a labeled probe selected from the group consisting of SEQ ID NO:5, SEQ ID NO:6 and SEQ ID NO:8 to the amplified target DNA.

4. The method of claim 1, wherein determining said gS/P ratio comprises determining a ratio of a non-Group A *Streptococcus* species (NGS) to a *Propionibacterium* species.

5. The method of claim 4, wherein said NGS is *Streptococcus mitis*.

6. The method of claim 4, wherein said *Propionibacterium* species is *Propionibacterium acnes*.

7. The method of claim 5, wherein said *Propionibacterium* species is *Propionibacterium acnes*.

* * * * *

UNITED STATES PATENT AND TRADEMARK OFFICE
CERTIFICATE OF CORRECTION

PATENT NO. : 7,919,250 B2
APPLICATION NO. : 12/183806
DATED : April 5, 2011
INVENTOR(S) : Martin J. Blaser et al.

Page 1 of 1

It is certified that error appears in the above-identified patent and that said Letters Patent is hereby corrected as shown below:

In the Specification

At Column 1, beginning in Line 12 and ending in Line 17 please replace:
"This invention was made in part in the course of research sponsored by the National Institutes of Health (NIH) Grant RO1 GM 63270; the Ellison Medical Foundation; Diane Belfer Program for Microbial Ecology; and a Bernard Levine Scholarship. The U.S. government may have certain rights in this invention."

With:
--This invention was made with government support under R01 GM063270 awarded by the National Institutes of Health. The government has certain rights in the invention.--

Signed and Sealed this
Twenty-first Day of October, 2025

John A. Squires
*Director of the United States Patent and Trademark Office*

SEQUENCE LISTING

```
<160> NUMBER OF SEQ ID NOS: 53

<210> SEQ ID NO 1
<211> LENGTH: 17
<212> TYPE: DNA
<213> ORGANISM: Artificial
<220> FEATURE:
<223> OTHER INFORMATION: Primer

<400> SEQUENCE: 1
gtttgatymt ggctcag                                                  17

<210> SEQ ID NO 2
<211> LENGTH: 22
<212> TYPE: DNA
<213> ORGANISM: Artificial
<220> FEATURE:
<223> OTHER INFORMATION: Primer

<400> SEQUENCE: 2
tacggytacc ttgttacgac tt                                            22

<210> SEQ ID NO 3
<211> LENGTH: 19
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (6)..(6)
<223> OTHER INFORMATION: n = i
<220> FEATURE:
<221> NAME/KEY: misc_feature
<222> LOCATION: (14)..(14)
<223> OTHER INFORMATION: n = i

<400> SEQUENCE: 3
cgacanccat gcancacct                                                19

<210> SEQ ID NO 4
<211> LENGTH: 1541
<212> TYPE: DNA
<213> ORGANISM: Escherichia coli

<400> SEQUENCE: 4
aaattgaaga gtttgatcat ggctcagatt gaacgctggc ggcaggccta acacatgcaa    60
gtcgaacggt aacaggaaga agcttgctct ttgctgacga gtggcggacg ggtgagtaat   120
gtctgggaaa ctgcctgatg gagggggata actactgaa acggtagcta ataccgcata    180
```

-continued

```
acgtcgcaag accaaagagg gggaccttcg ggcctcttgc catcggatgt gcccagatgg      240
gattagctag taggtggggt aacggctcac ctaggcgacg atccctagct ggtctgagag      300
gatgaccagc cacactggaa ctgagacacg gtccagactc ctacgggagg cagcagtggg      360
gaatattgca caatgggcgc aagcctgatg cagccatgcc gcgtgtatga agaaggcctt      420
cgggttgtaa agtactttca gcggggagga agggagtaaa gttaataccT ttgctcattg      480
acgttacccg cagaagaagc accggctaac tccgtgccag cagccgcggt aatacggagg      540
gtgcaagcgt taatcggaat tactgggcgt aaagcgcacg caggcggttt gttaagtcag      600
atgtgaaatc cccgggctca acctgggaac tgcatctgat actggcaagc ttgagtctcg      660 tagaggggggg tagaattcca ggtgtagcgg tgaaatgcgt agagatctgg aggaataccg      720
gtggcgaagg cggccccctg gacgaagact gacgctcagg tgcgaaagcg tggggagcaa      780
acaggattag ataccctggt agtccacgcc gtaaacgatg tcgacttgga ggttgtgccc      840
ttgaggcgtg gcttccggag ctaacgcgtt aagtcgaccg cctggggagt acggccgcaa      900
ggttaaaact caaatgaatt gacggggggcc cgcacaagcg gtggagcatg tggtttaatt      960
cgatgcaacg cgaagaacct tacctggtct tgacatccac ggaagttttc agagatgaga     1020
atgtgccttc gggaaccgtg agacaggtgc tgcatggctg tcgtcagctc gtgttgtgaa     1080
atgttgggtt aagtcccgca acgagcgcaa cccttatcct ttgttgccag cggtccggcc     1140
gggaactcaa aggagactgc cagtgataaa ctggaggaag gtggggatga cgtcaagtca     1200
tcatggccct tacgaccagg gctacacacg tgctacaatg gcgcatacaa agagaagcga     1260
cctcgcgaga gcaagcggac ctcataaagt gcgtcgtagt ccggattgga gtctgcaact     1320
cgactccatg aagtcggaat cgctagtaat cgtggatcag aatgccacgg tgaatacgtt     1380
cccgggcctt gtacacaccg cccgtcacac catgggagtg ggttgcaaaa gaagtaggta     1440
gcttaacctt cgggagggcg cttaccactt tgtgattcat gactggggtg aagtcgtaac     1500
aaggtaaccg tagggaacc tgcggttgga tcacctcctt a                          1541
```

<210> SEQ ID NO 5
<211> LENGTH: 16
<212> TYPE: DNA
<213> ORGANISM: Artificial
<220> FEATURE:
<223> OTHER INFORMATION: Probe

<400> SEQUENCE: 5
actgctgcct cccgta                                                      16

<210> SEQ ID NO 6
<211> LENGTH: 20
<212> TYPE: DNA
<213> ORGANISM: Artificial
<220> FEATURE:
<223> OTHER INFORMATION: Probe

<400> SEQUENCE: 6
aagtcaaccc gtatcgaaag                                                  20

<210> SEQ ID NO 7
<211> LENGTH: 16
<212> TYPE: DNA
<213> ORGANISM: Artificial
<220> FEATURE:
<223> OTHER INFORMATION: Probe

<400> SEQUENCE: 7
actgagacac ggtcca                                                  16

<210> SEQ ID NO 8
<211> LENGTH: 17
<212> TYPE: DNA
<213> ORGANISM: Artificial
<220> FEATURE:
<223> OTHER INFORMATION: Probe

<400> SEQUENCE: 8
agatggacct gcgttgt                                                 17

<210> SEQ ID NO 9
<211> LENGTH: 22
<212> TYPE: DNA
<213> ORGANISM: Artificial
<220> FEATURE:
<223> OTHER INFORMATION: Probe

<400> SEQUENCE: 9
ggactaccvg ggtatctaak cc                                           22

<210> SEQ ID NO 10
<211> LENGTH: 1474
<212> TYPE: DNA
<213> ORGANISM: Artificial
<220> FEATURE:
<223> OTHER INFORMATION: Uncultured Allisonella sp. clone BL34 16S
      ribosomal RNA gene, partial sequence

<400> SEQUENCE: 10
gaacgctggc ggcgtgctta acacatgcaa gtcgaacggg aagagatgaa gagcttgctc     60
tttatcgaat ccagtggcaa acgagtgagt aacacgtaaa caacctgcct tcaggatggg    120
gacaacagac ggaaacgact gctaataccg aatacgttcc acgggccgca tgacctgtgg    180
aagaaagggt agcctctacc tgtaagctat cgcctgaaga ggggtttgcg tctgattagg    240
cagttggtgg ggtaacggcc caccaaacca acgatcagta gccggtctga gaggatgaac    300
ggccacactg gaactgagac acggtccaga ctcctacggg aggcagcagt ggggaatctt    360
ccgcaatgga cgaaagtctg acggagcaac gccgcgtgag tgaagacggc cttcgggttg    420
taaagctctg tgatccggga cgaaagagcc tgaggttaat agcctaagga agtgacggta    480
ccggaaaagc aagccacggc taactacgtg ccagcagccg cggtaatacg taggtggcaa    540
gcgttgtccg gaattattgg gcgtaaagcg cgcgcaggcg gcttcctaag tccatcttaa    600
aagtgcgggg cttaaccccg tgatgggatg gaaactggga agctggagta tcggagagga    660
aagtggaatt cctagtgtag cggtgaaatg cgtagagatt aggaagaaca ccggtggcga    720
aggcgacttt ctggacgaaa actgacgctg aggcgcgaaa gcgtggggag caaacaggat    780
tagataccct ggtagtccac gccgtaaacg atggatacta ggtgtaggag gtatcgaccc    840
cttctgtgcc ggagttaacg caataagtat cccgcctggg aagtacgatc gcaagattaa    900
aactcaaagg aattgacggg ggcccgcaca agcggtggag tatgtggttt aattcgacgc    960
aacgcgaaga accttaccag gtcttgacat tgatcgcaat tttcagaaat gagaagttct   1020
ccttcgggag acgagaaaac aggtggtgca cggctgtcgt cagctcgtgt cgtgagatgt   1080
tgggttaagt cccgcaacga gcgcaacccc tatcatttgt tgccagcacg taaaggtggg   1140
gactcaaatg agaccgccgc agacaatgcg gaggaaggtg gggatgacgt caagtcatca   1200
tgccccttat gacctgggct acacacgtac tacaatgggt gtcaacaaag agaagcgaaa   1260
gggcgacctg gagccaacct caaaaacaca ctcccagttc agatcgcagg ctgcaactcg   1320

```
cctgcgtgaa gcaggaatcg ctagtaatcg cgggtcagca taccgcggtg aatacgttcc    1380
cgggccttgt acacaccgcc cgtcacacta tgagagtcag aaacacccga agccggtgag    1440
gtaaccgtaa ggagccagcc gtcgaaggcg gagc                                1474

<210> SEQ ID NO 11
<211> LENGTH: 1431
<212> TYPE: DNA
<213> ORGANISM: Artificial
<220> FEATURE:
<223> OTHER INFORMATION: Uncultured Anaerococcus sp. clone BL36 16S
      ribosomal RNA gene, partial sequence

<400> SEQUENCE: 11
taacgctggc ggcgtgcata acatgcaag tcgaacgatg aaacttaata gatttcttcg     60
gaatgacctt aagtgaatta gtggcgaacg ggtgagtaac gcgtgagtaa cctgccttac    120
acaagggata gcctctggaa acggagaata atacccctatg aaattacagc ctcgcatgaa  180
gcagtaatca aagtgttagc ggtgtaagat ggacttgcgt ctgattagct agttggtgag   240
ataacagccc accaaggcaa cgatcagtag ccggcttgag agagtgtacg gccacattgg   300
gactgagaca cggcccagac tcctacggga ggcagcagtg gggaattttg cacaatgggg   360
gcaaccctga tgcagcgacg ccgcgtgatt tagaaggcct tcgggttgta aaaatctttt   420
gtataggaag aagatgacag tactatacga ataaggtccg gctaattacg tgccagcagc   480
cgcggtaata cgtaaggacc gagcgttgtc cggaatcatt gggcgtaaag ggtacgtagg   540
cggttagaaa agttagaagt gaaaggctat agctcaacta tagtaagctt ttaaaactgt   600
ttaacttgag agatggaagg gaaagtgaaa ttcctagtgt agcggtgaaa tgcgcagata   660
ttaggaggaa taccggtggc gaaggcgact ttctggccat tatctgacgc tgaggtacga   720
aagcgtgggt agcaaacagg attagatacc ctggtagtcc acgccgtaaa cgatgagtgt   780
taggtgtctg gagtaaatct gggtgccgca gctaacgcaa taaacactcc gcctggggag   840
tacgcacgca agtgtgaaac tcaaaggaat tgacggggac ccgcacaagc agcggagcat   900
gtggtttaat tcgaagcaac gcgaagaacc ttaccaagtc ttgacatatt acggcgtgtt   960
ttagagataa gacactatat cttcggataa ctgtaataca ggtggtgcat ggttgtcgtc    1020
agctcgtgtc gtgagatgtt gggttaagtc ccataacgag cgcaacccct atggctagtt    1080
accatcatta agttggggac tctagcaata ctgccggtga caaaccggag gaaggtgggg    1140
atgacgtcaa atcatcatgc cctatatgac ttgggctaca cacgtgctac aatggcaggt   1200
acagagggcg gcgagacggt gacgtcaagc gaacctcaaa aagcctgtcc cagttcggat    1260
tgcactctgc aactcgagtg catgaagttg gagttgctag taatcgcaga tcagaatgct    1320
gcggtgaatg cgttcccggg tcttgtacac accgcccgtc acaccatgga agttggcaat   1380
acccgaagcc tgtgagcgaa ccattggacg cagcagtcga aggtagggtc a            1431

<210> SEQ ID NO 12
<211> LENGTH: 1439
<212> TYPE: DNA
<213> ORGANISM: Artificial
<220> FEATURE:
<223> OTHER INFORMATION: Uncultured Porphyromonas sp. clone BL41 16S
      ribosomal RNA gene, partial sequence

<400> SEQUENCE: 12
aacgctagcg attaggctta acacatgcaa gtcgcaaggt aacgtgttgg aagcttgcgt    60
tccgatgacg acgaccggcg gatgggtgcg taacgcgtat gcaacttgcc tcacagtgga    120
```

```
gaataacccg gagaaatccg gactaatgct ccatacactc ttaagtacgc ctgtacatga    180
gaggaaagat ttatcgctgt gagataggca tgcgtcctat taggtagttg gtgaggtaac    240
ggctcaccaa gccgacgata ggtaggggtg ctgagaggca gatcccccac attgggactg    300
agacacggcc caaactccta cgggaggcag cagtgaggaa tattggtcaa tggaggaaac    360
tctgaaccag ccaagtcgcg tgaaggaaga atgtcctaag gattgtaaac ttctttagcg    420
agcgagtaag gacttccacg tgttgggagt ttgaaagtag ctcgagaata agtatcggct    480
aactccgtgc cagcagccgc ggtaatacga aggatacgag cgttatccgg atttattggg    540
tttaaagggt gcgcaggtgg tcttgcaagt cagtggtgaa aagctgaggc tcaacctcag    600
ccttgccgtt gaaactgtaa gacttgagag tacatgatgt gggcggaatg cgtagtgtag    660
cggtgaaatg catagatatt acgcagaact ccgattgcga aggcagctca caaaggtatt    720
tctggcactg aggcacgaaa gcgtgggag  cgaacaggat tagataccct ggtagtccac    780
gccgtaaacg atgattactc gaagtatgcg atatgacagt atgcttccaa gcgaaagtga    840
taagtaatcc acctggggag tacgccggca acggtgaaac tcaaaggaat tgacggggc     900 ccgcacaagc ggaggaacat gtggtttaat tcgatgatac gcgaggaacc ttacccggga    960
ttgaaatgta tgtgagcctc ttgggaaacc gagagggttc tcttcggaga cacatatgta   1020
ggtgctgcat ggttgtcgtc agctcgtgcc gtgaggtgtc ggcttaagtg ccataacgag   1080
cgcaacccct atcgtcagtt actaacaggt gatgctgagg actctggcga gactgccgtc   1140
gtaaggcgag aggaaggtgg ggatgacgtc aaatcagcac ggcccttaca tccggggcga   1200
cacacgtgtt acaatggtag ggacagagag tagccactcg gtgacgagga gcggatcttg   1260
aaaccctatc tcagttcgga tcggagtctg caactcgact ccgtgaagcc ggattcgcta   1320
gtaatcgcgc atcagccgtg gcgcggtgaa tacgttcccg ggccttgtac acaccgcccg   1380
tcaagccatg gaagttgggg gtacctgaag tgcgtgaccg caaggagcgt ccgagggta    1439
```

<210> SEQ ID NO 13
<211> LENGTH: 1434
<212> TYPE: DNA
<213> ORGANISM: Artificial
<220> FEATURE:
<223> OTHER INFORMATION: Uncultured Prevotella sp. clone BL42 16S
      ribosomal RNA gene, partial sequence

<400> SEQUENCE: 13

```
aacgctagct acaggcttaa cacatgcaag tcgcaggtaa catgaggaaa gcttgctttc     60
cttgatgacg actggcgcac gggtgagtaa cgcgtatcca accttcccat aactacggga    120
taacccgttg aaagacggcc taataccgta tgatatcgtt tgctgacatc aaataacgat    180
taaaggttta gcggttatgg atggggatgc gtctgattag cttgttggcg gggtaacggc    240
ccaccaaggc tacgatcagt aggggttctg agaggaaggt cccccacatt ggaactgaga    300
cacggtccaa actcctacgg gaggcagcag tgaggaatat tggtcaatgg gcgagagcct    360
gaaccagcca gtagcgtgc aggatgacgg ccctatgggt tgtaaactgc ttttatgtgg    420
ggataaagtg cgtgacgtgt catgcattgc aggtaccaca tgaataagga ccggctaatt    480
ccgtgccagc agccgcggta atacggaagg tccgggcgtt atccggattt attgggttta    540
aagggagcgt aggctgtcta ttaagcgtgt tgtgaaattt accggctcaa ccggtagctt    600
gcagcgcgaa ctggtcgact tgagtatgca ggaagtaggc ggaattcatg gcgtagcggt    660
gaaatgctta gatatcatga cggactccga ttgcgcaggc agcttactgt agcataactg    720
```

| | |
|---|---|
| acgctgatgc tcgaaagtgc gggtatcaaa caggattaga taccctggta gtccgcacgg | 780 |
| taaacgatgg atgctcgcta ttcgtcctat ttggatgagt ggccaagtga aacattaag | 840 |
| catcccacct ggggagtacg ccggcaacgg tgaaactcaa aggaattgac ggggccccgc | 900 |
| acaagcggag gaacatgtgg tttaattcga tgatacgcga ggaaccttac ccgggcttga | 960 |
| actgccagcg aacgatacag agatgttgag gcccttcggg gcgctggtgg aggtgctgca | 1020 |
| tggttgtcgt cagctcgtgc cgtgaggtgt cggcttaagt gccataacga gcgcaaccct | 1080 |
| tttctttagt tgccatcagg tgatgctggg cactctatgg atactgccac cgtaaggtgt | 1140 |
| gaggaaggtg gggatgacgt caaatcagca cggcccttac gtccggggct acacacgtgt | 1200 |
| tacaatgggg catacagagt gttggcttaa cgcaagtttg gtctaatctt caaagtgtct | 1260 |
| ccctgttcgg attggggtct gcaactcgac cccatgaagc tggattcgct agtaatcgcg | 1320 |
| catcagccat ggcgcggtga atacgttccc gggccttgta cacaccgccc gtcaagccat | 1380 |
| gaaagctggg ggtgcctgaa gtccgtaacc gttaaggagc ggcctagggc aaaa | 1434 |

<210> SEQ ID NO 14
<211> LENGTH: 1386
<212> TYPE: DNA
<213> ORGANISM: Artificial
<220> FEATURE:
<223> OTHER INFORMATION: Uncultured Acetobacteraceae bacterium clone
      BL102 16S ribosomal RNA gene, partial sequence

<400> SEQUENCE: 14

| | |
|---|---|
| gaacgctggc ggcatgctta acacatgcaa gtcgtgcgcc ccgcaagggt agcggcggac | 60 |
| gggtgagtaa cgcgtaggaa cgtgtcctga gatggggaac aaccccggga aactggggct | 120 |
| aatgccgcat atggcctatg ggtcaaagcc ttcgggcgtc ttgggagcgg cctgcgtccg | 180 |
| attaggttgt tggtggggta atggcctacc aagcctgcga tcggtagctg gtctgagagg | 240 |
| acgatcagcc acactgggac tgagacacgg cccagactcc tacgggaggc agcagtgggg | 300 |
| aatattgggc aatgggcgca agcctgaccc agcaatgccg cgtgggtgaa gaaggtcttc | 360 |
| ggattgtaaa gccctttcgg cggggacgat gatgacggta cccgcagaag aagccccggc | 420 |
| taacttcgtg ccagcagccg cggtaatacg aaggggggcta gcgttgctcg gaattactgg | 480 |
| gcgtaaaggg cgcgtaggcg cgccagtag tcaggcgtga aattcctggg ctcaacctgg | 540 |
| gggctgcgct tgatacgctg gtgctagagg acggaagagg ctcgcggaat tcccagtgta | 600 |
| gaggtgaaat tcgtagatat tgggaagaac accggtggcg aaggcggcga gctggtccgt | 660 |
| tactgacgct gaggcgcgac agcgtgggga gcaaacagga ttagataccc tggtagtcca | 720 |
| cgccgtaaac gatgtgcgct ggatgttggg ggccctaggc cctcagtgtc gtagccaacg | 780 |
| cggtaagcgc accgcctggg gagtacggcc gcaaggttga aactcaaagg aattgacggg | 840 |
| ggcccgcaca gcggtggag catgtggttt aattcgaagc aacgcgcaga accttaccag | 900 |
| cccttgacat gggcaggacc ggtccagaga tgggccttcc ccgcaagggg cctgctgcac | 960 |
| aggtgctgca tggctgtcgt cagctcgtgt cgtgagatgt tgggttaagt cccgcaacga | 1020 |
| gcgcaaccct cgcctccagt tgccagcacg tttgggtggg cactctggag gaactgccgg | 1080 |
| tgacaagccg gaggaaggtg gggatgacgt caagtcctca tggcccttat gggctgggct | 1140 |
| acacacgtgt acaatggcg gtgacagcgg gaagccaggt cgcgaggccg agccgatccc | 1200 |
| gaaaagccgt ctcagttcag atcgcactct gcaactcggg tgcgtgaagg tggaatcgct | 1260 |
| agtaatcgcg gatcagcacg ccgcggtgaa tacgttcccg ggccttgtac acaccgcccg | 1320 |
| tcacaccatg ggagttggtt tcaccttaag ccggtgcagc aaccgcaagg agcaagccgg | 1380 |

```
                                          -continued
ccacgg                                                          1386

<210> SEQ ID NO 15
<211> LENGTH: 1418
<212> TYPE: DNA
<213> ORGANISM: Artificial
<220> FEATURE:
<223> OTHER INFORMATION: Uncultured Corynebacterium sp. clone BL135 16S
      ribosomal RNA gene, partial sequence

<400> SEQUENCE: 15
gaacgctggc ggcgtgctta acacatgcaa gtcgaacgga aaggccctgc ttgcagggta     60
ctcgagtggc gaacgggtga gtaacacgtg ggtgatctgc cctgcacttc gggataagcc    120
tgggaaactg gtctaatac tggataggac tgcactgtag gggtgtggtg gaaagctttt     180
gtggtgcagg atgagcccgc ggcctatcag cttgttggtg gggtaatggc ctaccaaggc    240
gtcgacgggt agccggcctg agagggtgta cggtcacatt gggactgaga tacggcccag    300
actcctacgg gaggcagcag tggggaatat tgcacaatgg gcgcaagcct gatgcagcga    360
cgccgcgtgg gggatgacgg ccttcgggtt gtaaactcct ttcgctaggg acgaagcttt    420
ttgtgacggt acctagataa gaagcaccgg ctaactacgt gccagcagcc gcggtaatac    480
gtagggtgcg agcgttgtcc ggaattactg ggcgtaaaga gctcgtaggt ggtttgtcgc    540
gtcgtctgtg aaataccaat gcttaacgtt ggtcgtgcag gcgatacggg cattacttga    600
gtgctgtagg ggtaactgga attcctggtg tagcggtgaa atgcgcagat atcaggagga    660
acaccgatgg cgaaggcagg ttactgggca gttactgacg ctgaggagcg aaagcatggg    720
tagcgaacag gattagatac cctggtagtc catgctgtaa acggtgggcg ctaggtgtag    780
gggtcttcca cgatttctgt gccgtagcta acgcattaag cgccccgcct ggggagtacg    840
gccgcaaggc taaaactcaa aggaattgac ggggccccgc acaagcggcg gagcatgtgg    900
attaattcga tgcaacgcga agaaccttac ctgggcttga catatggagg atcggcgtag    960
agatacgttt tcccttgtgg tcttcataca ggtggtgcat ggttgtcgtc agctcgtgtc   1020
gtgagatgtt gggttaagtc ccgcaacgag cgcaaccctt gtcttatgtt gccagcaatt   1080
cggttgggga ctcatgagag actgccgggg ttaactcgga ggaaggtggg gatgacgtca   1140
aatcatcatg cccttatgt ccagggcttc acacatgcta caatggtcga tacaataggt     1200
tgcgataccg tgaggtggag ctaatcgttt aaagtcggcc ttagttcgga ttggggtctg   1260
caactcgacc ccatgaagtc ggagtcgcta gtaatcgtag atcagcaacg ctacggtgaa   1320
tacgttcccg ggccttgtac acaccgcccg tcacgtcatg aaagttggta acacccgaag   1380
cccacggcct aaccctttgt gggagggagg gtcgaagg                           1418

<210> SEQ ID NO 16
<211> LENGTH: 1417
<212> TYPE: DNA
<213> ORGANISM: Artificial
<220> FEATURE:
<223> OTHER INFORMATION: Uncultured Peptoniphilus sp. clone BR10 16S
      ribosomal RNA gene, partial sequence

<400> SEQUENCE: 16
cgcctaacac atgcaagtcg agcgatgaac attgaatgat cccttcgggg tgatttcgat     60
cggattagcg gcgaacgggt gagtaacgcg tgaggaacct gcctcttaca acgggatagc    120
ctcgggaaac cggattaat accgtataag actccgacat ctcctgatga tgaagtcaaa    180
gcgttagcgg taagagatgg cctcgcgtct gattagcttg ttggcggggt aacggcccac    240
```

```
caaggcgacg atcagtaacc ggcctgagag ggtgaacggt cacattggaa ctgagacacg      300
gtccaaactc ctacgggagg cagcagtggg gaatcttgca caatggggc aaccctgatg       360 cagcgacgcc gcgtgagcga tgaaggtttt cgaatcgtaa agctctgtcc tatgggaaga     420
taatgacggt accatgggag gaagccccgg ctaactacgt gccagcagcc gcggtaatac     480 gtaggggcg agcgttgtcc ggaattactg ggcgtaaagg gttcgcaggc ggcatggcaa      540
gtccgatgta aaaggcgaag gctcaacctt cgtaagcatc ggaaactgtc aagcttgagt     600
gaaggagagg caagtggaat tcctagtgta gcggtggaat gcgtagatat taggaggaat    660
accggtggcg aaggcgactt gctggacttc aactgacgct gaggaacgaa agcgtgggta    720
gcaaacagga ttagatascc tggtagtcca cgccgtaaac gatgagtgct aggtgtcggg    780
ggtcaaacct cggtgccgcc gttaacacaa taagcactcc gcctgggag tacgtgcgca      840 agcatgaaac tcaaaggaat tgacgggac ccgcacaagc agcggagcat gtggtttaat     900
tcgaagcaac gcgaagaacc ttaccaggac ttgaaatact agcgcccgct ttagagataa    960
agttttttct tcggaaacgc taatacaggt ggtgcatggt tgtcgtcagc tcgtgtcgtg    1020
agatgttggg ttaagtcccg caacgagcgc aaccccttact tttagttgcc agcacgtaat   1080
ggtgggaact ctaaagggac tgccgatgat aaatcggagg aaggtgggga tgacgtcaaa   1140
tcatcatgcc ctttatgtcc tgggctacac acgtgctaca atggttggta cagagggcag   1200
caaacgagcg atcgcaagcg aatctcaaaa agccgatccc agttcggatt gcaggctgca   1260
actcgcctgc atgaagtcgg agttgctagt aatcgcgaat cagaatgtcg cggtgaatgc   1320
gttcccgggt cttgtacaca ccgcccgtca caccatggga gttggcaata cccgaagcca    1380
gcgagccaac cgcaaggagg cagctgtcga aggtagg                             1417
```

<210> SEQ ID NO 17
<211> LENGTH: 1403
<212> TYPE: DNA
<213> ORGANISM: Artificial
<220> FEATURE:
<223> OTHER INFORMATION: Uncultured Paracraurococcus sp. clone GL17 16S
      ribosomal RNA gene, partial sequence

<400> SEQUENCE: 17

```
cgaacgctgg cggcatgctt aacacatgca agtcgcgcgg gtggtttcgg ccatcagcgg      60
cggacgggtg agtatcgcgt aggaatgtat cctgaggtgg gggacaaccc tgggaaactg     120
gggctaatac cgcatgggc ctgtgggtca aagccttagg gcgccttggg agcagcctgc     180
gtccgattag gtagttggtg gggtaaaggc ctaccaagcc tgcgatcggt agctggtctg    240
agaggacgat cagccacact gggactgaga cacggcccag actcctacgg gaggcagcag   300
tggggaatat tggacaatgg gcgcaagcct gatccagcaa tgccgcgtgg gtgaagaagg   360
tcttcggatt gtaaagccct ttcggcgggg acgatgatga cggtacccgc agaagaagcc   420
ccggctaact tcgtgccagc agccgcggta atacgaaggg ggctagcgtt gctcggaatt   480
actgggcgta aagggcgcgt aggcggctct gttagtcagg cgtgaaattc ctgggctcaa    540
cctggggact gcgcttgata cggcggggct tgagggcagg agaggctcgc ggaattccca    600
gtgtagaggt gaaattcgta gatattggga agaacaccgg tggcgaaggc ggcgagctgg    660
cctgtgactg acgctgaggc gcgacagcgt ggggagcaaa caggatcaga taccctggta    720
gtccacgccg taaacgatgt gcgctggatg ttgggcggcc tagccgttca gtgtcgtggc    780
caacgcggta agcgcaccgc ctggggagta cggccgcaag gttgaaactc aaaggaattg    840
```

```
acgggggccc gcacaagcgg tggagcatgt ggtttaattc gaagcaacgc gcagaacctt      900 accagcccttt gacatgggca ggaccggcgc agagatgcgc ttttccccgca aggggcctgc     960 tgcacaggtg ctgcatggct gtcgtcagct cgtgtcgtga gatgttgggt taagtcccgc    1020
aacgagcgca accctcgcct tcagttgcca gcaggtttgg ctgggcactc tggaggaact    1080
gccggtgaca agccggagga aggtggggat gacgtcaagt cctcatggcc cttatgggct    1140
gggctacaca cgtgctacaa tggcggtgac agcgggacgc caggctgcga ggccgagccg    1200
atcccgaaaa gccgtctcag ttcggatcgc actctgcaac tcgggtgcgt gaaggtggaa    1260
tcgctagtaa tcgcggatca gcacgccgcg gtgaatacgt tcccgggcct tgtacacacc    1320
gcccgtcaca ccatgggagt tggttctacc ttaagcaggt gcggtaaccg cgaggagcta    1380
gcctgccacg gtagggtcag tga                                            1403
```

<210> SEQ ID NO 18
<211> LENGTH: 1404
<212> TYPE: DNA
<213> ORGANISM: Artificial
<220> FEATURE:
<223> OTHER INFORMATION: Uncultured Deinococcus sp. clone GL25 16S
      ribosomal RNA gene, partial sequence

<400> SEQUENCE: 18

```
gaacgctggc ggcgtgctta agacatgcaa gtcgaacgca gtcttcggac tgagtggcgc      60
acgggtgagt aacacgtgac tgacctaccc ctaaatcagg aataactcct cgaaagaggt     120
gctaatactg gatgtgatgc cgcctcgtgt ggcggcatta aagactagat cgtttaggga    180
tggggttgcg ttccatcagc tagttggtag ggtaaaggcc taccaaggcg acgacggata    240
gccggcctga gagggtggcc ggccacaggg gcactgagac acgggtccca ctcctacggg    300
aggcagcagt taggaatctt ccacaatggg cgaaagcctg atggagcgac gccgcgtgag    360
ggatgaaggt tctaggatcg taaacctctg aatcaacgac gaaagacccg acgaggggga    420
tgacggtagt tgagtaatag caccggctaa ctccgtgcca gcagccgcgg taatacggag    480
ggtgcaagcg ttacccggaa tcactgggcg taaagggcgt gtaggcggct ttataagtct    540
ggttttaaag accgaggctc aacctcggaa atggactgga tactgtgagg cttgacctct    600
ggagaggtaa ctggaattcc tggtgtagcg gtggaatgcg tagataccag gaggaacacc    660
aatggcgaag gcaagttact ggacagaagg tgacgctgag gcgcgaaagt gtggggagcg    720
aaccggatta gatacccggg tagtccacac cctaaacgat gtacgttggc ttatggcagg    780
atgctgtcat aggcgaagct aacgcgataa acgtaccgcc tgggaagtac ggccgcaagg    840
ttgaaactca aagaaattga cgggggcccg cacaagcggt ggagcatgtg gtttaattcg    900
aagcaacgcg aagaacctta ccaggtcttg acatccacag aacctttgag agatcagagg    960
gtgcccttcg gggaactgtg agacaggtgc tgcatggctg tcgtcagctc gtgtcgtgag   1020
atgttgggtt aagtcccgca acgagggcaa cccttacctt tagttgtcag ctttgagtag   1080
gacactctag agggactgcc tatgaaagta ggaggaaggc ggggatgacg tctagtcagc   1140
atggtcctta cgacctgggc tacacacgtg ctacaatggc cagaacaacg cgcagcaaac   1200
acgcgagtgt aagcgaatcg ctgaaaactg gccccagttc agatcggagt ctgcaactcg   1260
actccgtgaa gttggaatcg ctagtaatcg caggtcagca tgctgcggtg aatacgttcc   1320
cgggccttgt acacaccgcc cgtcacacca tgggagtacg ttgcagttaa aaccgccggg   1380
agccgcaagg caggcgtcta gact                                           1404
```

```
<210> SEQ ID NO 19
<211> LENGTH: 1383
<212> TYPE: DNA
<213> ORGANISM: Artificial
<220> FEATURE:
<223> OTHER INFORMATION: Uncultured Rhizobiales bacterium clone GL66 16S
      ribosomal RNA gene, partial sequence

<400> SEQUENCE: 19
gaacgctggc ggcaggctta acacatgcaa gtcgagcgcc ccgcaagggg agcggcagac      60
gggtgagtaa cgcgtgggaa tctacccatc actacggaac aactccggga aactggagct    120
aataccgtat acgtccgaga ggagaaagat ttatcggtga tggacgagcc cgcgttggat    180
tagctagttg gtggggtaat ggcctaccaa ggcgacgatc catagctggt ctgagaggat    240
gatcagccac actgggactg agacacggcc cagactccta cgggaggcag cagtggggaa    300
tattggacaa tgggcgcaag cctgatccag ccatgccgcg tgagtgatga aggccctagg    360
gttgtaaagc tctttcaacg gtgaagataa tgacggtaac tgtagaagaa gccccggcta    420
acttcgtgcc agcagccgcg gtaatacgaa ggggctagc gttgttcgga attactgggc     480
gtaaagcgca cgtaggcgga catttaagtc aggggtgaaa tcccgaggct caacctcgga    540
actgcctttg atactgggtg tctcgagtcc ggaagaggtg agtggaattc cgagtgtaga    600
ggtgaaattc gtagatattc ggaggaacac cagtggcgaa ggcggctcac tggtccggta    660
ctgacgctga ggtgcgaaag cgtggggagc aagcagaatt agataccctg gtagtccacg    720
ccgtagacta tgagagctag ccgtcggtaa gtttacttat cggtggcgca gctaacgcat    780
taagctctcc gcctggggag tacggtcgca agattaaaac tcaaaggaat tgacggggc     840 ccgcacaagc ggtggagcat gtggtttaat tcgaagcaac gcgcagaacc ttaccagccc    900
ttgacatgtc cgtgaccggc tcgagagatc gagctttctc ttcggagcac ggagcacagg    960
tgctgcatgg ctgtcgtcag ctcgtgtcgt gagatgttgg gttaagtccc gcaacgagcg   1020 caacccttt ccttatttgc cagcgggtta agccgggaac tttaaggata ctgccagtga    1080
caaactggag gaaggcgggg acgacgtcaa gtcatcatgg cccttacgac cagggctaca   1140
cacgtgctac aatggtaggt acagagggtt gctacacagc gatgtgatgc taatctcaaa   1200
aagcctatcg tagtccggat gggagtctgc aactcgactc catgaagtcg gaatcgctag   1260
taatcgcaga tcagaatgct gcggtgaata cgttcccggg ccttgtacac accgcccgtc   1320
acaccatggg agtctattgc accagaagta ggtagcctaa cgaaagaggg cgcttaccac   1380
ggt                                                                 1383

<210> SEQ ID NO 20
<211> LENGTH: 1397
<212> TYPE: DNA
<213> ORGANISM: Artificial
<220> FEATURE:
<223> OTHER INFORMATION: Uncultured Chitinophaga sp. clone GL77 16S
      ribosomal RNA gene, partial sequence

<400> SEQUENCE: 20
acgctagcgg caggcttaac acatgcaagt cgagcgctcc agcaatggag agcggcaaac      60
gggtgcggaa cacgtacgca atctgcccct cactggggaa tagcccgaag aaattcggat    120
taatacccca taaatagca aggtggcatc acctaactat taaagttccg gcggtgaagg      180
atgagcgtgc gtcctattag gtagttggta gggtaacggc ctaccaagcc gacgataggt    240
agctggtgtg agagcacgac cagccacacg ggcactgaga cacgggcccg actcctacgg    300
gaggcagcag tgaggaatat tggtcaatgg acgaaagtct gaaccagcca tgccgcgtgg    360
```

```
aggatgaagg ccctctgggt tgtaaacttc ttttatcagg gaagaaaagt actatttcta    420
tggtatccga cggtacctga tgaataagca ccggctaact ccgtgccagc agccgcggta    480
atacggaggg tgcaagcgtt atccggattt actgggttta aagggtgtgt aggcggactt    540
ttaagtcaga ggtgaaatcc cagggctcaa ccctggaact gcccctgata ctattggtct    600
tgaatatcgt tgaggtaggc ggaatacatc atgtagcggt gaaatgctta gatatgatgt    660
agaacaccga ttgcgaaggc agcttactaa acgattattg acgctgaggc acgaaagcgt    720
ggggatcaaa caggattaga taccctggta gtccacgccc taaacgatga ttactcgtca    780
ttggcgatac actgtcagtg actaagcgaa agcattaagt aatccacctg ggaagtacgt    840
tcgcaagaat gaaactcaaa ggaattgacg gggtccgca caagcggtgg agcatgtggt    900
ttaatttgat gatacgcgag gaaccttacc tgggctagaa tgctaccgga cagcctgtga    960
aagcaggtct tccgcaagga ctggtaggaa ggtgctgcat ggctgtcgtc agctcgtgcc   1020
gtgaggtgtt gggttaagtc ccgcaacgag cgcaaccccc atcttcagtt gccaacaggt   1080
aatgctggga actctggaga aactgccgcc gtaaggcgtg aggaaggagg ggatgatgtc   1140
aagtcatcat ggccttatg cccagggcta cacacgtgct acaatgggag ggacaatggg   1200
ctgctacctg gtaacaggat gcgaatctca aaaaccctct ctcagttcgg attgaggtct   1260
gcaactcgac ctcatgaagc tggaatcgct agtaatcgca gatcagcagt gctgcggtga   1320
atacgttccc ggaccttgta cacaccgccc gtcaagccat ggaagctggg tgtacctaaa   1380
gtcggtaacc gcaagga                                                  1397

<210> SEQ ID NO 21
<211> LENGTH: 1346
<212> TYPE: DNA
<213> ORGANISM: Artificial
<220> FEATURE:
<223> OTHER INFORMATION: Uncultured Amaricoccus sp. clone GL97 16S
      ribosomal RNA gene, partial sequence

<400> SEQUENCE: 21
aacgctggcg gcaggcttaa cacatgcaag tcgagcgggc accttcgggt gtcagcggcg     60
aacgggtgag taacgcgtgg gaacgtgccc tttcctccgg aatagcctcg ggaaactgag    120
attaatgccg gatacgccct tttggggaaa gattatcgg ggaaggatcg gcccgcgttg    180
gattaggtag ttggtggggt aatggcctac caagccgacg atccatagct ggtttgagag    240
gatgatcagc cacactggga ctgagacacg gcccagactc ctacgggagg cagcagtggg    300
gaatcttgga caatgggggc aaccctgatc cagccatgcc gcgtgatcga tgaaggcctt    360
agggttgtaa agatctttca gctgggaaga taatgacggt accagcagaa gaagccccgg    420
ctaactccgt gccagcagcc gcggtaatac ggagggggct agcgttgttc ggaatttact    480
gggcgtaaag cgcacgtagg cggattggca agttgggggt gaaatcccag ggctcaaccc    540
tggaactgcc tccagaactt ccagtcttga ggtcgagaga ggtgagtgga attccgagtg    600
tagaggtgaa attcgtagat attcggagga acaccagtgg cgaaggcggc tcactggctc    660
gatactgacg ctgaggtgcg aaagcgtggg gagcaaacag gattagatac cctggtagtc    720
cacgccgtaa acgatgagag ctagtcgtcg ggaagcatgc tcttcggtga cgcagttaac    780
gcattaagct ctccgcctgg ggagtacggc cgcaaggtta aaactcaaag gaattgacgg    840
gggcccgcac aagcggtgga gcatgtggtt taattcgaag caacgcgcag aaccttacca    900
tcccttgact tggatatcgc ggctccagag atggagcttt cagttcggct ggatatgaca    960
```

```
caggtgctgc atggctgtcg tcagctcgtg tcgtgagatg ttgggttaag tcccgcaacg   1020
agcgcaaccc tcgctgctag ttgccagcat tcagttgggc actctagcgg aaccgccggt   1080
gataagccgg aggaaggtgg ggatgacgtc aagtcctcat ggcccttacg ggatgggcta   1140
cacacgtgct acaatggtgg tgacaatggg ttaatcccca aaagccatct cagttcggat   1200
tggggtctgc aactcgaccc catgaagttg gaatcgctag taatcgcgta acagcatgac   1260
gcggtgaata cgttcccggg ccttgtacac accgcccgtc acaccatggg aattgggcct   1320
acccgaaggt ggtgcgccaa ccagca                                         1346

<210> SEQ ID NO 22
<211> LENGTH: 1403
<212> TYPE: DNA
<213> ORGANISM: Artificial
<220> FEATURE:
<223> OTHER INFORMATION: Uncultured Deinococcus sp. clone GL109 16S
      ribosomal RNA gene, partial sequence

<400> SEQUENCE: 22
aacgctggcg gcgtgcttaa gacatgcaag tcgaacgcag tcttcggact gagtggcgca     60
cgggtgagta acacgtaact gacctacccc aaagtcgcgg ataaccagcc gaaaggttgg    120
ctaatacgtg atgtgaacat tcgccgtggc gaatgtttaa agacttgatc gctttgggat    180
ggggttgcgt tccatcagct agttggtggg gtaaaggccc accaaggcaa cgacggatag    240
ccggcctgag agggtggccg gccacagggg cactgagaca cgggtcccac tcctacggga    300
ggcagcagtt aggaatcttc cacaatgggc gaaagcctga tggagcgacg ccgcgtgagg    360
gaagaaggtt ctcggatcgt aaacctctga accaacgacg aaagaccccgg caagggagat    420 gacggtagtt gggtaatagc accggctaac tccgtgccag cagccgcggt aatacggagg    480
gtgcaagcgt tacccggaat cactgggcgt aaagggcgtg taggcggcca cttaagtccg    540
attttaaaga ccgaagctca acttcggag tggattggat actggatggc ttgacctctg    600
gagaggaaac cggaattcct ggtgtagcgg tggaatgcgt agataccagg aggaacacca    660
atggcgaagg caggttctg gacagaaggt gacgctgagg cgcgaaagtg tgggagcga    720 accggattag ataccgggt agtccacacc ctaaacaatg tacgttggct tatggccgga    780
tgcggtcatg ggcgaagcta acgcgataaa cgtaccgcct gggaagtacg gccgcaaggt    840
tgaaactcaa agaaattgac gggggcccgc acaagcggtg gagtatgtgg tttaattcga    900
agcaacgcga agaaccttac caggtcttga catcctacga accttccgga gatgaagggg    960
tgcccctcgg ggagcgtaga gacaggtgct gcatggctgt cgtcagctcg tgtcgtgaga   1020
tgttgggtta agtcccgcaa cgagcgcaac ccctaccttt agttgctagc attgagttga   1080
gcactctaga gggactgcct atgaaagtag gaggaaggcg gggatgacgt ctagtcagca   1140
tggtccttac gacctgggct acacacgtac tacaatggcc aagacaacgc gcagcaaaca   1200
cgcgagtgta agcgaatcgc tgaaacttgg ccccagttca gatcggagtc tgcaactcga   1260
ctccgtgaag ttggaatcgc tagtaatcgc aggtcagcat actgcggtga atacgttccc   1320
gggccttgta cacaccgccc gtcacaccat ggaagtacgt tgcagctaaa accaccggga   1380
gccgcaaggc aggtgtctag gct                                           1403

<210> SEQ ID NO 23
<211> LENGTH: 1298
<212> TYPE: DNA
<213> ORGANISM: Artificial
<220> FEATURE:
<223> OTHER INFORMATION: Uncultured Xanthomonadaceae bacterium clone
```

GL118 16S ribosomal RNA gene, partial sequence

<400> SEQUENCE: 23

| | | | | |
|---|---|---|---|---|
| gaccttcggg | tgaaagcagg | gatcttcgga | ccttgcgcag | atggatgagc | cgatgccgga | 60 |
| ttagctactt | ggaggggtaa | aggcccacca | aggcgacgat | ccgtagctgg | tctgagagga | 120 |
| tgatcagcca | caccgggact | gagacacggc | ccggactcct | acgggaggca | acagtgggga | 180 |
| atattggaca | atgggcgcaa | gcctgatcca | gccatgccgc | gtgtgtgaag | aaggccttcg | 240 |
| ggttgtaaag | cacttttgtt | ggggaagaaa | agcttccggt | taatacccgg | gagtcatgac | 300 |
| ggtacccaaa | gaataagcac | cggctaactt | cgtgccagca | gccgcggtaa | tacgaagggt | 360 |
| gcaagcgtta | ctcggaatta | ctgggcgtaa | agcgtgcgta | ggtggtttgt | taagtctgat | 420 |
| gtgaaagccc | tgggctcaac | ctgggaattg | cattggatac | tggcaggctt | gagtgcggta | 480 |
| gaggatagcg | gaattcccgg | tgtagcagtg | aaatgcgtag | atatcgggag | gaacatctgt | 540 |
| ggcgaaggcg | gctatctgga | ccagcactga | cactgaggca | cgaaagcgtg | gggagcaaac | 600 |
| aggattagat | accctggtag | tccacgccct | aaacgatgcg | aactggatgt | tgggtgcact | 660 |
| taggcactca | gtatcgaagc | taacgcgtta | agttcgccgc | ctggggagta | cggtcgcaag | 720 |
| actgaaactc | aaaggaattg | acgggggccc | gcacaagcgg | tggagtatgt | ggtttaattc | 780 |
| gatgcaacgc | gaagaacctt | acctggcctt | gacatgcacg | aactttcca | gagatggatt | 840 |
| ggtgccttcg | ggaaccgtga | cacaggtgct | gcatggctgt | cgtcagctcg | tgtcgtgaga | 900 |
| tgttgggtta | agtcccgcaa | cgagcgcaac | ccctgtcctt | agttgccagc | acgtaatggt | 960 |
| gggaactcta | aggagaccgc | cggtgacaaa | ccggaggaag | gtgggatga | cgtcaagtca | 1020 |
| tcatggccct | tacggccagg | gctacacacg | tactacaatg | gtggggacag | agggctgcca | 1080 |
| gcgcgcgagc | gtgagccaat | cccagaaacc | ccatctcagt | ccggatcgca | gtctgcaact | 1140 |
| cgactgcgtg | aagtcggaat | cgctagtaat | cgcagatcag | cattgctgcg | gtgaatacgt | 1200 |
| tcccgggcct | tgtacacacc | gcccgtcaca | ccatgggagt | gggttgctcc | agaagtcgct | 1260 |
| agtctaacct | tcgggaggac | gggaccacgg | aggtatca | | | 1298 |

<210> SEQ ID NO 24
<211> LENGTH: 1451
<212> TYPE: DNA
<213> ORGANISM: Artificial
<220> FEATURE:
<223> OTHER INFORMATION: Uncultured bacterium clone GR10 16S ribosomal
      RNA gene, partial sequence

<400> SEQUENCE: 24

| | | | | |
|---|---|---|---|---|
| aacgctggcg | gcgtgcctaa | tacatgcaag | tagaacgctg | aggtttggtg | tttacactag | 60 |
| actgatgagt | tgcgaacggg | tgagtaacgc | gtaggtaacc | tgcctcatag | cgggggataa | 120 |
| ctattggaaa | cgatagctaa | taccgcataa | gagtaattaa | cacatgttag | ttatttaaaa | 180 |
| ggagcaattg | cttcactgtg | agatggacct | gcgttgtatt | agctagttgg | tgaggtaaag | 240 |
| gctcaccaag | gcgacgatag | atagccgacc | tgagagggtg | atcggccaca | ctgggactga | 300 |
| gacacggccc | ggactcctac | gggaggcagc | agtagggaat | cttcggcaat | ggacggaagt | 360 |
| ctgaccgagc | aacgccgcgt | gagtgaagaa | ggttttcgga | tcgtaaagct | ctgttgttag | 420 |
| agaagaacgt | tggtaggagt | ggaaaatcta | ccaagtgacg | gtaactaacc | agaaagggac | 480 |
| ggctaactac | gtgccagcag | ccgcggtaat | acgtagggac | caagcgttgt | tcggatttac | 540 |
| tgggcgtaaa | gggcgcgtag | gcggtttgtc | aagtcagttg | tgaaatctcc | gagcttaact | 600 |
| cggaacggtc | aactgatact | gtcaaactag | agtacagaag | gggcaatcgg | aattcttggt | 660 |

```
gtagcggtga aatgcgtaga tatcaagagg aacacctgag gtgaagacgg gttgctgggc    720
tgatactgac gctgaggcgc gaaagctagg gtagcaaacg ggattagata ccccggtagt    780
cctagcccta aacgatgaat gcttggtgtc tggagttttt aatctctggg tcccgtcgct    840
aacgctttta gcattccgcc tggggagtac gcacgcaagt gtgaaactca aaggaattga    900 cgggacccg cacaagcggt ggagcatgtg gtttaattcg acgcaacgcg aagaaccta    960 cctgaactag aatgcgagga aaagctgatg taatgtcagt gtgggagcaa tcccgtccga   1020
agcaaggtgc tgcatggctg tcgtcagctc gtgtcgtgag atgtagggtt aagtcccgca   1080
acgagcgcaa cccctattaa cagttgccat cattaagttg ggaactctgt taagactgct   1140
gttgataaaa cggaggaagg tggggacgac gtcaagtcat catggccttt atgttcaggg   1200
ctacacacgt gctacaatgg acggtacaaa ccgttgcaat cccgcaaggg ggagctaatc   1260
ggaaaaaacc gttctcagtt cggattgtag tctgcaactc gactacatga agttggaatc   1320
gctagtaatc gcggatcagc atgccgcggt gaatacgttc ccgggtcttg tacacaccgc   1380
ccgtcacatc acgaaagtgg attgtactag aagtagctgg gctaaccttc gggaggcaag   1440
ttactacggt a                                                        1451

<210> SEQ ID NO 25
<211> LENGTH: 1437
<212> TYPE: DNA
<213> ORGANISM: Artificial
<220> FEATURE:
<223> OTHER INFORMATION: Uncultured Dermacoccus sp. clone GR60 16S
      ribosomal RNA gene, partial sequence

<400> SEQUENCE: 25
gaacgctggc ggcgtgctta acacatgcaa gtcgaacgat gaagccgcag cttgctgtgg     60
tggattagtg gcgaacgggt gagtaacacg tgagtaacct gcccttcact ctgggataag    120
ccttggaaac gaggtctaat actggatatt cattcatgat cgcatggttg tgggtggaaa    180 gatttttgg tgggggatgg actcgcggcc tatcagcttg ttggtgaggt agtggcttac    240
caaggctttg acgggtagcc ggcctgagag ggtgaccggc cacactggga ctgagacacg    300
gcccagactc ctacgggagg cagcagtggg gaatattgca caatgggcga aagcctgatg    360
cagcgacgcc gcgtgaggga tgacggcctt cgggttgtaa acctctttca ccagggacga    420
agcggaagtg acggtacctg gagaagaagc accggctaac gacgtgccag cagccgcggt    480
aatacgtagg gtgcgagcgt tgtccggaat tattgggcgt aaagagcttg taggcggttt    540
gtcgcgtctg ctgtgaaaga ccggggctta actccggttc tgcagtgggt acgggcaggc    600
tagagtatgg taggggagac tggaatcctg gtgtagcggt gaaatgcgca gatatcagga    660
ggaacaccga tggcgaaggc aggtctctgg gccattactg acgctgagaa gcgaaagcat    720
ggggagcgaa caggattaga taccctggta gtccatgccg taaacgttgg gcgctaggtg    780
tgggactcat tccacgagtt ccgtgccgca gctaacgcat caagcgcccc gcctggggag    840
tacggccgca aggctaaaac tcaaaggaat tgacgggggc ccgcacaagc ggcggagcat    900
gcggattaat tcgatgcaac gcgaagaacc ttaccaaggc ttgacataca ccggaatgtg    960
ccagagatgg tgcagccttt tggctggtgt acaggtggtg catggttgtc gtcagctcgt   1020
gtcgtgagat gttgggttaa gtcccgcaac gagcgcaacc ctcgttccat gttgccagca   1080
cgtgatggtg gggactcatg ggagactgcc ggggtcaact cggaggaagg tggggatgac   1140
gtcaaatcat catgcccctt atgtcttggg cttcacgcat gctacaatgg ccggtacaga   1200
```

```
gggcagcgat accgtgaggt ggagcgaatc ccttaaaacc ggtctcagtt cggattgggg    1260
tctgcaactc gaccccatga agttggagtc gctagtaatc gcagatcagc agtgctgcgg    1320
tgaatacgtt cccgggcctt gtacacaccg cccgtcaagt cacgaaagtt ggtaacaccc    1380
gaagccggtg gcctaaccct tgtgggggga gccgtcgaag gtgggattgg cgattgg       1437
```

<210> SEQ ID NO 26
<211> LENGTH: 1401
<212> TYPE: DNA
<213> ORGANISM: Artificial
<220> FEATURE:
<223> OTHER INFORMATION: Uncultured Sphingobacteriales bacterium clone
      GR63 16S ribosomal RNA gene, partial sequence

<400> SEQUENCE: 26

```
gctgacggca ggcctaataa tgcaagtcga gcgggtagca ataccagcgg caaacgggtg      60
cgtaacgcgt aagcgaccta cccctcaccg gcggatagcc ttgcgaaagc gagggtaaac     120
cgccatagtt caagaaagct gcctggtttt tttgataaac gttttgggtg atggaggggc     180
ttgcgtctga ttagctggtt ggagaggtaa cggctcacca aggcgatgat cagtagggat     240
ctgagaggat tatcccccac atgggtactg agacacggac ccaactccta cgggaggcag     300
cagtagggaa tattgggcaa tggaggcaac tctgacccag ccatgccgcg tgcaggacga     360 cggcccttttg ggttgtaaac tgcttttatc aaggaagaat ggatagcttg cgggctattg     420
tgacggtatt tgatgaataa gcaccggcta actccgtgcc agcagccgcg gtaatacgga     480
gggtgcgagc gttgtccgga tttattgggt ttaaagggtg cgtaggtggt tttttaagtc     540
tggattgaaa gctggttgct caacgatcag atgagtctgg aaactgaagg acttgaatgt     600
gatagcggta gctggaatgg gccatgtagc ggtgaaatgc atagatatgt cccgaactc     660 cgattgcgaa ggcaggctac tgggtcatga ttgacactga gcacgagag catgggtagc     720 caacaggatt agataccctg gtagtccatg ccgtaaacga tgattactgg ctgtttggga     780
gcgattttga gtggctgagc gaaagcgtta agtaatccac ctggggagta cgccggcaat     840
ggtgaaactc aaaggaattg acggggggtcc gcacaagcgg tggagcatgt ggtttaattc     900
gatgatacgc gaggaacctt acctgggcta gaatgcgcgt gaatgactca gcgatgggtc     960
agtgtagcaa tacacacaaa gcaaggtgct gcatggctgt cgtcagctcg tgccgtgagg    1020
tgttgggtta agtcccgcaa cgagcgcaac ccttatcaac tgttgccagc atgtaatggt    1080
ggggactcag tttagactgc ctgcgcaagc agagaggaag gggggacga cgtcaagtca     1140 tcatggccct tacgtccagg gcgacacacg tgctacaatg gtcggtacag cgggtagcta    1200
ctgggtaacc agatgccaat cttgtaaagc cggtcacagt tcggattggg gtctgcaact    1260
cgaccccatg aagctggaat cgctagtaat cgcgcatcag ccatggcgcg gtgaatacgc    1320
tcccggacct tgtacacacc gcccgtcaag ccatgggagt cgggggggacc tgaagcgggg    1380 gttaatagac ctgtaagggt a                                              1401
```

<210> SEQ ID NO 27
<211> LENGTH: 1419
<212> TYPE: DNA
<213> ORGANISM: Artificial
<220> FEATURE:
<223> OTHER INFORMATION: Uncultured Deinococcus sp. clone GR66 16S
      ribosomal RNA gene, partial sequence

<400> SEQUENCE: 27

```
gaacgctggc ggcgtgctta agacatgcaa gtcgaacgca gtcttcggac tgagtggcgc      60
```

```
acgggtgagt aacacgtaac ttgacctacc cccaagtcgc gaataaccag ccgaaaggat      120
ggctaatacg tgatgtgatg atccgctatg gcggatcatt aaagacttga tcgcttgggg      180
atggggttgc gttccatcag ctagttggta aggtaaaggc ttaccaaggc aacgacggat      240
agccggcctg agagggtggc cggccacagg ggcactgaga cacgggtccc actcctacgg      300
gaggcagcag ttaggaatct tccacaatgg gcgcaagcct gatggagcga cgccgcgtga      360
gggatgaagg ttctcggatc gtaaacctct gaaccaacga cgaaagaccc gacaagggag      420
atgacggtag ttgggtaata gcaccggcta actccgtgcc agcagccgcg gtaatacgga      480
gggtgcaagc gttacccgga atcactgggc gtaaagggcg tgtaggcggt tacctaagtc      540 cgatttaaa gaccgaagct caacttcggg agtggattgg atactgagtg acttgacctc      600
tggagaggaa accggaattc ctggtgtagc ggtggaatgc gtagatacca ggaggaacac      660
caatggcgaa ggcaggtttc tggacagaag gtgacgctga ggcgcgaaag tgtgggagc       720 gaaccggatt agatacccgg gtagtccaca ccctaaacaa tgtacgttgg ctaaccgccg      780
gatgcggtgg ttggcgaagc taacgcgata aacgtaccgc ctgggaagta cggccgcaag      840
gttgaaactc aaagaaattg acgggggccc gcacaagcgg tggagtatgt ggtttaattc      900
gaagcaacgc gaagaacctt accaggtctt gacatccaag gaaccttccg gaaatggaag      960
gtgcccctcg gggaaccttg agacaggtgc tgcatagctg tcgtcagctc gtgtcgtgag     1020
atgttgggtt aagtcccgca acgagcgcaa ccctaccctt agttgctag cattgagttg      1080 agcactctag agggactgcc tatgaaagta ggaggaaggc ggggatgacg tctagtcagc     1140 atggtccta cgacctgggc tacacacgta ctacaatggc caagacaacg cgcagccaac      1200
ccgcgagggt cagcgaatcg cttaaacttg gccccagttc agatcggagt ctgcaactcg     1260
actccgtgaa gttggaatcg ctagtaatcg caggtcagca tactgcggtg aatacgttcc     1320
cgggccttgt acacaccgcc cgtcacacca tgggagtacg ttgcagttga aaccgccggg     1380
agccgcaagg caggcgtcta gactgtggcg catgactgg                             1419
```

<210> SEQ ID NO 28
<211> LENGTH: 1417
<212> TYPE: DNA
<213> ORGANISM: Artificial
<220> FEATURE:
<223> OTHER INFORMATION: Uncultured Actinomycetales bacterium clone GR72
      16S ribosomal RNA gene, partial sequence

<400> SEQUENCE: 28

```
gaacgctggc ggcgtgctta acacatgcaa gtcgagcgaa gcttcttcct tcgggaagaa       60
tgacttagcg gcgaacgggt gagtaacacg tgggcaacct gcccttagct ctgggataag      120
cgatggaaac gtcgtctaat accggatatg acacgggatg gcatcatctc cgtgtggaaa      180
gaatttcggc taaggatggg cccgcggcct atcagcttgt tggtgggta gtggcccacc       240 aaggcgacga cgggtaaccg gcctgagagg gcgaccggtc acactgggac tgagacacgg      300
cccagactcc tacgggaggc agcagtgggg aatattgcac aatgggcgaa agcctgatgc      360
agcgacgccg cgtgagggat gacggccttc gggttgtaaa cctctttcag cagggacgaa      420
gcgaaagtga cggtacctgc agaagaagcg ccggccaact acgtgccagc agccgcggta      480
atacgtaggg cgcaagcgtt gtccggaatt attgggcgta aagagctcgt aggcggttta      540
tcacgtcggc tgtgaaatcc cgaggcttaa cctcgggcct gcagtcgata cgggttgact      600
agagtgaagc aggggaggct ggaattcctg gtgtagcggt gaaatgcgca gatatcagga      660
ggaacaccgg tggcgaaggc gggtctctgg gctttaactg acgctgagga cgaaagcgt       720
```

```
gggtagcgaa caggattaga taccctggta gtccacgccg taaacggtgg gcgctaggtg      780
tggggaccat tccacggttt ccgtgccgca gctaacgcat taagcgcccc gcctggggag      840
tacggccgca aggctaaaac tcaaaggaat tgacgggggc ccgcacaagc ggcggagtat      900
gttgcttaat tcgatgcaac gcgaagaacc ttaccaaggc ttgacatata ccgaaaactc      960
atagagatat gaggtccttt tgggcggtat acaggtggtg catggttgtc gtcagctcgt     1020
gtcgtgagat gttgggttaa gtcccgcaac gagcgcaacc ctcgttctat gttgccagca     1080
cgtaatggtg gggactcata ggagactgcc ggggtcaact cggaggaagg tggggatgac     1140
gtcaaatcat catgcccctt atgtcttggg ctgcaaacat actacaatgg ccggtacaaa     1200
gggctgcgat accgcaaggt ggagcgaatc ccaaaaagcc ggtctcagtt cggattgggg     1260
tctgcaactc gaccccatga agtcggagtc gctagtaatc gcagatcagc aacgctgcgg     1320
tgaatacgtt cccgggcctt gtacacaccg cccgtcaagt cacgaaagtc ggtaacaccc     1380
gaagccgggg cccaaccttt ggagggagcc gtcgaag                              1417

<210> SEQ ID NO 29
<211> LENGTH: 1437
<212> TYPE: DNA
<213> ORGANISM: Artificial
<220> FEATURE:
<223> OTHER INFORMATION: Uncultured Burkholderiales bacterium clone GR83
      16S ribosomal RNA gene, partial sequence

<400> SEQUENCE: 29
tgaacgctgg cggaatgctt tacacatgca agtcgagcgg cagcgcgggg caacctggcg       60
gcgagcggcg aacgggtgag taatacatcg gaacgtgccc agacgtgagg gataactact      120
cgaaagagta gctaataccg catatgatct aaggatgaaa gcggggatc gcaagacctc       180 gcgcgtttgg agcggccgat ggcagattag gtagttggtg gggtaaaggc ttaccaagcc      240
tgcgatctgt agctggtctg agaggacgac cagccacact gggactgaga cacggcccag      300
actcctacgg gaggcagcag tggggaattt tggacaatgg gcgaaagcct gatccagcca      360
ttccgcgtgc aggatgaagg ccctcgggtt gtaagctgct tttgtacaga acgaaaaagc      420
tctggttaat acctggagtc catgacggta ctgtaagaat aagcaccggc taactacgtg      480
ccagcagccg cggtaatacg tagggtgcaa gcgttaatcg gaattactgg gcgtaaagcg      540
tgcgcaggcg gtgatgtaag acagttgtga atccccggg ctcaacctgg gaactgcatc       600
tgtgactgca ttgctggagt gcggcagagg gggatgaat tccgcgtgta gcagtgaaat       660
gcgtagatat gcggaggaac accgatggcg aaggcaatcc cctgggcctg cactgacgct      720
catgcacgaa agcgtgggga gcaaacagga ttagataccc tggtagtcca cgccctaaac      780
gatgtcaact ggttgttggg tttttattaa ctcagtaacg aagctaacgc gtgaagttga      840
ccgcctgggg agtacggccg cgaggttgaa actcaaagga attgacgggg acccgcacaa      900
gcggtggatg atgtggttta attcgatgca acgcgaaaaa ccttacccac ctttgacatg      960
tacgaaagtt gccagagatg gcttcgtgct cgaaagagag ccgtaacaca ggtgctgcat     1020
ggctgtcgtc agctcgtgtc gtgagatgtt gggttaagtc ccgcaacgag cgcaaccctt     1080
gccattagtt gctacgaaag ggcactctaa tgggactgcc ggtgacaaac cggaggaagg     1140
tggggatgac gtcaagtcct catggccctt ataggtgggg ctacacacgt catacaatgg     1200
ctggtacaga gggttgccaa cccgcgaggg ggagctaatc ccacaaagcc agtcgtagtc     1260
cggatcgcag tctgcaactc gactgcgtga agtcggaatc gctagtaatc gcggatcaga     1320
```

```
atgtcgcggt gaatacgttc ccgggtcttg tacacaccgc ccgtcacacc atgggagcgg      1380
gttctgccag aagtggttag cctaaccgta aggagggcga tcaccacggc agggttc         1437
```

<210> SEQ ID NO 30
<211> LENGTH: 1402
<212> TYPE: DNA
<213> ORGANISM: Artificial
<220> FEATURE:
<223> OTHER INFORMATION: Uncultured Thermomicrobium sp. clone GR108 16S
      ribosomal RNA gene, partial sequence

<400> SEQUENCE: 30

```
cgctggcggc gtgcctaatg catgcaagtc gaacggggtg tccttcgggg cacttacgtg        60
gcggacgggt gaggaccacg tgggcaatct gccgtctggt gggggatagc ttccggaaac       120
gggaggtaat tccgcatgag ctcgcgtccc gagtggggga tgtgaggaaa gggtctttgg       180
acccgccgga cgaggagcct gcgcccgatt agcttgttgg tggggtaacg gcctaccaag       240
gcgatgatcg gtcgctgatc tgagaggatg atcagccaca cggggactga gacacggccc       300
cgactcctac gggaggcagc agcaaggaat tttccgcaat gggggaaacc ctgacggagc       360
aacgccgcgt gcgggatgac gccttctcggg gtgtaaaccg ctgttcgggg ggacgaagca       420
ctgacggtac ccccggagga aggcccggct aactacgtgc cagcagccgc ggtaatacgt       480
aggggccaag cgttgtccgg agttactggg cgtaaagcgt gcgcaggcgg ctcgttgcgc       540
ccgacgtgaa agcccccggc tcaaccgggg agggtcgtcg ggacgggcg agcttgaggg       600 tatcagggc tggtggaact cccggtgtag tggtgaaatg cgtagagatc gggaagaaca       660
cccgtggcga aggcggccag ctgggataca cctgacgctg aggcacgaag gcgtggggag       720
cgaacgggat tagataccc gtagtccac gcagtaaacg atgcagacta ggcgtggggg       780
gacttgaccc cctccgtgcc ggagctaacg cgggaagtct gccgcctggg gagtacggcc       840
gcaaggctaa aactcaaagg aattgacggg gccccgcaca agcggcggag cgtgctcttt       900
aattcgtcgc gacgcgaaga accttaccaa ggcttgacat gggactgcag agccgggaaa       960
ccggttggcc ttcgagggtg tcccaccggt gctgcatggc tgtcgtcagc tcgtgtcgtg      1020
agatgttggg ttaagtcccg caacgagcgc aaccctgtg gtcagttgtg atttctggc       1080 cagactgccg ggagcaaacc ggaggaaggt ggggatgacg tcaagtccgc atggcccgta      1140
cgtcttgggc gagaagcacg ctacaatggc cgggacagag ggtcgccaag cggtaacgcg      1200
gagccaatcc cagaaacccg gtctcagttc ggatcgaggg ctgcaacccg cctcgtgaa      1260 ggtggagtcg ctagtaaccg cagatcagca ctgctgcggt gaatatgttc ccgggccttg      1320
tacacaccgc ccgtcacgtc acgaaagccg gcaacacctg aagccggtgg gcgaactcgc      1380
aagaggcgca gccgtcgagg gt                                              1402
```

<210> SEQ ID NO 31
<211> LENGTH: 1443
<212> TYPE: DNA
<213> ORGANISM: Artificial
<220> FEATURE:
<223> OTHER INFORMATION: Uncultured Acinetobacter sp. clone JEL30 16S
      ribosomal RNA gene, partial sequence

<400> SEQUENCE: 31

```
gaacgctggc ggcaggctta acacatgcaa gtcgaacgga tcacttcggt ggttagtggc        60
gaacgggtga gtaatgccta ggaatctgcc tattagcggg ggataacgtt ccgaaaggaa       120
cgctaatacc gcatacgccc tacgggggaa agcagggat cttcggacct tgcactaata       180
```

-continued

| | |
|---|---|
| gatgagccta ggtcagatta gctagttggt gaggtaaagg ctcaccaagg cgacgatctg | 240 |
| tagcgggtct gagaggatga tccgccacac tggaactgag acacggtcca gactcctacg | 300 |
| ggaggcagca gtggggaata ttggacaatg ggcgcaagcc tgatccagcc atgccgcgtg | 360 |
| tgtgtagaag gccttttggt tgtaaagcac tttaagcggg gaggagggta ctcttgttaa | 420 |
| taccaagaag tatcggacgt tacccgcaga ataagcaccg gctaactctg tgccagcagc | 480 |
| cgcggtaata cagagggtgc gagcgttaat cggaattact gggcgtaaag cgcgcgtagg | 540 |
| cggttattta gtcggatgt gaaatccccg agctcaactt gggaattgca ttcgatactg | 600 |
| ggtagctaga gtatgggaga ggaaggtaga attccaggtg tagcggtgaa atgcgtagag | 660 |
| atctggagga ataccgatgg cgaaggcagc cttctggcct aatactgacg ctgaggtgcg | 720 |
| aaagcatggg gagcaaacag gattagatac cctggtagtc catgccgtaa acgatgtcaa | 780 |
| ctagccgttg gggcctttga ggcttagtg gcgcagctaa cgcgataagt tgaccgcctg | 840 |
| gggagtacgg tcgcaagact aaaactcaaa tgaattgacg ggggcccgca caagcggtgg | 900 |
| agcatgtggt ttaattcgat gcaacgcgaa gaaccttacc tggtcttgac atagtgagaa | 960 |
| cgatccagag atggattggt gccttcggga attcatatac aggtgctgca tggctgtcgt | 1020 |
| cagctcgtgt cgtgagatgt tgggttaagt cccgcaacga gcgcaaccct tttccttatt | 1080 |
| tgccagcact tcgggtggga actctaagga tactgccagt gacaaactgg aggaaggcgg | 1140 |
| gggcgacgtc aagtcatcat ggcccttacg accagggcta cacacgtgct acaatggtcg | 1200 |
| gtacaaaggg ttgctaactc gcgagagcat gctaatctca aaaagccgat cgtagtccgg | 1260 |
| attggagtct gcaactcgac tccatgaagt cggaatcgct agtaatcgcg gatcggaatg | 1320 |
| ccgcggtgaa tacgttcccg ggccttgtac acaccgcccg tcacaccatg ggagtttgtt | 1380 |
| gcaccagaag taggtagtct aaccctcggg agaacgctta ccacggtgtg gccgatgact | 1440 |
| ggg | 1443 |

<210> SEQ ID NO 32
<211> LENGTH: 1458
<212> TYPE: DNA
<213> ORGANISM: Artificial
<220> FEATURE:
<223> OTHER INFORMATION: Uncultured Methylobacillus sp. clone JER103 16S
    ribosomal RNA gene, partial sequence

<400> SEQUENCE: 32

| | |
|---|---|
| attgaacgct ggcggaatgc tttacacatg caagtcgaac ggaacttagg ggcttgctcc | 60 |
| taagtttagt ggcgaacggg tgagtaatat atcggaacgt atccattaat ggggataac | 120 |
| taatcgaaag gttggctaat accgcatacg ccctacgggg gaaagcaggg gatcttcgga | 180 |
| ccttgcgtta atggagcggc cgatatctga ttagctagtt ggtgaggtaa aggctcacca | 240 |
| aggcgacgat cagtagctgg tctgagagga cgaccagcca cactggaact gagacacggt | 300 |
| ccagactcct acgggaggca gcagtgggga attttggaca atgggcgaaa gcctgatcca | 360 |
| gccattccgc gtgagtgaag aaggccttcg ggttgtaaag ctctttcgca agggaagaaa | 420 |
| acttatattc taataaagta tgaggatgac ggtaccttga taagaagcac cggctaacta | 480 |
| cgtgccagca gccgcggtaa tacgtagggt gcgagcgtta atcggaatta ctgggcgtaa | 540 |
| agcgtgcgca ggcggttttg aaagtcagat gtgaaatccc cgagctcaac ttgggaactg | 600 |
| cgtttgaaac tccaaagcta gagtatagga gaggggggta gaattccacg tgtagcagtg | 660 |
| aaatgcgtag agatgtggag gaataccaat ggcgaaggca gccccctggc ctaatactga | 720 |
| cgctcatgca cgaaagcgtg gggagcaaac aggattagat accctggtag tccacgccct | 780 |

```
aaacgatgtc tactagttgt tggtggagta aaatccatta gtaacgcagc taacgcgtga    840
agtagaccgc ctggggagta cggtcgcaag attaaaactc aaatgaattg acggggcccc    900
gcacaagcgg tggattatgt ggattaattc gatgcaacgc gaaaaacctt acctggcctt    960
gacatgccac taacgaagca gagatgcatt aggtgctcga agagaaagt ggacacaggt    1020 gctgcatggt tgtcgtcagc tcgtgtcgtg agatgttggg ttaagtcccg caacgagcgc    1080
aacccttgtc gttaattgcc atcatttagt tgggcacttt aacgagactg ccggtgacaa    1140
accggaggaa ggtggggatg acgtcaagtc ctcatggccc ttatggccag ggcttcacac    1200
gtaatacaat ggtcggtaca gagggttgcc aacccgcgag ggggagccaa tcccagaaag    1260
ccgatcgtag tccggattgc agtctgcaac tcgactgcat gaagtcggaa tcgctagtaa    1320
tcgcggatca gcatgtcgcg gtgaatacgt tcccgggcct tgtacacacc gcccgtcaca    1380
ccatgggagt gggtttcacc agaagtaggt agtctaaccg caaggggac gcttaccacg     1440 gtgggattca tgactggg                                                  1458
```

<210> SEQ ID NO 33
<211> LENGTH: 1443
<212> TYPE: DNA
<213> ORGANISM: Artificial
<220> FEATURE:
<223> OTHER INFORMATION: Uncultured Pseudomonas sp. clone JER122 16S
      ribosomal RNA gene, partial sequence

<400> SEQUENCE: 33

```
gaacgctggc ggcaggccta acacatgcaa gtcgagcgga tgaggagagc ttgctctccg    60
attcagcggc ggacgggtga gtaatgccta ggaatctgcc tggtagtggg ggacaacgtt    120
tcgaaaggaa cgctaatacc gcatacgtcc tacgggagaa agtgggggat cttcggacct    180
cacgctatca gatgagccta ggtcggatta gctagttggt ggggtaatgg cctaccaagg    240
cgacgatccg taactggtct gagaggatga tcagtcacac tggaactgag acacggtcca    300
gactcctacg ggaggcagca gtggggaata ttggacaatg ggcgaaagcc tgatccagcc    360
atgccgcgtg tgtgaagaag gtcttcggat tgtaaagcac tttaagctgg gaggaagggc    420
tgctggttaa taccctgcag ttttgacgtt accaacagaa taagcaccgg ctaacttcgt    480
gccagcagcc gcggtaatac gaagggtgca agcgttaatc ggaattactg ggcgtaaagc    540
gcgcgtaggt ggttgggtaa gttgaatgtg aaagccccgg gctcaacctg gaactgcat    600 ccaaaactgc ccggctagag tacggtagag ggtggtggaa tttcctgtgt agcggtgaaa    660
tgcgtagata taggaaggaa caccagtggc gaaggcgacc acctggactg atactgacac    720
tgaggtgcga aagcgtgggg agcaaacagg attagatacc ctggtagtcc acgccgtaaa    780
cgatgtcgac tagccgttgg gctccttgag agcttggtgg cgcagctaac gcattaagtc    840
gaccgcctgg ggagtacggc cgcaaggtta aaactcaaat gaattgacgg ggcccgcac    900 aagcggtgga gcatgtggtt taattcgaag caacgcgaag aaccttacct ggccttgaca    960
tcctgcgaac ctttcagaga tgagaggtgt ccttcgggaa cgcagagaca ggtgctgcat    1020
ggctgtcgtc agctcgtgtc gtgaggtgtt gggttaagtc ccgtaacgag cgcaaccctt    1080
gtccttagtt accagcacct cgggtgggca ctctaaggag actgccggtg acaaaccgga    1140
ggaaggtggg gatgacgtca agtcatcatg gcccttacgg ccagggctac acacgtgcta    1200
caatggtcgg tacagagggt tgccaagccg cgaggtggag ctaatcccag aaaaccgatc    1260
gtagtccgga tcgcagtctg caactcgact gcgtgaagtc ggaatcgcta gtaatcgcga    1320
```

| | |
|---|---:|
| atcagaatgt cgcggtgaat acgttcccgg gccttgtaca caccgcccgt cacaccatgg | 1380 |
| gagtgggttg ctccagaagt agctagtcta accttcgggg gacggttac cacggagtat | 1440 |
| tca | 1443 |

<210> SEQ ID NO 34
<211> LENGTH: 1416
<212> TYPE: DNA
<213> ORGANISM: Artificial
<220> FEATURE:
<223> OTHER INFORMATION: Uncultured proteobacterium clone LPL86 16S
 ribosomal RNA gene, partial sequence

<400> SEQUENCE: 34

| | |
|---|---:|
| aacgctggcg gcgtgcctaa tacatgcaag tcgaacgggg aagtaccttc gggtattgta | 60 |
| ctagtggcgg acgggtgagt aacacgtggg taatctgccc tcgagcgggg aataaccagt | 120 |
| cgaaagattg gctaataccg cataagacca caatctctgc ggagaaaggg gtcaaaggct | 180 |
| tcggccactc gaggatgagc ctgcgcccga ttagttagtt ggtgaggtaa tggctcacca | 240 |
| agacgatgat cggtagctgg tctgagagga tgatcagcca cattgggact gagacacggc | 300 |
| ccaaactcct acgggaggca gcagtaggga atattgcgca atgaaggaaa ctctgacgca | 360 |
| gcgacgccgc gtgagtgatg aaggctttcg ggttgtaaag ctctgttctc agggaaaaag | 420 |
| aaagtgatga tacctgagaa gaaaggaccg gctaacttcg tgccagcagc cgcggtaaga | 480 |
| cgggggtcc aagcgttgct cggaatcatt gggcgtaaag gggcgtagg tggctttgta | 540 |
| agtcagaagt gaaagccctg gctcaaccc gggaagtgct tttgatactg cgaagcttga | 600 |
| atgtggtaga ggatagtaga attcctagtg tagtggtgaa atacgtagat attaggagga | 660 |
| atacctgtgg cgaaggcggc tatctggacc aacattgaca ctgaggcccg aaagcgtggg | 720 |
| gatcaaacag gattagatac cctggtagtc cacgccgtaa acgatggata cttgttgttg | 780 |
| gtggtattga ccccatcagt gacgaagcta acgcgttaag tatcccgcct ggggagtacg | 840 |
| gtcgcaagat taaaactcaa agaaattgac ggggggcccgc acaagcggtg gagcatgtgg | 900 |
| tttaattcga tgcaacgcga agaaccttac ctaggtttga catctactgg aagaatctca | 960 |
| gaaatgagtt cgccttcggg ccggtagaca ggtgctgcat ggctgtcgtc agctcgtgtc | 1020 |
| gtgagatgtt gggttaagtc ccgcaacgag cgcaaccctc gtgtttagtt gccagcattt | 1080 |
| agttgggcac tctaaacaga ctgccgacgt taagtcggag gaaggtgggg atgacgtcaa | 1140 |
| gtcctcatgg cctttatatc tagggctaca cacgtgctac aatggtcggt acagagggaa | 1200 |
| gccaaatagt aatatggagc caatccctta aagccgatct aagttcagat tgaggtctgc | 1260 |
| aactcgacct catgaaggtg gaatcgctag taatcgcgga tcagaacgcc gcggtgaata | 1320 |
| cgttcccggg ccttgtacac accgcccgtc acaccatgaa agttggtcgt accagaagtc | 1380 |
| gctgcgctaa ccgtaaggga gcaggcgccc aaggta | 1416 |

<210> SEQ ID NO 35
<211> LENGTH: 1396
<212> TYPE: DNA
<213> ORGANISM: Artificial
<220> FEATURE:
<223> OTHER INFORMATION: Uncultured Rhizobiales bacterium clone LPR22
 16S ribosomal RNA gene, partial sequence

<400> SEQUENCE: 35

| | |
|---|---:|
| acgctggcgg caggcttaac acatgcaagt cgagcggccg tagcaatacg gcagcggcag | 60 |
| acgggagagt aacacgtggg aacgtgccca tcagttcgga acaacccagg gaaacttggg | 120 |

```
ctaataccgg atacgccctt acggggaaag atttatcgct gatggagcgg cccgcgtctg        180
attagctagt tggtgaggta acggctcacc aaggcgacga tcagtagctg gtctgagagg        240
atgatcagcc tcattgggac tgagacacgg cccaaactcc tacgggaggc agcagtgggg        300
aatattggac aatgggcgca agcctgatcc agccatgccg cgtgggtgat gaaggcccta        360
gggttgtaaa gcccttcgg cggggaagat aatgacggta cccgcagaag aagccccggc         420
taacttcgtg ccagcagccg cggtaatacg aaggggcta cgttgctcg gaatcactgg          480 gcgtaaagcg cacgtaggcg gcttttttaag tcaggggtga atcctggag ctcaactcca        540 gaactgcctt tgatactgag aagcttgagt tcggagagg tgagtggaac tgcgagtgta         600
gaggtgaaat tcgtagatat tcgcaagaac accagtggcg aaggcggctc actggcccga       660
tactgacgct gaggtgcgaa agcgtgggga gcaaacagga ttagataccc tggtagtcca       720
cgctgtaaac gatggatgct agccgttggt gggtttaccc ttcagtggcg cagctaacgc      780
attaagcatc ccgcctgggg agtacggtcg caagattaaa actcaaagga attgacgggg      840
gcccgcacaa gcggtggagc atgtggttca attcgaagca acgcgcagaa ccttaccagc     900
ccttgacatg tcccgtatga gcaccggaga cggagctctt cagttcggct ggcgggaaca    960
caggtgctgc atggctgtcg tcagctcgtg tcgtgagatg ttgggttaag tcccgcaacg    1020
agcgcaaccc tcgcccttag ttgccatcat tcagttgggc actctaaggg gactgccggt    1080
gataagccgg aggaaggtgg ggatgacgtc aagtcctcat ggcccttacg ggctgggcta   1140
cacacgtgct acaatggcgg tgacagtggg atgcaatgga gcgatcctgc gcaaatctca    1200
aaaagccgtc tcagttcgga ttgtgctctg caactcgagc acatgaagtt ggaatcgcta    1260
gtaatcgcag atcagcacgc tgcggtgaat acgttcccgg gccttgtaca caccgcccgt    1320
cacaccatgg gagttggctt tacctgaagg cggtgcgcta acccgcaagg gaggcagccg    1380
accacggtag ggtcag                                                    1396

<210> SEQ ID NO 36
<211> LENGTH: 1408
<212> TYPE: DNA
<213> ORGANISM: Artificial
<220> FEATURE:
<223> OTHER INFORMATION: Uncultured cyanobacterium clone LPR90 16S
      ribosomal RNA gene, partial sequence

<400> SEQUENCE: 36
aacgctggcg gtatgcttac acatgcaagt cgaacggaaa tagcttcggt tagtttttagt       60 ggcggacggg tgagtaacac gtgagaattc gcctttagga gggggataac ggatggaaac      120
attcgctaaa acctcatatg cccctgggtg aaacagagga gataagtaat actgactcac      180
ctctgcctga agagaagctc gcggctgatt agctagttgg tagggtaaag gcctaccaag      240
gcgacgatca gtagctggtc tgagaggacg atcagccaca ctggaactga gacacgtcc       300 agactcctac gggaggcagc agtgaggaat tttctgcaat gggcgaaagc ctgacagagc      360
aataccgcgt gagggatgaa gacttactga gttgtaaacc tcggtacctt aaggaagaag      420
atctgacggt acttaaggtg gaaagcatcg gctaactccg tgccagcagc cgcggtaaga      480
cgggggatgc aagtgttatc ggatttact gggcgtaaag cgtctgcagg tggtttctta       540
agtctactgt taaatcttga ggctcaacct caaatctgca gtagaaacta ggagacttga     600
gtatagtagg ggtagaggga atttccagtg gagcggtgaa atgcgtagat attggaaaga    660
acaccgatgc cgaaggcact ctactgggcc attactgaca ctcagagacg aaagctaggg    720
gagcaaatgg gattagatac cccagtagtc ctagccgtaa acgatggata ctcgatgttg    780
```

```
gacgtatcga cccgttcagt atcttagcta acgcgttaag tatcccgcct ggggagtacg    840
ctcgcaagag tgaaactcaa aggaattgac gggggcccgc acaagcggtg gaggatgtgg    900
tttaattcga tgcaacgcga agaaccttac cagggtttgc tagaagtgtt ggttttctga    960
aaagaattcc ttattccgct tctacaggtg gtgcatggct gtcgtcagct cgtgtcgtga   1020
gatgttgggt taagtcccgc aacgagcgca acccttattt ttagttctat tgtctagaaa   1080
gactgccggt gacaaaccgg aggaaggtga ggacgacgtc aagtcatcat gccccttaca   1140
ccctgggcta cacacgtcct acaatgggta agacaataag ttgcaaattc gcgagaataa   1200
gctaatcttt gaaacttact ccaagtacag attgcaggct gcaactcgcc tgcatgaagg   1260
tggaatcgct agtaatcgct ggtcagctac acagcggtga atccgttccc gggccttgta   1320
cacaccgccc gtcacaccat ggaagctggt tgtacccgaa gtcgttatcc taaccgtaag   1380
gaaggagatg ccgaaggtaa aattagta                                       1408

<210> SEQ ID NO 37
<211> LENGTH: 1414
<212> TYPE: DNA
<213> ORGANISM: Artificial
<220> FEATURE:
<223> OTHER INFORMATION: Uncultured Corynebacterium sp. clone MPL67 16S
      ribosomal RNA gene, partial sequence

<400> SEQUENCE: 37
gaacgctggc ggcgtgctta acacatgcaa gtcgaacgga aaggcccagc ttgctggggt     60
gctcgagtgg cgaacgggtg agtaacacgt gggtgatctg ccctgcactt cgggataagc    120
ttgggaaact gggtctaata ccggatagga ccatcgttta gtgtcggtgg tggaaagttt    180
tttcggtgtg ggatgagctc gcggcctatc agcttgttgg tggggtaatg gcctaccaag    240
gcgtcgacgg gtagccggcc tgagagggcg tacggcccaca ttgggactga gatacgccc    300 agactcctac gggaggcagc agtggggaat attgcacaat gggcgcaagc ctgatgcagc    360
gacgccgcgt gggggatgac ggccttcggg ttgtaaactc ctttcgccaa ggacgaagct    420
tttaagtgac ggtacttgga gaagaagcac cggctaacta cgtgccagca gccgcggtaa    480
tacgtagggt gcgagcgttg tccggaatta ctgggcgtaa agagctcgta ggtggtttgt    540
cgcgtcgttt gtgtaagtcc gcagcttaac tgagggactg caggcgatac gggcataact    600
tgagtgctgt agggagact ggaattcctg gtgtagcggt ggaatgcgca gatatcagga    660
ggatcaccga tggcgaaggc aggtctctgg gcagtaactg acgctgagga gcgaaagcat    720
ggggagcgaa caggattaga taccctggta gtccatgccg taaacggtgg gcgctaggtg    780
tgagtccctt ccacggggtt cgtgccgtag ctaacgcatt aagcgccccg cctggggagt    840
acggccgcaa ggctaaaact caaaggaatt gacggggggcc cgcacaagcg gcggagcatg    900
tggattaatt cgatgcaacg cgaagaacct tacctgggct tgacatacac cggacgggc    960 cagagatggt ctttcccttt gtggctggtg tacaggtggt gcatggttgt cgtcagctcg   1020
tgtcgtgaga tgttgggtta agtcccgcaa cgagcgcaac ccttgtctta tgttgccagc   1080
acttcgggtg gggactcata agagactgcc ggggttaact cggaggaagg tggggatgac   1140
gtcaaatcat catgcccctt atgtccaggg cttcacacat gctacaatgg tcggtacaac   1200
gcgtgtgcta cttcgtgaga aggtgctaac cgctctaaag ccggccttag ttcggattgg   1260
ggtctgcaac tcgaccccat gaagtcggag tcgctagtaa tcgcagatca gcaacgctgc   1320
ggtgaatacg ttcccgggcc ttgtacacac cgcccgtcac gtcatgaaag ttggtaacac   1380
```

```
ccgaagccag tggcccaaac tcgtgtaggg agct                              1414
```

<210> SEQ ID NO 38
<211> LENGTH: 1424
<212> TYPE: DNA
<213> ORGANISM: Artificial
<220> FEATURE:
<223> OTHER INFORMATION: Uncultured Hymenobacter sp. clone PR8 16S
      ribosomal RNA gene, partial sequence <400> SEQUENCE: 38

```
tgaacgctag cggcaggcct aatacatgca agtcgaacgg tggcagcaat gccatagtgg    60
cgcacgggtg cgtaacgcgt aaccaacctg ccctgaactg ggggatagcc cgccgaaagg   120
cggattaata ccgcataatc taaggtggcg gcatcgtctc tttagtaaag atttattggt   180
tcaggatggg gttgcgcgcc attagctagt tggggggta acggcccacc aaggcgacga   240
tggctagggg agctgagagg ctggtccccc acacgggcac tgagatacgg gcccgactcc   300
tacgggaggc agcagtaggg aatattgggc aatgggcgag agcctgaccc agccatgccg   360
cgtgcaggat gaaggctttc tgagtcgtaa gctgcttttg ccagggaaga aaaaagggga   420
tgcgtcctct actgacggta cctggtgaat aagcaccggc taactccgtg ccagcagccg   480
cggtaatacg gagggtgcaa gcgttgtccg gatttattgg gtttaaaggg tgcgtaggcg   540
gttctttaag tctggggtga aagcccgttg ctcaacaacg gaactgccct ggaaactggc   600
gaacttgagt acagacgagg gcggcggaat ggatggtgta gcggtgaaat gcatagatac   660
catccagaac cccgatctgc gaaggcagct gcctagactg taactgacgc tgaggcacga   720
aagcgtgggg agcgaacagg attagatacc ctggtagtcc acgccgtaaa cgatggatac   780
tcgctgccgg cgatacaatg tcggtggctt agcgaaagcg ttaagtatcc cacctgggga   840
gtacgcccgc aagggtgaaa ctcaaaagaa ttgacggggg cccgcacaag tggtggagca   900
tgtggtttaa ttcgatgata cgcgaggaac cttacctagg ctagaatgcg cgtgaccgcg   960
ccagagatgg cgctttcctt cgggacacaa agcaaggtgc tgcatggccg tcgtcagctc  1020
gtgccgtgag gtgttgggtt aagtcccgca acgagcgcaa ccctacatt tagttgccag  1080
cggataatgc cggggactct agatggactg cctgcgcaag cagtgaggaa ggcggggacg  1140
atgtcaggtc atcatggccc ttacgcctag ggctacacac gtgctacaat ggacggtaca  1200
gcgggttgcc aaccagcgat ggtgcgccaa tcccgaaaag ccgttctcag ttcggatcgg  1260
agtctgcaac tcgactccgt gaagctggaa tcactagtaa tcgcgtatca gcaatgacgc  1320
ggtgaatacg ttcccgggcc ttgtacaccg cccgtcaagc catggaagtt tggtagacct  1380
gaagccggtg ctcgtcacag aagccggtta gggtagaaca ggta                   1424
```

<210> SEQ ID NO 39
<211> LENGTH: 1458
<212> TYPE: DNA
<213> ORGANISM: Artificial
<220> FEATURE:
<223> OTHER INFORMATION: Uncultured Veillonella sp. clone PR40 16S
      ribosomal RNA gene, partial sequence <400> SEQUENCE: 39

```
ggcggcgtgc attaacacat gcaagtcgaa cggacggaca gggagcttgc tcccttgaag    60
ttagcggcga acgggtgagt aacgcgtaat caacctgccc ttcagagggg gataacaacg   120
ggaaaccgtt gctaataccg cgtacgattc acgaatggca tcatttgtga atgaaaggtg   180
gcctctattt ataagctacc gctgaaggag gggattgcgt ctgattagct agttggaggg   240
```

| | |
|---|---|
| gagacggccc accaaggcaa tgatcagtag ccggtctgag aggatgaacg gccacattgg | 300 |
| gactgagaca cggcccaaac tcctacggga ggcagcagtg gggaatcttc cgcaatggac | 360 |
| gaaagtctaa cggagcaacg ccgcgtgagt gatgaaggtc ttcggattgt aaagctctgt | 420 |
| taatcgggac gaaagatctt tgcgtgaata atgcagaaaa gcgacggtac cggaatagaa | 480 |
| agccacggct aactacgtgc cagcagccgc ggtaatacgt aggtggcaag cgttgtccgg | 540 |
| aattattggg cgtaaagcgc gcgcaggcgg cccatccagt ctgccttaaa agctcggggc | 600 |
| tcaaccccgt gatgggatgg aaactagcag gctagagcat cggagaggaa agcggaattc | 660 |
| ctagtgtagc ggtgaaatgc gtagatatta ggaagaacac cagtggcgaa ggcggctttc | 720 |
| tggacgaaaa ctgacgctga ggcgcgaaag ccaggggagc gaacgggatt agataccccg | 780 |
| gtagtcctgg ccgtaaacga tgggactag gtgtaggagg tatcgacccc ttctgtgccg | 840 |
| gagttaacgc aataagtacc ccgcctgggg agtacggtcg caaggctgaa actcaaagga | 900 |
| attgacgggg gcccgcacaa gcggtggagt atgtggttta attcgacgca acgcgaagaa | 960 |
| ccttaccagg tcttgacatt gatggacgaa acaagagatt gttttctcc ttcgggagcc | 1020 |
| agaaaacagg tggtgcacgg ctgtcgtcag ctcgtgtcgt gagatgttgg gttaagtccc | 1080 |
| gcaacgagcg caacccctat cttatgttgc cagcacttcg ggtgggaact catgagagac | 1140 |
| tgccgcagac aatgcggagg aaggcgggga tgacgtcaag tcatcatgcc cttatgacc | 1200 |
| tgggctacac acgtactaca atgggcttta atagagggaa gcaagccgc gaggtggagc | 1260 |
| aaacccccaga aacaagctct cagttcggat cgtaggctgc aactcgccta cgtgaagtcg | 1320 |
| gaatcgctag taatcgcagg tcagcatact gcggtgaata cgttcccggg ccttgtacac | 1380 |
| accgcccgtc acaccacgaa agtcggaagt acccaaagcc ggtggggtaa ccttcgggag | 1440 |
| ccagccgtct aaggtaaa | 1458 |

<210> SEQ ID NO 40
<211> LENGTH: 1410
<212> TYPE: DNA
<213> ORGANISM: Artificial
<220> FEATURE:
<223> OTHER INFORMATION: Uncultured Flexibacteraceae bacterium clone
    GL2-5 16S ribosomal RNA gene, partial sequence

<400> SEQUENCE: 40

| | |
|---|---|
| cgctagcggc aggcctaata catgcaagtc gagcgggtag caataccagc ggcaaacggg | 60 |
| tgcgtaacgc gtaaataacc tgccctcaac tgggagatag ctttgcgaaa gcggaggtaa | 120 |
| taccccatag tcttttgggt ccacctggac tgattagtaa agcagcaatg tggttgagga | 180 |
| gggatttgcg tctgattagt tagttggcag ggtagtggcc taccaagacg atgatcagtc | 240 |
| ggggctctga gaggagggtc ccccacatgg gcactgagac acgggcccaa ctcctacggg | 300 |
| aggcagcagt agggaatatt gggcaatggg cggaagcctg acccagccat gccgcgtgcc | 360 |
| ggatgaaggc ccgctgggtt gtaaacggct tttatctggg aagaagagca gggatgcgtc | 420 |
| cctgcgtgac ggtaccagag gaatcagcac cggctaactc cgtgccagca gccgcggtaa | 480 |
| tacgagggt gcaagcgttg tccggattta ttgggtttaa agggtgcgta ggtggttggt | 540 |
| taagtcagct ttgaaagtgg gtcgcttaac gacacagggt gggttgatac tggccaactt | 600 |
| gaatgggatg gaggttactg gaacgggtcg tgtagcggtg aaatgcatag atatgaccca | 660 |
| gaactccaat tgcgaaggca ggtggctaca ttccgattga cactgaggca cgagagcatg | 720 |
| gggagcaaac aggattagat accctggtag tccatgccgt aaacgatgat aactgactgt | 780 |
| gtgattttcg gattgcgtgg ttaagcgaaa gcgttaagtt atccacctgg ggagtacgcc | 840 |

```
ggcaacggtg aaactcaaag gaattgacgg gggtccgcac aagcggtgga gcatgtggtt     900
taattcgatg atacgcgagg aaccttaccc ggattagaat gcgcgtgaag ggcttggaga     960
caggtccgtc tagcaataga cacaaagcaa ggtgctgcat ggctgtcgtc agctcgtgcc    1020
gtgaggtgtt gggttaagtc ccgcaacgag cgcaaccect ggaatcagtt gccagcacgt    1080
caaggtgggg actctggttc gactgcctgc gcaagcagag aggaaggcgg ggacgacgtc    1140
aagtcatcat ggcccttaca tccggggcga cacacgtgct acaatggccg gtacagcggg    1200
tcacgatccc gcaaggggga gtcaatctca gcaaagccgg tcacagttcg gattggggtc    1260
tgcaactcga ccccatgaag ctggaatcgc tagtaatcgc gcatcagcca tggcgcggtg    1320
aatacgttcc cggaccttgt acacaccgcc cgtcaagcca tgggagtcgg gggacctga     1380
agcggggggt tacatccctc aagggtaaat                                     1410
```

<210> SEQ ID NO 41
<211> LENGTH: 1382
<212> TYPE: DNA
<213> ORGANISM: Artificial
<220> FEATURE:
<223> OTHER INFORMATION: Uncultured candidate division TM7 bacterium clone GL2-37 16S ribosomal RNA gene, partial sequence

<400> SEQUENCE: 41

```
gaacgctggc ggagtgccta atacatgcaa gtcgagcggc agcgcgtcta gtttactaga      60
tggcggcgag cggcggacgg ctgagtaacg cgtgggaacg tgcccaaag tgaggaataa      120
ctgcccgaaa gggtagctaa tgccgcatat ggtcttcgga ttaaaggatt tatccgcttt     180
gggagcggcc cgcgtacgat tagatagttg gtgaggtaat ggctcaccaa gtcgacgatc     240
gttagctggt ctgagaggat gaccagccag actggaactg agacacggtc cagactccta     300
cgggaggcag cagtaaggaa tcttccacaa tggacgaaag tctgatggag caactccgcg     360
tgcaggacga aggccctcgg gtcgtaaact gcttttatga gtgaagaata tgacggtaac     420
tcatgaataa gggtcggcta actacgtgcc agcagccgcg gtcatacgta ggacccaagc     480
gttatccgga gtgactgggc gtaaagagtt gcgtaggtgg tcggtaaagt gaatagtgaa     540
atctggtggc tcaaccatac agactattat tcaaactcac cgactcgaga atggtagagg     600
taactggaat ttcttgtgta ggagtgaaat ccgtagatat aagaaggaac accaatggcg     660
taggcaggtt actggaccat ttctgacact gaggcacgaa agcgtgggga gcgaaccgga     720
ttagataccc gggtagtcca cgccgtaaac gatggatact agctgttgga ggtatcgacc     780
ccttcagtag cgaagctaac gcgttaagta tcccgcctgt ggagtacggt cgcaagacta     840
aaacataaag gaattgacgg gacccgcac aagcggtgga tcgtgttctt taattcgatg     900
ataaacggag aaccttacca gggcttgaca tccttggaat tactgcgaaa gcagttagtg     960
cctttttggaa ccaagtgaca ggtgttgcat ggccgtcgtc agctcgtgtc gtgagatgtt    1020
aggttaagtc ctttaacgag cgcaacccctt gtgatagtt gtatttttct attcagactg    1080
ccccggcaac ggggaggaag gaggggatga ggtcaggtca gtattaccct tacgccctgg    1140
gctagaaaca cgatacaatg gctagtacaa tgcgcagcga agccgcgagg tggagcaaat    1200
cgcatcaaag ctagtcccag ttcggattgg aggctgaaac tcgcctccat gaagtcggaa    1260
tcgctagtaa tcgcaaatca gcaagttgcg gtgaatacgt tcccgggtct tgtacacacc    1320
gcccgtcaaa ccatgaaagt gaccaacacc cgaagtccga ttcgtcggcc taaggtgggg    1380
gg                                                                  1382
```

<210> SEQ ID NO 42
<211> LENGTH: 1405
<212> TYPE: DNA
<213> ORGANISM: Artificial
<220> FEATURE:
<223> OTHER INFORMATION: Uncultured Deinococcus sp. clone GL2-41 16S
      ribosomal RNA gene, partial sequence

<400> SEQUENCE: 42

```
tgaacgctgg cggcgtgctt aagacatgca agtcgaacgg tctcttcgga gacagtggcg     60
cacgggtgag taacacgtaa ctgacctgcc ccaaagtcgc ggataacggg ccgaaaggtt    120
cgctaatacg tgatgtgctg tcagattttg ttctgctagt aaaggtttac tgctttggga    180
tggggttgcg ttccatcagc ttgttggtgg ggtaaaggcc taccaaggcg acgacggata    240
gccggcctga gagggtggcc ggccacaggg gcactgagac acgggtccca ctcctacggg    300
aggcagcagt taggaatctt ccacaatggg cgaaagcctg atggagcgac gccgcgtgag    360
ggatgaaggt tctcggatcg taaacctctg aactagggac gaaagacacg taagtgggat    420
gacggtacct aggtaatagc accggctaac tccgtgccag cagccgcggt aatacggagg    480
gtgcaagcgt tacccggaat cactgggcgt aaagggcgtg taggcggtga tttaagtctg    540
gttttaaaga ccggggctca acctcgggaa tggactggat actggatcac ttgacctctg    600
gagaggtaac tggaattcct ggtgtagcgg tggaatgcgt agataccagg aggaacacca    660
atggcgaagg caagttactg gacagaaggt gacgctgagg cgcgaaagtg tggggagcga    720
accggattag atacccgggt agtccacacc ctaaacgatg tacgttggct gaccgcagga    780
tgctgtggtt ggcgaagcta acgcgataaa cgtaccgcct gggaagtacg gccgcaaggt    840
tgaaactcaa aggaattgac gggggcccgc acaagcggtg gagcatgtgg tttaattcga    900
agcaacgcga agaaccttac caggtcttga catcccaaga acctcccaga gatggaaggg    960
tgcccttcgg ggaacttgga gacaggtgct gcatggctgt cgtcagctcg tgtcgtgaga   1020
tgttgggtta agtcccgcaa cgagcgcaac ccttacctcc agttgccagc attcagttgg   1080
gcactctgga gggactgcct atgaaagtag gaggaaggcg gggatgacgt ctagtcagca   1140
tggtccttac gacctgggcg acacacgtgc tacaatggcc aggacaacgc gcagccagct   1200
cgcgagagtg cgcgaatcgc tgaaacctgg ccccagttca gatcggagtc tgcaactcga   1260
ctccgtgaag ttggaatcgc tagtaatcgc gggtcagcat accgcggtga atacgttccc   1320
gggccttgta cacaccgccc gtcacaccat gggagtaagt tgcagttgaa accgccggga   1380
gctgtaaggc aggcgtctag actgt                                         1405
```

<210> SEQ ID NO 43
<211> LENGTH: 1439
<212> TYPE: DNA
<213> ORGANISM: Artificial
<220> FEATURE:
<223> OTHER INFORMATION: Uncultured Alkanindiges sp. clone GL2-47 16S
      ribosomal RNA gene, partial sequence

<400> SEQUENCE: 43

```
tgaacgctgg cggcaggctt aacacatgca agtcgaacgg attgatgtac ttgtacattg     60
attagtggcg aacgggtgag taatgcctag gaatctgcca tttagtgggg gacaacattt    120
cgaaaggaat gctaataccg catacgccct acggggggaaa gaggggggacc gcaaggcctc    180 ttgctaaatg atgagcctag gtcggattag ctagttggtg gggtaaaggc tcaccaaggc    240
gacgatctgt agcgggtctg agaggatgat ccgccacact ggaactgaga cacggtccag    300
```

```
actcctacgg gaggcagcag tggggaatat tggacaatgg gggcaaccct gatccagcca       360
tgccgcgtgt gtgaagaagg ccttttggtt gtaaagcact ttaagcgggg aggaggctct       420
tggtgttaat agcactgatg agcggacgtt acccgcagaa taagcaccgg ctaactctgt       480
gccagcagcc gcggtaatac agagggtgcg agcgttaatc ggaattactg ggcgtaaagc       540
gcgcgtaggc ggtttattaa gtcggatgtg aaatccccgg gctcaacctg ggaattgcat       600
tcgatactgg taggctagag tatgggagag aaggtagaa ttccaggtgt agcggtgaaa        660
tgcgtagaga tctggaggaa taccgatggc gaaggcagcc ttctggccta atactgacgc       720
tgaggtgcga aagcatgggg agcaaacagg attagatacc ctggtagtcc atgccgtaaa      780
cgatgtcaac tagccgttgg gggatttgat cctttagtgg cgcagctaac gcgataagtt      840
gaccgcctgg ggagtacggt cgcaagacta aaactcaaat gaattgacgg gggcccgcac     900
aagcggtgga gcatgtggtt taattcgatg caacgcgaag aaccttacct ggtcttgaca      960
tagtgagaac gatccagaga tggattgtg ccttttagga attcacatac aggtgctgca      1020
tggctgtcgt cagctcgtgt cgtgagatgt tgggttaagt cccgcaacga gcgcaaccct     1080
tttccttatt tgccagcggg tcatgccggg aactctaagg atactgccag tgacaaactg    1140
gaggaaggcg gggacgacgt caagtcatca tggcccttac gaccagggct acacacgtgc    1200
tacaatggtc ggtacaaagg gttgctagac cgcgaggtca tgctaatctc aaaaagccga    1260
tcgtagtccg gattggagtc tgcaactcga ctccatgaag tcggaatcgc tagtaatcgc    1320
ggatcagaat gccgcggtga atacgttccc gggccttgta cacaccgccc gtcacaccat   1380
gggagtttgt tgcaccagaa gtaggtagtc taaccttagg ggggacgctt accacggtg    1439
```

<210> SEQ ID NO 44
<211> LENGTH: 1411
<212> TYPE: DNA
<213> ORGANISM: Artificial
<220> FEATURE:
<223> OTHER INFORMATION: Uncultured cyanobacterium clone GL2-53 16S ribosomal RNA gene, partial sequence

<400> SEQUENCE: 44

```
gaacgctggc ggtgtgttaa cacatgcaag tcgaacgaac tcttcggagt tagtggcgga        60
cgggtgagta atacatagat aatctgcctt aaagtgggg ataactagcc gaaaggttag       120
ctaataccgc ataatgtagt tagttgaaat actaattaag aaaggattta ttcgcttata      180
gaggagtcta tggttgatta gctagttggt agggtaatgg cttaccaagg cgatgatcaa      240
tagctggtct gagaggacga tcagccacac tgggactgag acacggccca gacttctacg      300
gaaggcagca gtggggaatt ttccgcaatg gacgaaagtc tgacggagcg acaccgcgtg       360
ggggatgaag tatttaggta tgtaaacccc ttttggcagg aatgaaaaaa atgacagtac       420
ctgcagaata agcatcggct aactacgtgc cagcagccgc ggtaatacgt aggatgcaag       480
cgttgttcgg aattactggg cgtaaagagt acgtaggcgg caatgtaagt ctgatattaa       540 agactgggc ttaacctcag gagtgtatcg gaaactacat agctagagga cagtagagga       600
agtcggaatt ctcagtgtag cggtgaaatg cgtagatatt ggaagaaca ccggtggcga       660 aagcggactt ctgggctgtt actgacgctg aggtacgaaa gcgtggggag caaacaggat      720
tagataccct ggtagtccac gcggtaaacg atggatacta ggtgtaactg gcttcgaccc     780
cagttgtgcc gcagctaacg cattaagtat cccgcctggg gagtatggcc gcaaggttga     840
aactcaaagg aattgacggg ggcccgcaca agcggtggag gatgtggttt aattcgacgc    900
aacgcgaaga accttaccaa ggcttgacat ccactgaatc tagtagaaat attggagtgc    960
```

-continued

```
ccgcaaggga gcagtgagac aggtggtgca tggctgtcgt cagctcgtgt cgtgagatgt      1020
tgggttaagt cccgcaacga gcgcaaccct cgatgctagt taccatcatt tagttgggga      1080
ctctagcgtg actgccggag ctaatccgga ggaaggtgag gacgacgtca agtcatcatg      1140
ccccttacgt cctgggctac acacgtccta caatggtata gacaaagagc tgcaagttag      1200
tgatagcaag cgaatctcat aaactatatc tcagttcgga ctgtaggctg caactcgcct      1260
acatgaagtt ggaatcgcta gtaaccgtag atcagcatgc tacggtgaat acgttcccgg      1320
gccttgtaca caccgcccgt cacaccacga aagtttgtca tacccgaaac cgatgggcta      1380
accgcaagga ggcagtcgtc taaggtaggg c                                    1411
```

<210> SEQ ID NO 45
<211> LENGTH: 1386
<212> TYPE: DNA
<213> ORGANISM: Artificial
<220> FEATURE:
<223> OTHER INFORMATION: Uncultured candidate division TM7 bacterium
      clone GL2-61 16S ribosomal RNA gene, partial sequence

<400> SEQUENCE: 45

```
tgaacgctgg cggcgtgcct aacacatgca agtcgagacg gcagcgcgtc tagtttacta        60
gatggcggcg agcggcggac ggctgagtaa cgcgtgggaa gtgtgcccta aagtgaggga       120
taacgcaccg aaagggtgtg ctaataccgc atatggtctt cggattaaag gatttatccg       180
ctttaggacc agcccgcgtc ggattaggtt gttggtgagg taatggctca ccaagcccac       240
gatccgtagc tggtctgaga ggatgaccag ccagactgga actgagacac ggtccagact       300
cctacgggag gcagcagtga ggaatcttcc acaatggggg caaccctgat ggagcaacgc       360
cgcgtgcagg atgaaggcct tcgggtcgta aactgctttt attagtgaag aatatgacgg       420
taactaatga ataaggatcg gctaactacg tgccagcagc cgcggtcata cgtaggatcc       480
gagcgttatc cggagtgact gggcgtaaag agttgcgtag gtggtttgtt aagtaggtag       540
tgaaatctgg cggctcaacc gtacaggcta ttacctaaac tggcaaactc gagaatggta       600
gaggtaactg gaatttcttg tgtaggagtg aaatccgtag atataagaag gaacaccaat       660
ggcgtaggca ggttactgga ccatttctga cactaaggca cgaaagcgtg gggagcgaac       720
gggattagat accccggtag tccacgccgt aaacgatgga tactagctgt tggaggtatc       780 gacccccttca gtagcgaagc taacgcgtta agtatcccgc ctgtgagta cggccgcaag      840 gctaaaacat aaaggaattg acggggaccc gcacgagcgg tggatcgtgt tctttaattc      900
gatgctaaac ggagaacctt accagggttt gacatccttg gaatctctag gaaactagag      960
agtgcctttg gaaccaagtg acaggtgttg catggccgtc gtcagctcgt gtcgtgagat      1020
gtttggttaa gtccatcaac gagcgcaacc cttatagtta gttggatttt tctagctaga     1080
ctgccccggt aacggggagg aaggagggga tgatgtcagg tcagtattac ccttacaccc     1140
tgggctagaa acacgataca atggctagta caatgcgcag cgaagccgcg aggtggagca     1200
aatcgcatca aagctagtct cagttcggat tgcaggctga aactcgcctg catgaagtcg     1260
gaatcgctag taatcgcaaa tcagcaagtt gcggtgaata cgttcccggg tcttgtacac     1320
accgcccgtc aagccatgaa agtgaccaac acccgaagtc cgattcgtcg gcctaaggtg     1380
gggggc                                                                1386
```

<210> SEQ ID NO 46
<211> LENGTH: 1406
<212> TYPE: DNA

<213> ORGANISM: Artificial
<220> FEATURE:
<223> OTHER INFORMATION: Uncultured Flexibacteraceae bacterium clone
      GL2-106 16S ribosomal RNA gene, partial sequence

<400> SEQUENCE: 46

```
ctggcggcag gcctaataca tgcaagtcga acggtgcctt cgggtacagt ggcaaacggg      60
tgcgtaacgc gtaagcaacc tgcctcatac tgggggatag cccggcgaaa gctgggtaa     120
ccccgcatgg tcccttcgg tcacctgact ggttgggtaa acatttatgg gtatgagagg     180
ggcttgcgtc tgattagcta gttggcaggg taacggccta ccaaggcgat gatcagtagg     240
ggttctgaga ggattggccc ccacatgggt actgagagac ggacccaact cctacgggag     300
gcagcagtag ggaatattgg gcaatggagg caactctgac ccagccatgc cgcgtgcagg     360
atgaaggcgc tcagcgttgt aaactgcttt tatccaggaa gaatggtatc cctgcgggg     420
tatttgccgg tactgagga ataagcaccg gctaactccg tgccagcagc cgcggtaata     480
cggagggtgc gagcgttgtc cggatttatt gggtttaaag ggtgcgtagg tggcttctta     540
agtctggttt gaaagtcggc ggcttaaccg ttggatgtgg ctggaaactg ggggcttga     600
attacttggc ggtagccgga atgggtcatg tagcggtgaa atgcatagat atgacccgga     660
accccgattg cgaaggcagg ctactacgat ttgattgaca ctgaggcacg agagcatggg     720
tagcgaacag gattagatac cctggtagtc catgccgtaa acgatgatta ctggctgttt     780
gcccgatagg gtgagtggct gagcgaaagc gttaagtaat ccacctgggg agtacgccgg     840
caacggtgaa actcaaagga attgacgggg gtccgcacaa gcggtggagc atgtggttta     900
attcgatgat acgcgaggaa ccttacctgg gctagaatgt gaaggaagta tttggaaaca     960
gatgcgtgta gcaatacacc tgaaacaagg tgctgcatgg ctgtcgtcag ctcgtgccgt    1020
gaggtgttgg gttaagtccc gcaacgagcg caacccctac ggtcagttac cagcatgtaa    1080
tgatggggac tctggccgga ctgcctgcgc aagcagagag gaaggcgggg acgacgtcaa    1140
gtcatcatgg cccttacgcc cagggcgaca cacgtgctac aatgggaggt acagcgggtc    1200
gcgatagggt aacctggagc caatcttgta aagcctctca cagttcggat tggggtctgc    1260
aacccgaccc catgaagctg gaatcgctag taatcgcgca tcagccatgg cgcggtgaat    1320
acgttcccgg accttataca caccgcccgt caagccatgg gagttggggg gacctgaagt    1380
tcggggtaac aaccggacaa gggtaa                                          1406
```

<210> SEQ ID NO 47
<211> LENGTH: 1404
<212> TYPE: DNA
<213> ORGANISM: Artificial
<220> FEATURE:
<223> OTHER INFORMATION: Uncultured Chryseobacterium sp. clone GR2-36
      16S ribosomal RNA gene, partial sequence

<400> SEQUENCE: 47

```
gaacgctagc gggaggccta acacatgcaa gccgagcggt atttgttctt cggaacagag      60
agagcggcgc acgggtgcgg aacacgtgtg caacctgcct ttatctgggg gatagccttt     120
cgaaaggaag attaataccc cataatatat tgagtggcat catttgatat agaaaactcc     180
ggtggataga gatgggcacg cgcaagatta gatagttggt gaggtaacgg ctcaccaagt     240
caatgatctt tagggggcct gagagggtga tccccacac tggtactgag acacggacca     300
gactcctacg ggaggcagca gtgaggaata ttggacaatg ggttagcgcc tgatccagcc     360
atcccgcgtg aaggacgacg gccctatggg ttgtaaactt cttttgtata gggataaacc     420
```

```
tactctcgtg agagtagctg aaggtactat acgaataagc accggctaac tccgtgccag    480
cagccgcggt aatacggagg gtgcaagcgt tatccggatt tatttggttt aaagggtccg    540
taggcggatc tgtaagttag tggtgaaatc tcacagctta actgtgaaac tgccattgat    600
actgcaggtc ttgagtaaat ttgaagtggc tggaataagt agtgtagcgg tgaaatgcat    660
agatattact tagaacacca attgcgaagg caggtcacta agatttaact gacgctgatg    720
gacgaaagcg tggggagcga acaggattag atactctggt agtccacgcc gtaaacgatg    780
ctaactcgtt ttttgtgatt cgtcatgaga gactaagcga aagtgataag ttagccacct    840
ggggagtacg ttcgcaagaa tgaaactcaa aggaattgac gggggcccgc acaagcggtg    900
gattatgtgg tttaattcga tgatacgcga ggaaccttac caagacttaa atgggaaatg    960
acagatttag aaatagatcc ttcttcggac atttttcaag gtgctgcatg gttgtcgtca   1020
gctcgtgccg tgaggtgtta ggttaagtcc tgcaacgagc gcaacccctg tcactagttg   1080
ctagcattaa gttgaggact ctagtgagac tgcctacgca agtagagagg aaggtgggga   1140
tgacgtcaaa tcatcacggc ccttacgtct tgggccacac acgtaataca atggccggta   1200
cagagggcag ctacacagcg atgtgatgca aatctcgaaa gccggtctca gttcggattg   1260
gagtctgcaa ctcgactcta tgaagctgga atcgctagta atcgcgcatc agccatggcg   1320
cggtgaatac gttcccgggc cttgtacaca ccgcccgtca gccatggaa gtctgggta    1380 cctgaagtcg gtgaccgtaa aagg                                         1404

<210> SEQ ID NO 48
<211> LENGTH: 1402
<212> TYPE: DNA
<213> ORGANISM: Artificial
<220> FEATURE:
<223> OTHER INFORMATION: Uncultured Bdellovibrio sp. clone GR2-101 16S
      ribosomal RNA gene, partial sequence

<400> SEQUENCE: 48
acgcttgcgg cgcgcctaat acatgcaagt cgaacgaacc agcgatggtg agtggcgcac     60
gggtgagtaa cgcgtggata atctgccctc tactggggaa taactaaccg aaaggttagc    120
taataccgca tgagaccaca gtttccgagg aaacagaggt taaagattta ttggtagagg    180
atgagtctgc gtgggattag ctagttggtg gggtaacggc ctaccaaggc gacgatctct    240
aacaggtctg agaggatgac ctgtcacact ggaactgaga cacggtccag actcctacgg    300
gaggcagcag tagggaatat tgcgcaatgg gggaaaccct gacgcagcga cgccgcgtga    360
gtgatgaagg ccttagggtc gtaaagctct gttgtacggg aagaacaaaa tgacggtacc    420
gtataagaaa ggatcggcta acttcgtgcc agcagccgcg gtaatacgag gatcctagc     480 gttgttcgga atcattgggc gtaaagggtg tgcaggcggc catgtaagtc agttgtgaaa    540
gccccgggct caacccggga agtgcttctg atactgcttg gcttgagtat tggataggtg    600
agtggaattc caggtgtagt ggtgaaatac gtagatatct ggaggaacac cggcggcgaa    660
ggcggctcac tggccatata ctgacgctga acacgaaag cgtgggtagc aaacaggatt    720
agataccctg gtagtccacg ccgtaaacga tgggtacttg tgttggagg tattgacccc    780 ttcagtgccg aagcaaacgc gataagtacc ccgcctgggg agtacggccg caaggttaaa    840
actcaaagaa attgacgggg gcccgcacaa gcggtggagc atgtggttta attcgatgca    900
acgcgaaaaa ccttacctgg gctcgaaatg taacggaagt tagcagaaat gttaacgcct    960
tcgggccgtt atataggtgc tgcatggctg tcgtcagctc gtgtcgtgag atgttgggtt   1020
aagtcccgca acgagcgcaa cccctgcctt tagttgccag catttagttg ggcactctag   1080
```

```
agggactgcc ggtgttaaac cggaggaagg tggggatgac gtcaagtcct catggccctt      1140
atgtccaggg ctacacacgt gctacaatgg tagatacaaa gggttgccaa cctgcaaagg      1200
ggagctaatc ccagaaagtc tatctaagtt cggattgagg tctgcaactc gacctcatga      1260
aggtggaatc gctggtaatc gcggatcagc atgccgcggt gaatacgttc ccgggccttg      1320
tacacaccgc ccgtcacacc atgaaagtcg gttgtaccag aagtcgctgt gctaaccgta      1380 aggggggcagg cgcccaaggt at                                              1402

<210> SEQ ID NO 49
<211> LENGTH: 1410
<212> TYPE: DNA
<213> ORGANISM: Artificial
<220> FEATURE:
<223> OTHER INFORMATION: Uncultured Flavobacteriaceae bacterium clone
      LL2-82 16S ribosomal RNA gene, partial sequence

<400> SEQUENCE: 49
gcgggaggcc taacacatgc aagccgagcg gtagagattc ttcgggatct tgagagcggc      60
gtacgggtgc gtaacacgtg tgcaacctgc ctttatctgg gagatagcct ttcgaaagga     120
agattaatat cccataatat attgattggc atcgattaat attgaaagct ccggcggata     180
aagatgggca cgcgcaagat tagatagttg gtgaggtaac ggctcaccaa gtcgatgatc     240 tttaggggc ctgagagggt gatccccac actggtactg agacacggac cagactccta     300
cgggaggcag cagtgaggaa tattggacaa tgggtggaag cctgatccag ccatcccgcg     360
tgaaggaata agggcctatg gcttataaac ttctttttgtg cagggataaa cctaccctcg     420
tgagggtagc tgaaggtact gtacgaataa gcaccggcta actccgtgcc agcagccgcg     480
gtaatacgga gggtgcaagc gttatccgga tttattgggt ttaaagggtc cgtaggcggg     540
cttataagtc agtggtgaaa gccggcagct taactgtcga actgccattg atactgtaag     600
tcttgagtat atttgaggta gctggaataa gtagtgtagc ggtgaaatgc atagatatta     660
cttagaacac caattgcgaa ggcaggttac caagttataa ctgacgctga tggacgaaag     720
cgtggggagc gaacaggatt agataccctg gtagtccacg ctgtaaacga tgctaactcg     780
ttttttgggc attaagcttc agagaccaag cgaaagtgat aagttagcca cctgggagt      840 acgttcgcaa gaatgaaact caaaggaatt gacgggggcc cgcacaagcg gtggattatg     900
tggtttaatt cgatgatacg cgaggaacct taccaagact taaatgggaa tagacagacg     960
cagaaatgtg ttttttcttcg gacaatttttc aaggtgctgc atggttgtcg tcagctcgtg    1020
ccgtgaggtg ttaggttaag tcctgcaacg agcgcaaccc ctgccaatag ttgccatcat    1080
tcagttgggg actctattgg gactgcctac gcaagtagcg aggaaggtgg ggatgacgtc    1140
aaatcatcac ggcccttacg tcttgggcca cacacgtaat acaatggccg gtacagaggg    1200
cagctacact gcgaagtgat gcgaatctcg aaagccggtc tcagttcgga ttggagtctg    1260
caactcgact ctatgaagct ggaatcgcta gtaatcgcgc atcagccatg gcgcggtgaa    1320
tacgttcccg ggccttgtac acaccgcccg tcaagccatg gaagtttggg gtacctgaag    1380
tcggtgaccg taaaaggagc tgcctagggt                                      1410

<210> SEQ ID NO 50
<211> LENGTH: 1002
<212> TYPE: DNA
<213> ORGANISM: Artificial
<220> FEATURE:
<223> OTHER INFORMATION: Uncultured Lysobacter sp. clone LR2-32 16S
      ribosomal RNA gene, partial sequence
```

<400> SEQUENCE: 50

```
ctggcggcag gcctaacaca tgcaagtcga acggcagcat ggaaagtact tgtactttcc      60
gatggcgagt ggcggacggg tgaggaatgc atcggaatct gcccatttgt gggggataac     120
gtagggaaac ttacgctaat accgcatacg accttcgggt gaaagcaggg gatcttcgga    180
ccttgcgcag atggatgagc cgatgccgga ttagctagtt ggcggggtaa aggccctcca    240
aggcgacgat ccgtagctgg tctgagagga tgatcagcca cactggaact gagacacggt    300
ccagactcct acgggaggca gcagtgggga atattggaca atgggcgcaa gcctgatcca    360
gccatgccgc gtgtgtgaag aaggccttcg ggttgtaaag cacttttgtt ggggaagaaa    420
agcagttggt taatacccga ttgtcatgac ggtacccaaa gaataagcac cggctaactt    480
cgtgccagca gccgcggtaa tacgaagggt gcaagcgtta ctcggaatta ctgggcgtaa    540
agcgtgcgta ggtggtttgt taagtctgat gtgaaagccc tgggctcaac ctggaactg     600
cattggatac tggcagactg gagtgcgta  gagggtagcg gaattccgg  tgtagcagtg    660
aaatgcgtag atatcgggag gaacatctgt ggcgaaggcg ctacctgga  ccagcactga    720
cactgaggca cgaaagcgtg gggagcaaac aggattagat accctggtag tccacgccct    780
aaacgatgcg aactggatgt tgggtgcact taggcactca gtatcgaagc taacgcgtta    840
agttcgccgc ctgggagta  cggtcgcaag actgaaactc aaaggaattg acggggccc     900
gcacaagcgg tggagtatgt ggtttaattc gatgcaacgc gaagaacctt acctggcctt    960
gacatgtcga gaacttacta gagatagttt ggtgccttcg gg                      1002
```

<210> SEQ ID NO 51
<211> LENGTH: 1435
<212> TYPE: DNA
<213> ORGANISM: Artificial
<220> FEATURE:
<223> OTHER INFORMATION: Uncultured Neisseriaceae bacterium clone LR2-63 16S ribosomal RNA gene, partial sequence

<400> SEQUENCE: 51

```
cggcatgctt tacacatgca agtcgaacgg caacgaggag aagcttgctt ctctgtcggc     60
gagtggcgaa cgggtgagta tagcatcgga acgtgccaag tagtgtggga taaccaaacg   120
aaagtttggc taataccgcg taagctccaa ggaggaaagt aggggacctg ataaggcctt   180
acgctatttg atcggccgat gtcggattag ctagttggtg gggtaatggc tcaccaaggc   240
aatgatccgt agcgggtctg agaggacgat ccgccacact gggactgaga cacggcccag  300
actcctacgg gaggcagcag tgggaattt  tggacaatgg gggaaaccct gatccagcca   360
tgccgcgtgt atgaagaagg ccttagggtt gtaaagtact tttgttaggg aagaaaagct   420
agttttaat  aaaaattagt gatgacggta cctaaagaat aagcaccggc taactacgtg   480
ccagcagccg cggtaatacg tagggtgcaa gcgttaatcg gaattattgg gcgtaaagcg   540
agtgcagacg gttacttaag ccagatgtga atccccaag  cttaacttgg gacgtgcatt   600
tggaactggg tgactagagt gtgtcagagg gaggtagaat tccacatgta gcggtggaat   660
gcgtagagat gtggaggaat accgatggcg aaggcagctt cctgggataa cactgacgtt   720
gaggctcgaa agcgtgggga gcaaacagga ttagataccc tggtagtcca cgccctaaac   780
gatggcaatt agctgttggg ctttgaaagg cttagtagcg aagctaacgc gagaaattgt   840
ccgcctgggg agtacggtcg caagattaaa actcaaagga attgacgggg acccgcacaa    900
gcggtggatg atgtggatta attcgatgca acgcgaagaa ccttacctgg tcttggcatg    960
```

| | |
|---|---|
| tacggaattt tttagagata aagaagtgcc ttcgggaacc gtaacacagg tgctgcatgg | 1020 |
| ctgtcgtcag ctcgtgtcgt gagatgttgg gttaagtccc gcaacgagcg caacccttgt | 1080 |
| cattagttgc catcatttgg ttgggcactc taatgagact gccggtgata agccggagga | 1140 |
| aggtggggat gatgtcaagt cctcatggcc cttatgacca gggcttcaca cgtcatacaa | 1200 |
| tggtaggtac agagggtagc caagccgtaa ggtggagcca atctcagaaa gcctatcgta | 1260 |
| gtccggattg tagtctgcaa ctcgactaca taaagtcgga atcgctagta atcgcagatc | 1320 |
| agcatgctgc ggtgaatacg ttcccgggtc ttgtacacac cgcccgtcac accatgggag | 1380 |
| tgggagatgc cagaagtggg taggataacc atatggggtc cgctcaccac ggtat | 1435 |

<210> SEQ ID NO 52
<211> LENGTH: 1401
<212> TYPE: DNA
<213> ORGANISM: Artificial
<220> FEATURE:
<223> OTHER INFORMATION: Uncultured Flexibacteraceae bacterium clone
      LR2-77 16S ribosomal RNA gene, partial sequence

<400> SEQUENCE: 52

| | |
|---|---|
| gcggcaggcc taatacatgc aagtcgaacg gtgggtaacc acagtggcaa acgggtgcgt | 60 |
| aacgcgtaag caacctgcct ccaactgggg gatagcccgg cgaaagctgg ggtaaacccg | 120 |
| cacggtccaa ttgactcacc tgggttgatt ggtaaacatt tatgggttgg agaggggctt | 180 |
| gcgtctgatt agctagttgg tggggtaacg gctcaccaag gccttgatca gtaggggttc | 240 |
| tgagaggatt ggccccacca tgggtactga gatacggacc caactcctac gggaggcagc | 300 |
| agtagggaat attgggcaat ggaggcaact ctgacccagc catgccgcgt gcaggatgaa | 360 |
| ggcgctcagc gttgtaaact gcttttactc atgaagaacg gcaggtttgc ggacctgtgt | 420 |
| gacggtaatg agggaataag caccggctaa ctccgtgcca gcagccgcgg taatacggag | 480 |
| ggtccgagcg ttgtccggat ttattgggtt taaagggtgc gtaggtggtt tggtaagtct | 540 |
| ggtttgaaag ctggtcgctc aacgatcaga tgtggctgga aactgtcgaa cttgaatgcg | 600 |
| atggcggtcg ccggaacggg tcatgtagcg gtgaaatgca tagatatgac ccagaactcc | 660 |
| gattgcgaag gcaggcgacc aggtcgtgat tgacactgag gcacgagagc atggggagcg | 720 |
| aacaggatta gataccctgg tagtccatgc cgtaaacgat gattactggc tgttgggcct | 780 |
| gatggttcag tggctgagcg aaagcgttaa gtaatccacc tggggagtac gccggcaacg | 840 |
| gtgaaactca aaggaattga cggggtccg cacaagcggt ggagcatgtg gtttaattcg | 900 |
| atgatacgcg aggaacctta cctgggctag aatgtgagag aagttatcag aaatggtagc | 960 |
| gtgcagcaat gtactcaaaa caaggtgctg catggctgtc gtcagctcgt gccgtgaggt | 1020 |
| gttgggttaa gtcccgcaac gagcgcaacc cctgtgacta gttgccatca ggtaatgctg | 1080 |
| ggaactctag tcagactgcc tgcgcaagca gagaggaagg aggggacgac gtcaagtcat | 1140 |
| catgcccctt acgccagggc cgacacacgt gctacaatgg tcggtacagc gggtagcgag | 1200 |
| gcagtaatgc ggagccaatc ttgtaaagcc ggtcacagtt cggattgggg tctgcaaccc | 1260 |
| gacccccatga agctgaatc gctagtaatc gcgcatcagc catggcgcgg tgaatacgtt | 1320 |
| cccggacctt gtacacaccg cccgccaagc catgggagtt gggggggacct gaagtgggag | 1380 |
| gtaatattcc catcagggta a | 1401 |

<210> SEQ ID NO 53
<211> LENGTH: 1416
<212> TYPE: DNA
<213> ORGANISM: Artificial -continued

```
<220> FEATURE:
<223> OTHER INFORMATION: Uncultured Anaerococcus sp. clone ML2-55 16S
      ribosomal RNA gene, partial sequence

<400> SEQUENCE: 53
ctggcggcgt gcttaacaca tgcaagtcga acgatgaaac tttaatgaac ccttcgggga     60
gaattaaagc ggattagtgg cgaacggtg agtaacgcgt gagtaacctg ccttacacaa    120
ggggatagcc tttggaaacg aagaataata ccctataaaa ccataaaagc acatgcaatt    180
atggtcaaag tgatagcggt gtaagatgga cttgcgtctg attagctagt tggtgagata    240
aaggcccacc aaggcaacga tcagtagccg gcttgagaga gtgtacggcc acattgggac    300
tgagacacgg cccagactcc tacgggaggc agcagtgggg aattttgcac aatgggggaa    360
accctgatgc agcgacgccg cgtgatttag aaggccttcg ggttgtaaaa atcttttgta    420
taggaagaaa atgacagtac tatacgaata aggtccggct aattacgtgc cagcagccgc    480
ggtaatacgt aaggaccgag cgttgtccgg aatcattggg cgtaaagggt acgtaggcgg    540
ctagaaaagt tagaagtcaa aggctatagc tcaactatag taagcttcta aaactattta    600
gcttgagaga tggaagggaa agtggaattc ctagtgtagc ggtggaatgc gcagatatta    660
ggaggaatac cggtggcgaa ggcgactttc tggccatttt ctgacgctga ggtacgaaag    720
cgtgggtagc aaacaggatt agataccctg gtagtccacg ccgtaaacga tgagtgttag    780
gtgtctggag tcaaatctgg gtgccgcagc aaacgcatta aacactccgc ctggggagta    840
cgcacgcaag tgtgaaactc aaaggaattg acggggaccc gcacaagcag cggagcatgt    900
ggtttaattc gacgcaacgc gaagaacctt accaagtctt gacatatttt agaagcaatt    960
agagatagtt gcctatatct tcggataact aaaatacagg tggtgcatgg ttgtcgtcag   1020
ctcgtgtcgt gagatgttgg gttaagtccc ataacgagcg caacccctat tgctagttac   1080
catcattaag ttggggactc tagtaatact gccggtgaca aaccggagga aggtggggat   1140
gacgtcaaat catcatgccc tttatgactt gggctacaca cgtgctacaa tggcaggtac   1200
acagggaagc aagactgtga agttaagcaa aactcaaaaa gcctgtccca gttcggattg   1260
cactctgcaa ctcgagtgca tgaagttgga gttgctagta atcgcagatc agaatgctgc   1320
ggtgaatgcg ttcccgggtc ttgtacacac cgcccgtcac accatggaag ttggcaatac   1380
ccgaagcctg tgagcgaacc cttggggcgc agcagt                              1416
```